United States Patent [19]
Hibino et al.

[11] Patent Number: 5,159,446
[45] Date of Patent: Oct. 27, 1992

[54] ELECTRONIC ENDOSCOPE SYSTEM PROVIDED WITH A SEPARATE CAMERA CONTROLLING UNIT AND MOTOR CONTROLLING UNIT

[75] Inventors: Hiroki Hibino, Tokyo; Yoshikatsu Nagayama, Sagamihara; Mutsumi Yoshikawa, Hachioji; Toshiyuki Takara, Higashimurayama; Masahito Goto; Akira Suzuki, both of Hachioji; Sakae Takehana, Machida; Yoshinao Oaki, Hachioji; Koichi Yoshimitsu; Yoshisada Aoki, both of Hachioji, all of Japan

[73] Assignee: Olympus Optical Co., Ltd., Tokyo, Japan

[21] Appl. No.: 719,272

[22] Filed: Jun. 21, 1991

[51] Int. Cl.5 .......................... A63B 1/04; H04N 7/18
[52] U.S. Cl. ............................................ 358/98; 128/6
[58] Field of Search ............................ 358/98; 128/4,6

[56] References Cited

U.S. PATENT DOCUMENTS

| | | | |
|---|---|---|---|
| 4,621,618 | 11/1986 | Omagari | 128/6 |
| 4,941,456 | 7/1990 | Wood et al. | 128/6 |
| 5,018,509 | 5/1991 | Suzuki et al. | 358/98 X |
| 5,060,632 | 10/1991 | Hibino et al. | 358/98 X |
| 5,088,492 | 2/1992 | Takayama et al. | 358/98 X |

Primary Examiner—Victor R. Kostak
Attorney, Agent, or Firm—Armstrong & Kubovcik

[57] ABSTRACT

At least one controlling unit of a controlling unit for controlling a bending driving motor bending driving a bendable portion, a controlling unit for controlling an advancing and retreating driving motor advancing and retreating moving an insert section and a controlling unit for controlling a rotating driving motor rotating driving the insert section and a camera controlling unit for processing a signal for an imaging device are made separate from each other so that such existing scope as an electronic scope or fiber scope fitted with a TV camera may be used.

42 Claims, 52 Drawing Sheets

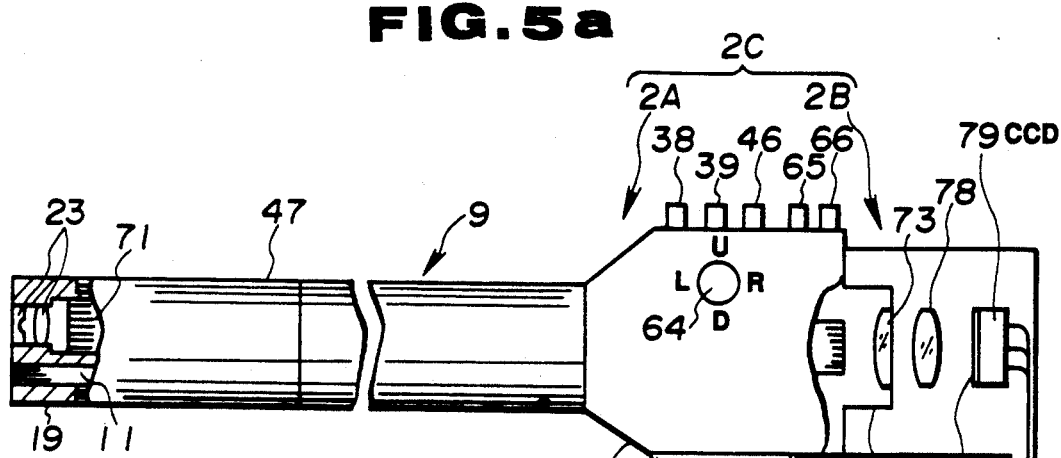
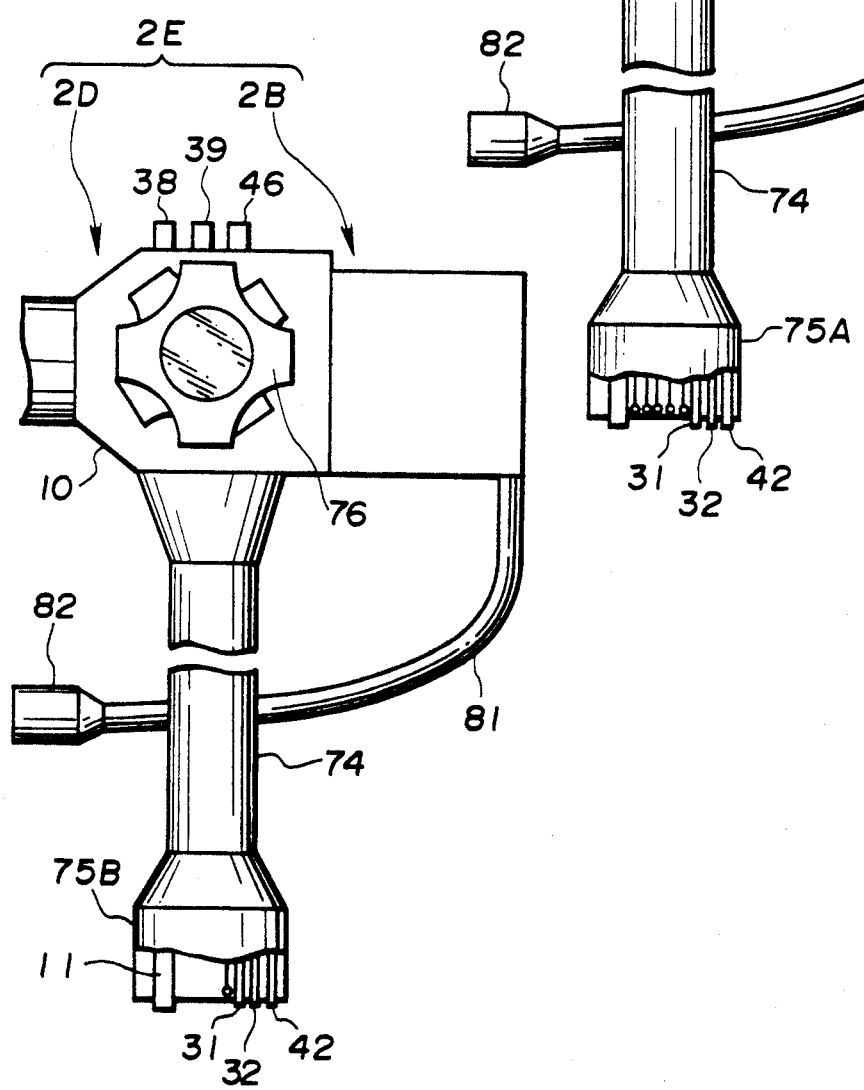

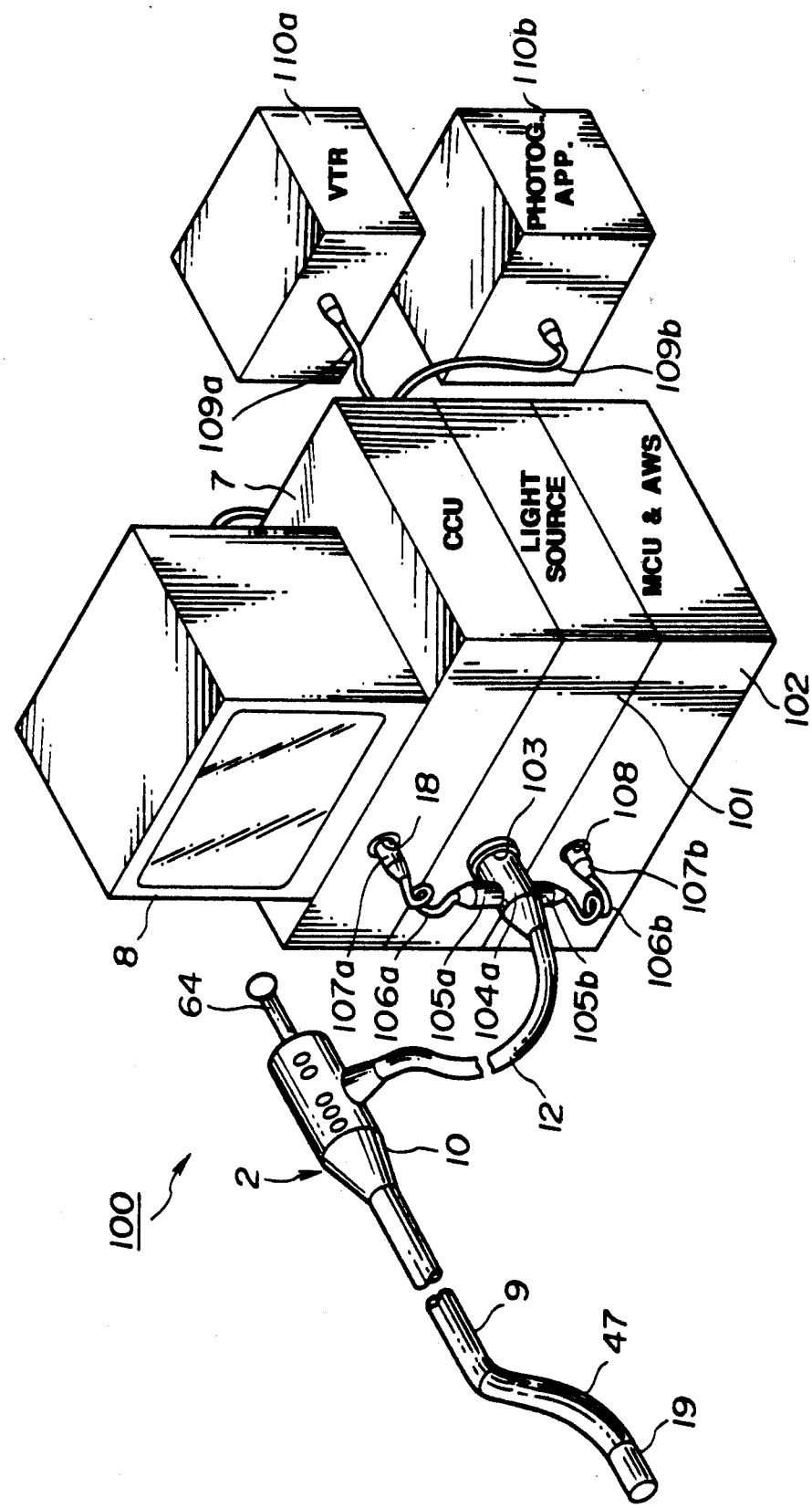

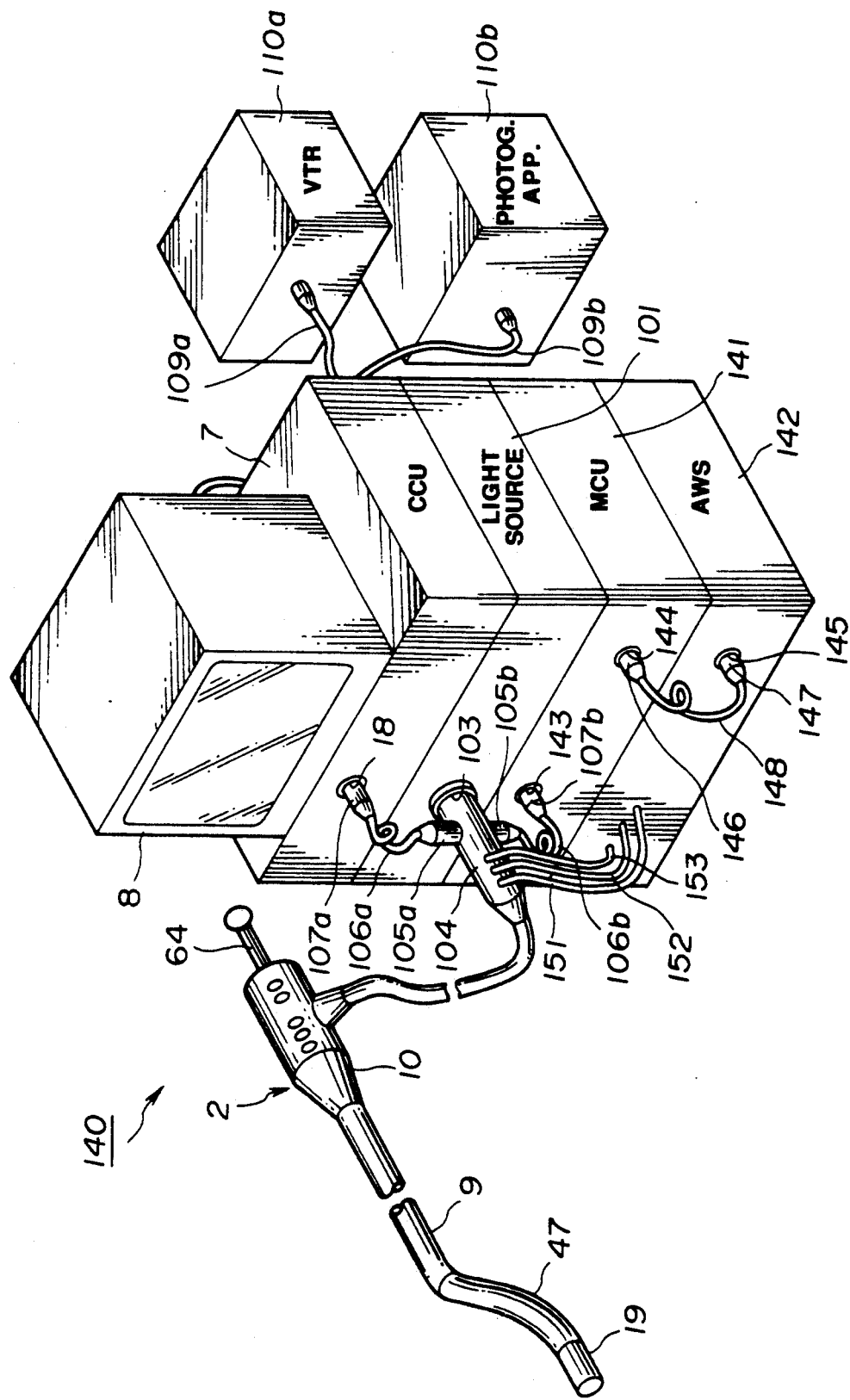

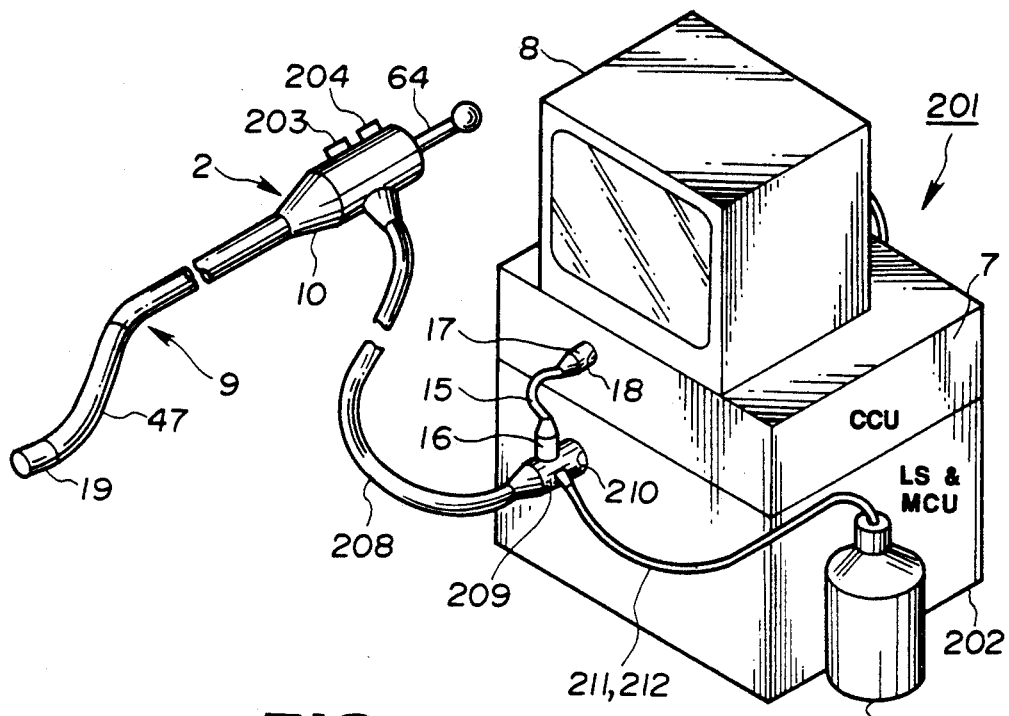
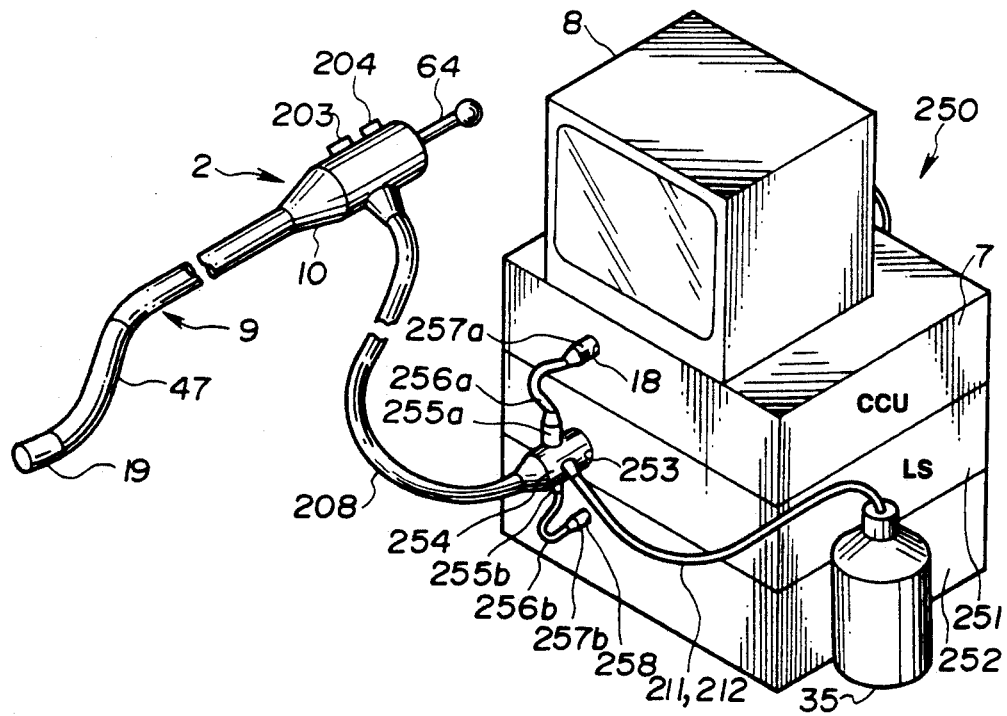

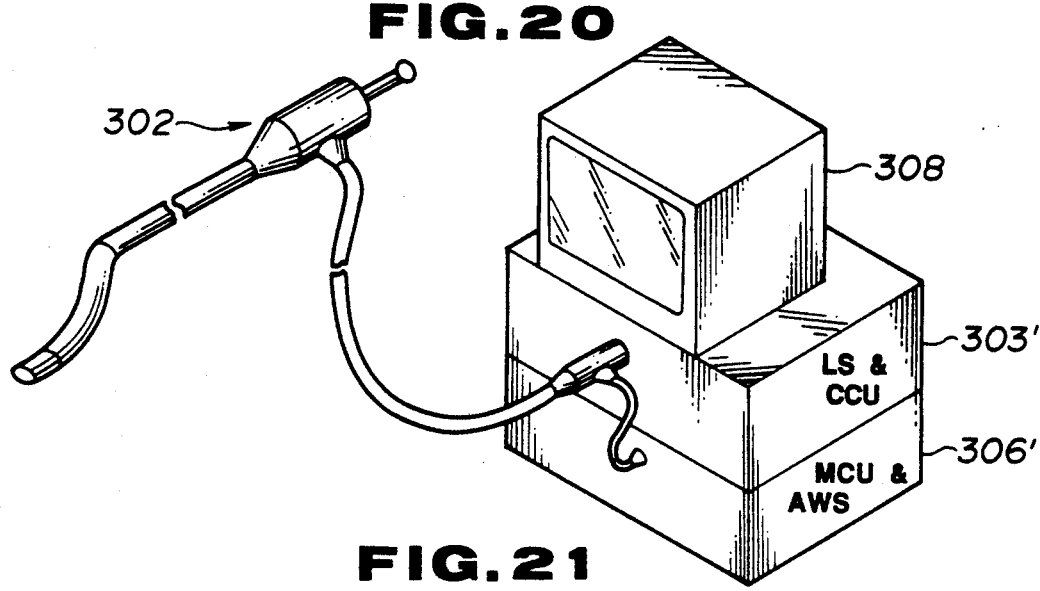
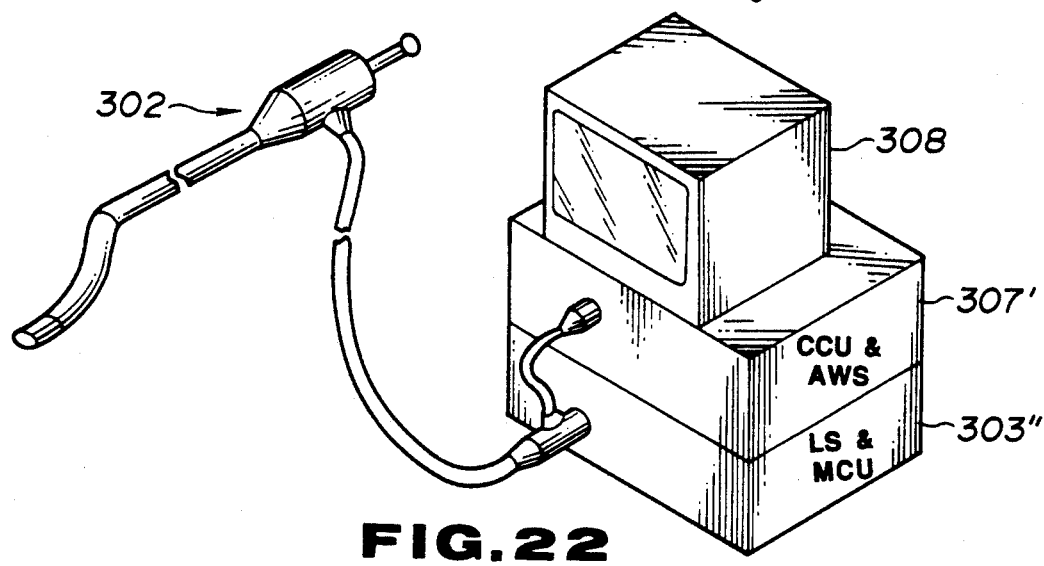
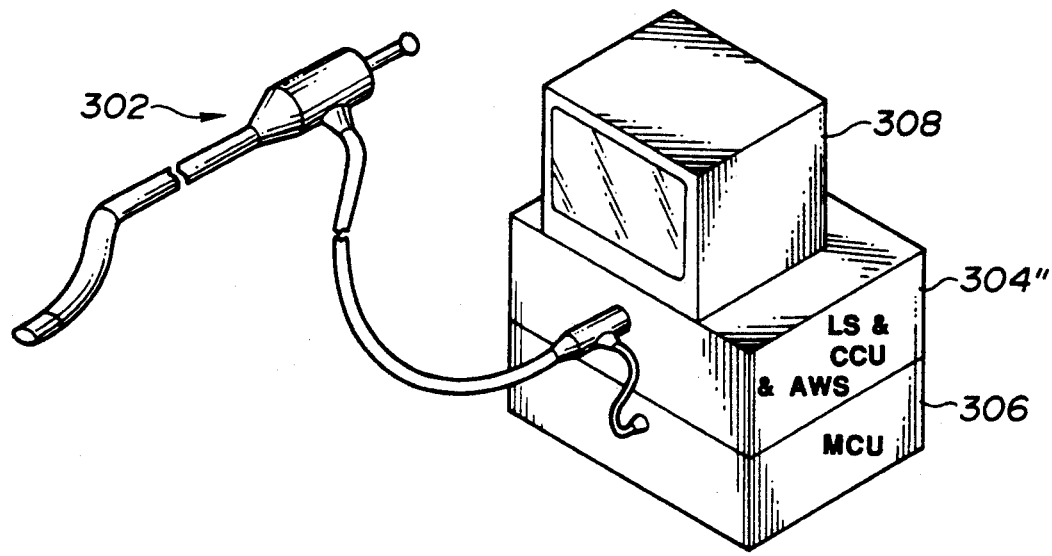

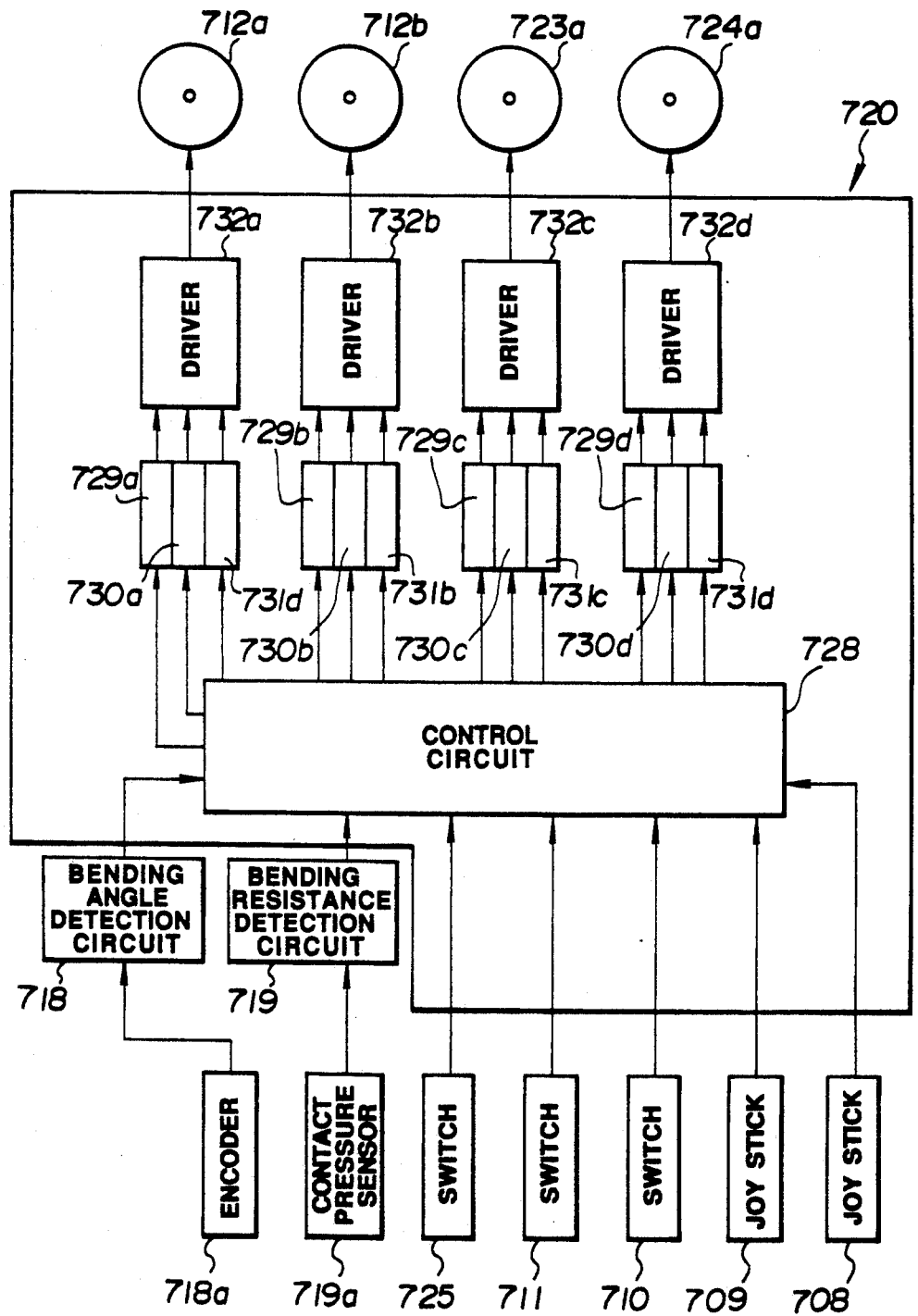

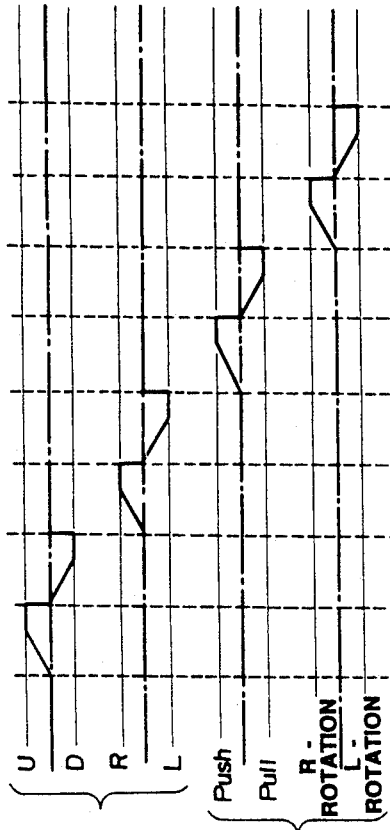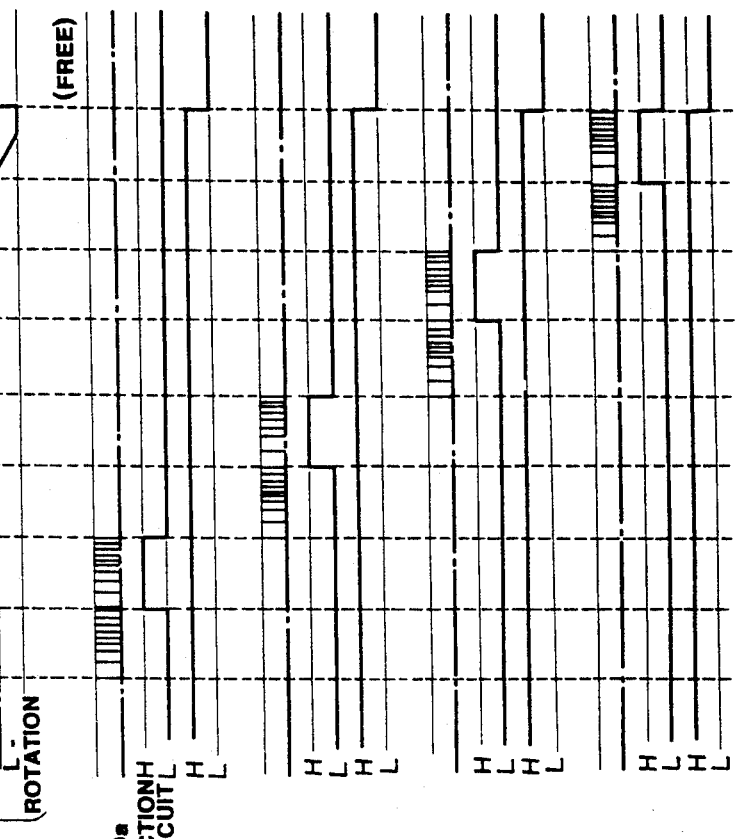
FIG.30(a) JOY STICK 708
FIG.30(b) JOY STICK 709
FIG.30(c) SPEED CONTROL CIRCUIT 729a
FIG.30(d) ROTATING DIRECTION INDICATION CIRCUIT 730a
FIG.30(e) FREE/LOCK CIRCUIT 731a
FIG.30(f) 729b
FIG.30(g) 730b
FIG.30(h) 731b
FIG.30(i) 729c
FIG.30(j) 730c
FIG.30(k) 731c
FIG.30(l) 729d
FIG.30(m) 730d
FIG.30(n) 731d

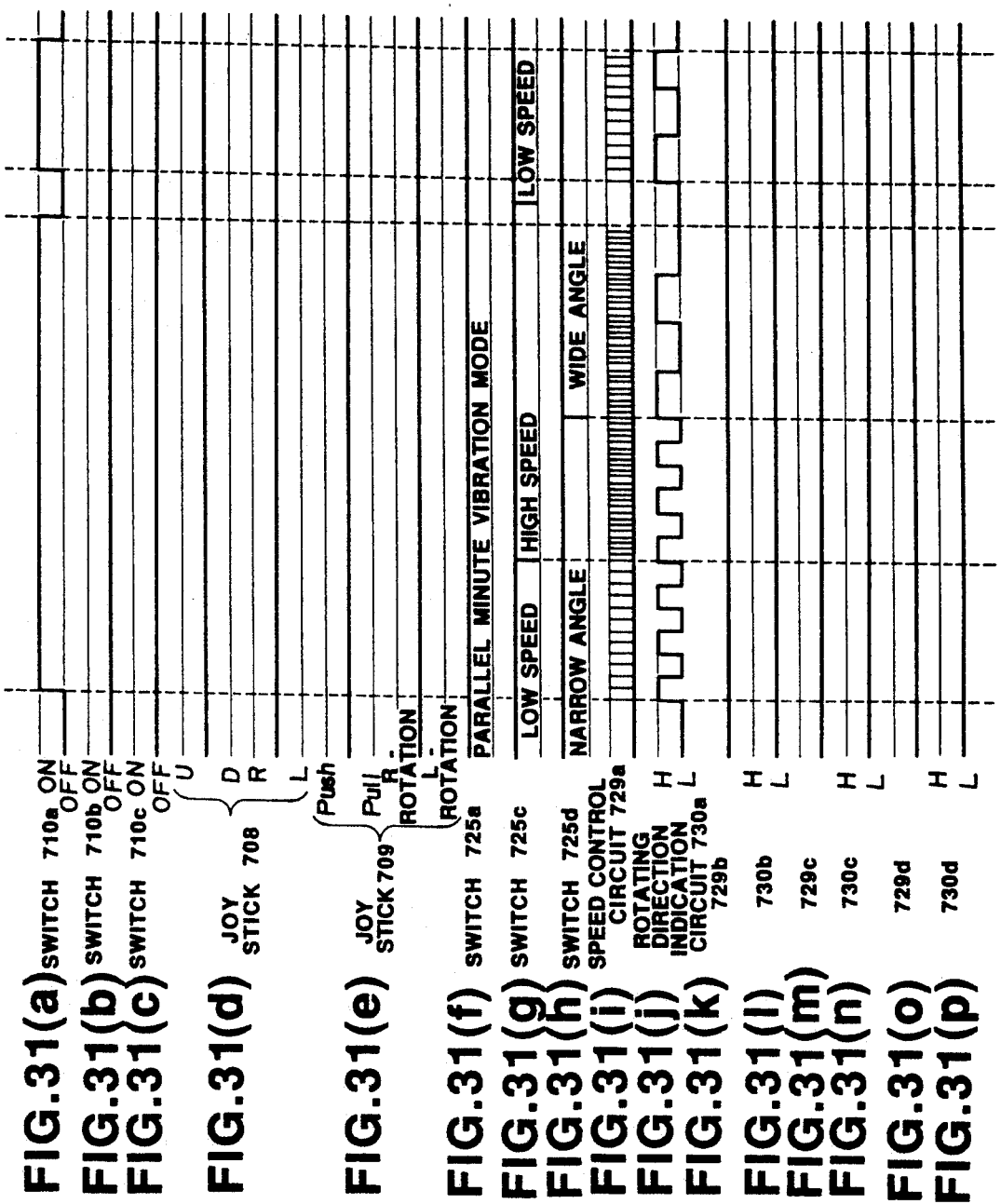

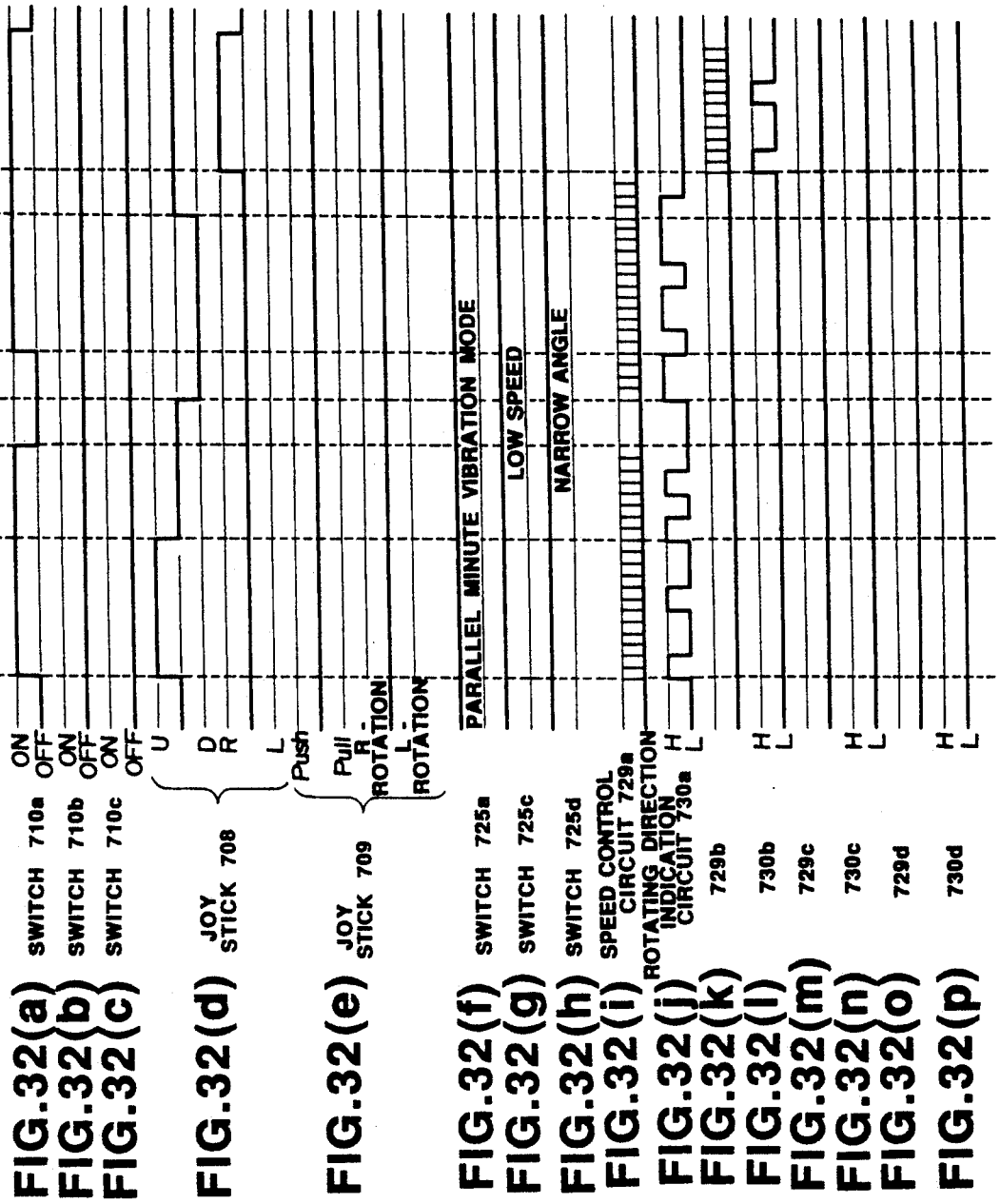

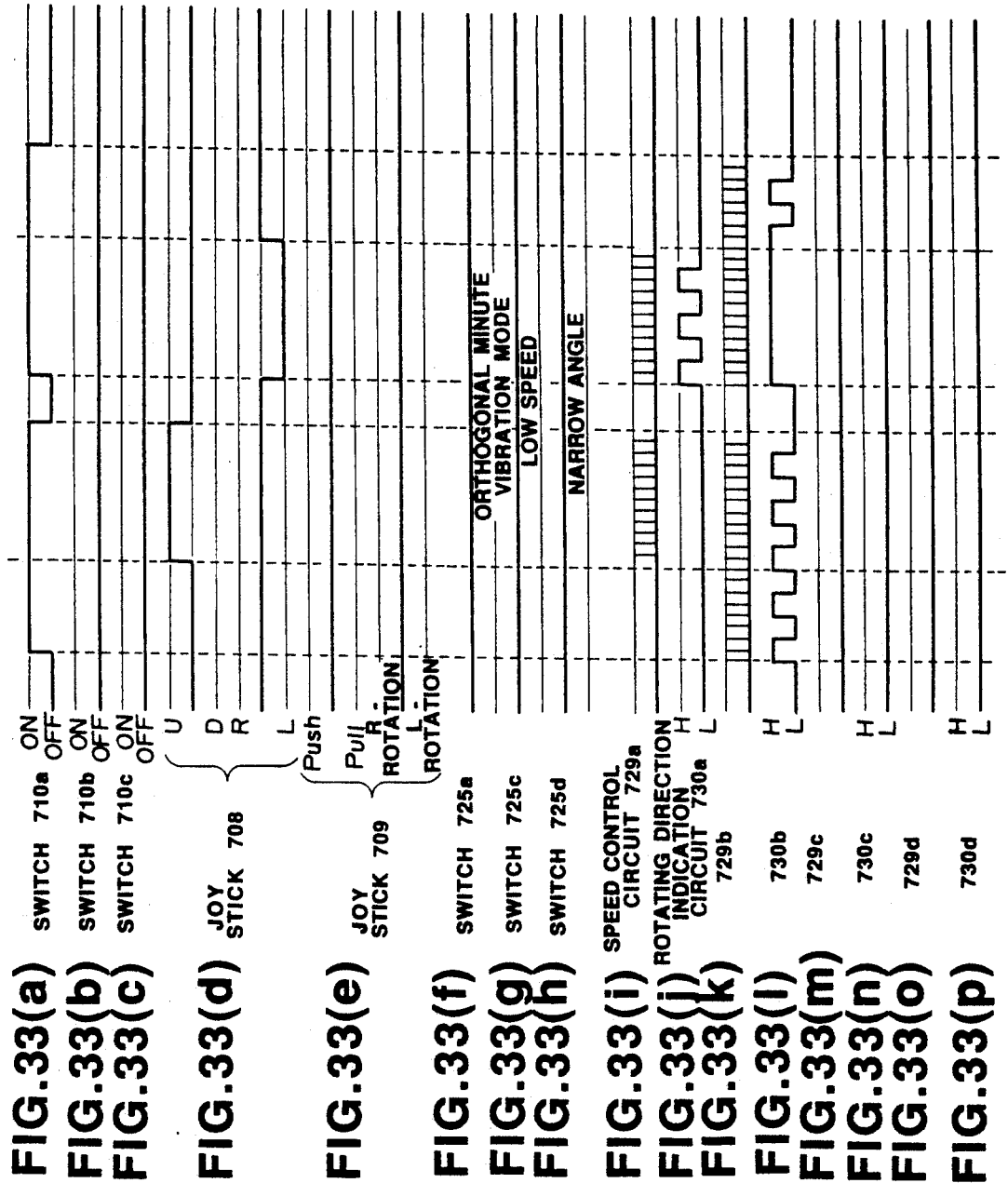

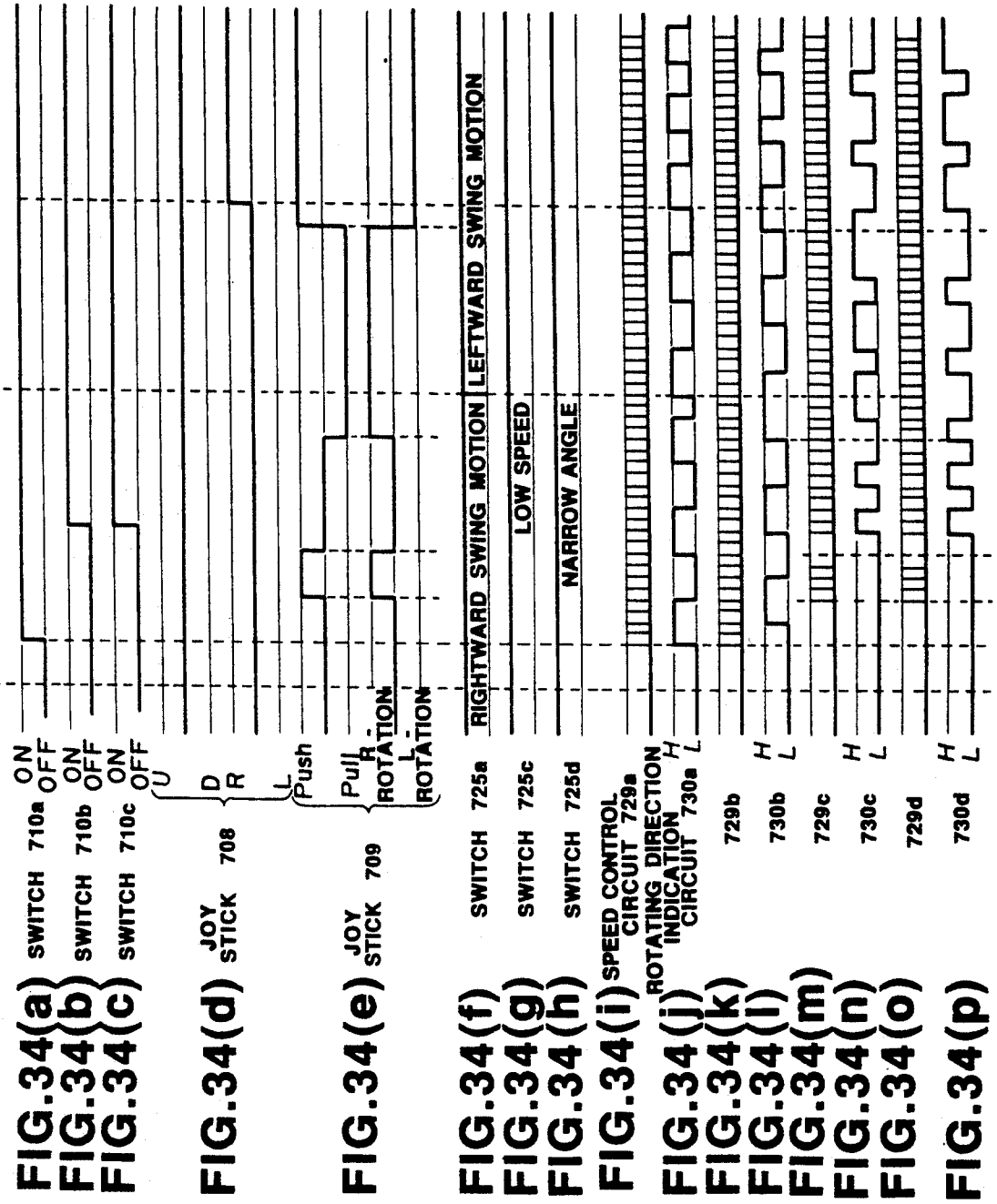

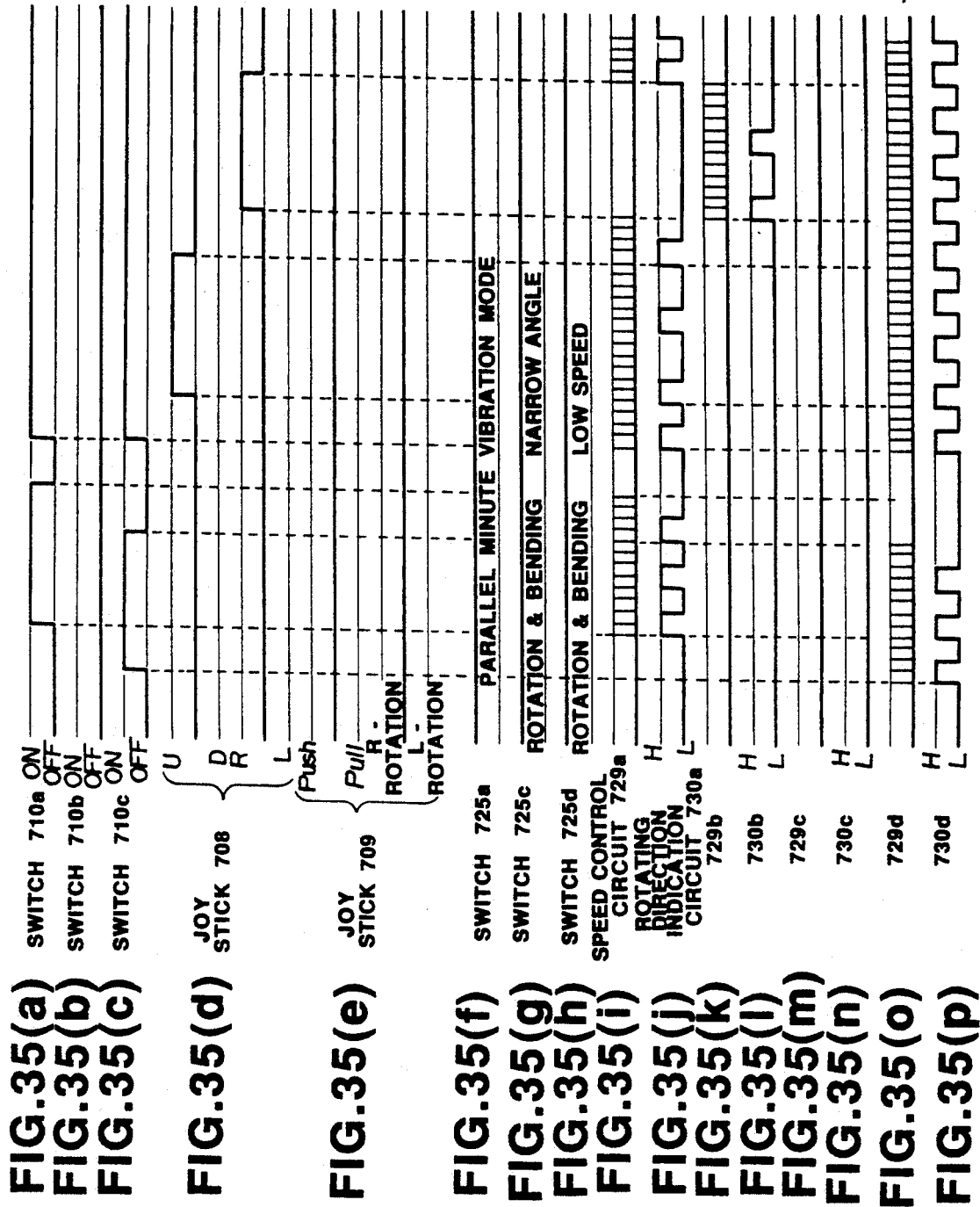

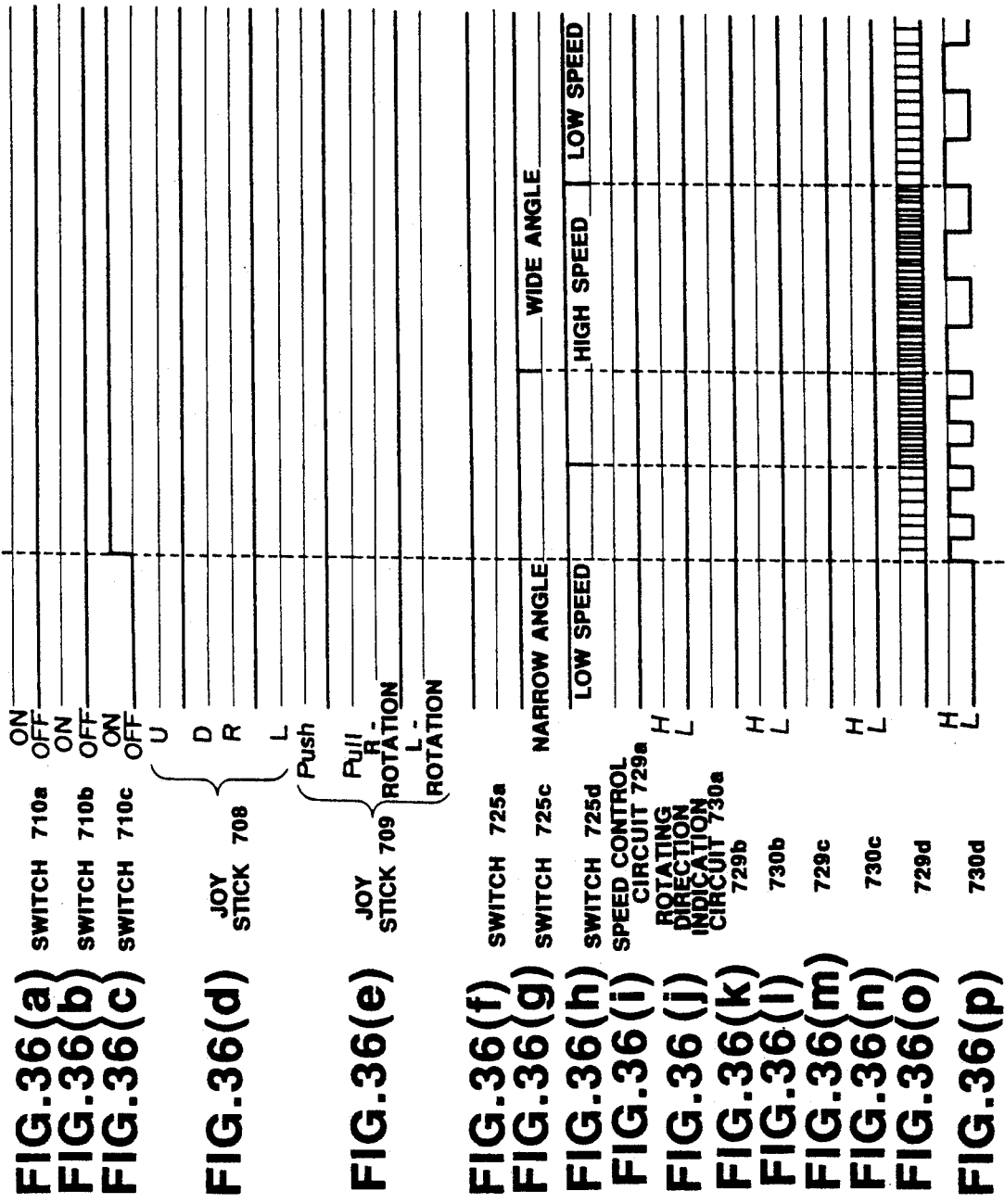

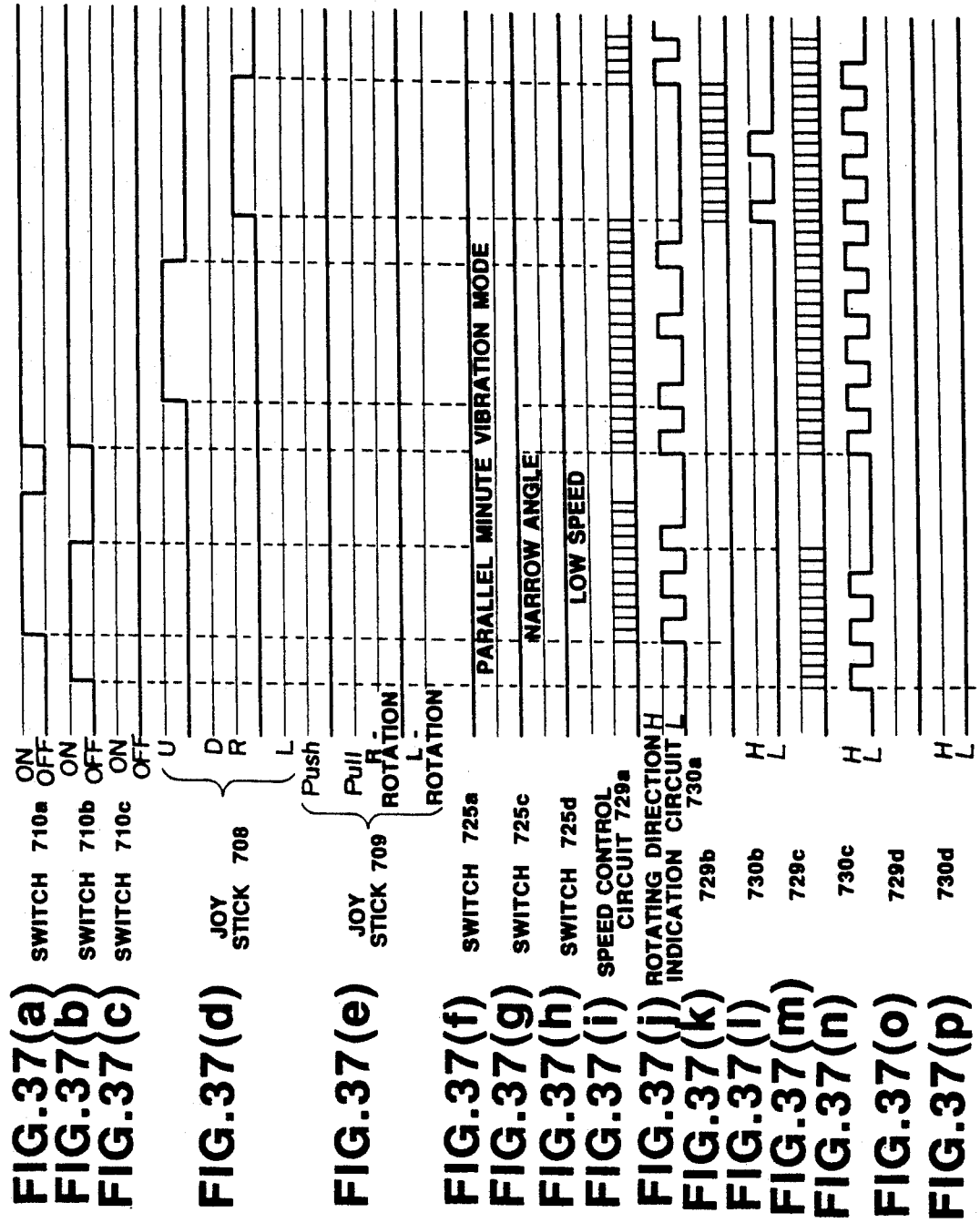

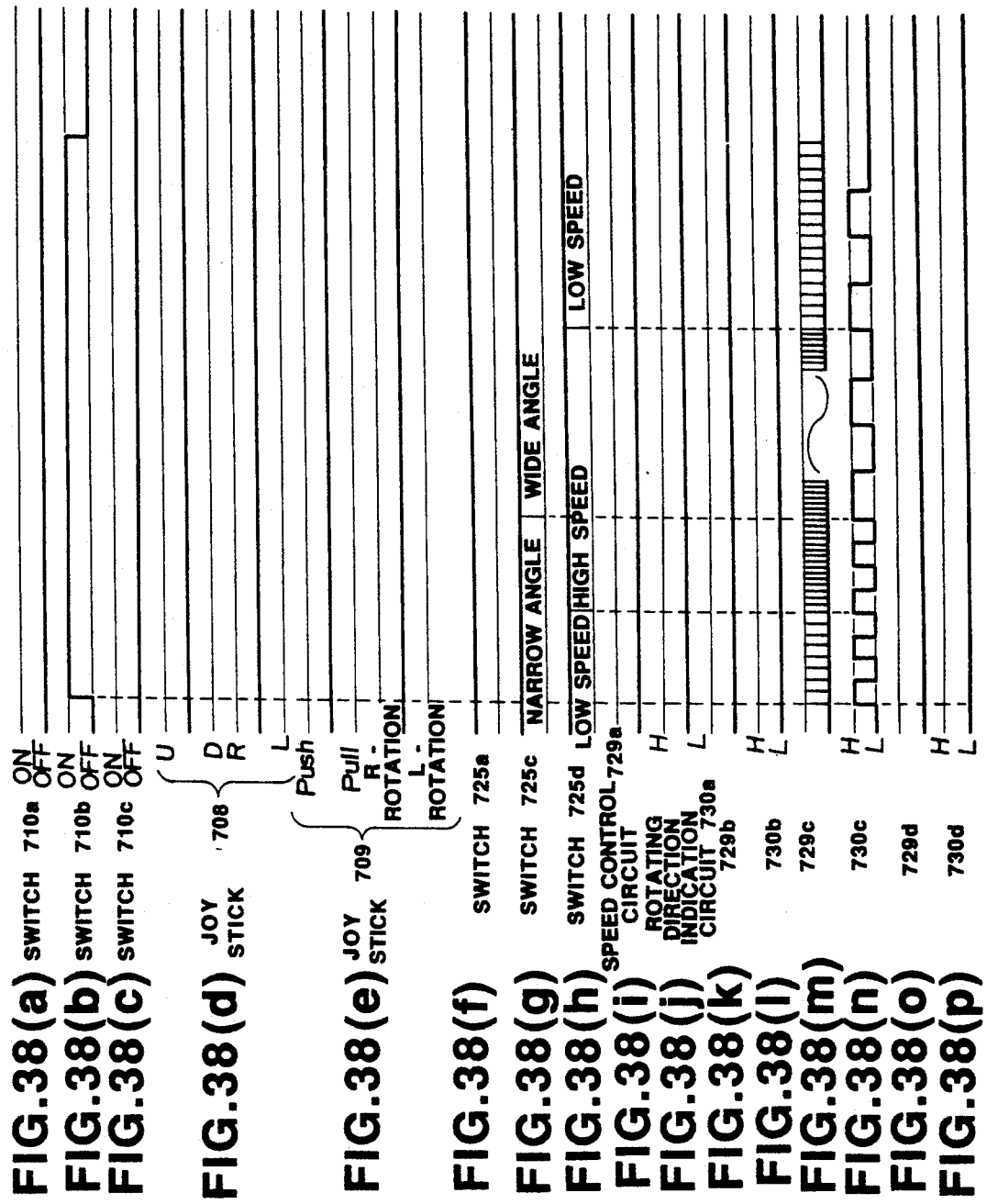

702

702

702

702

702

702

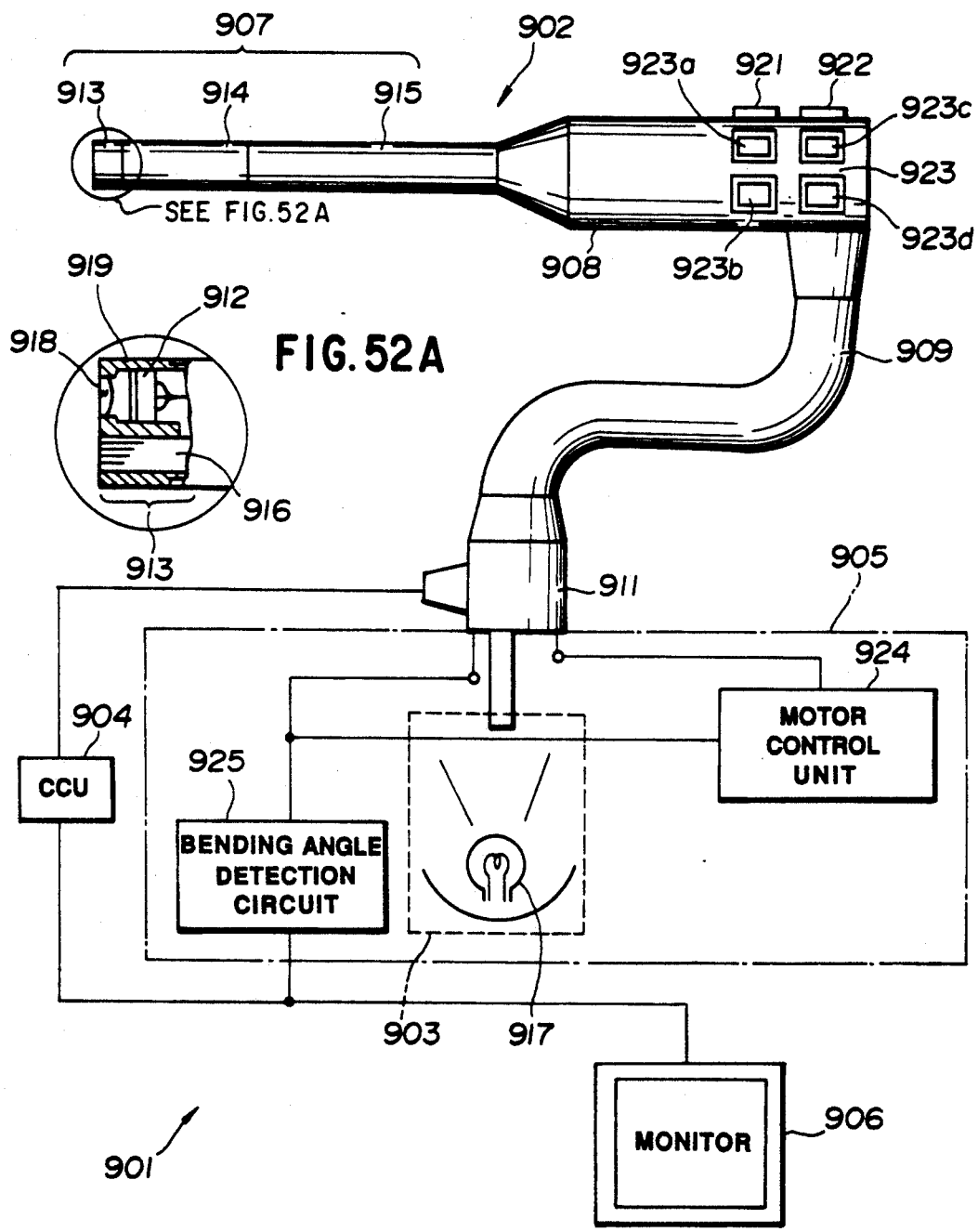

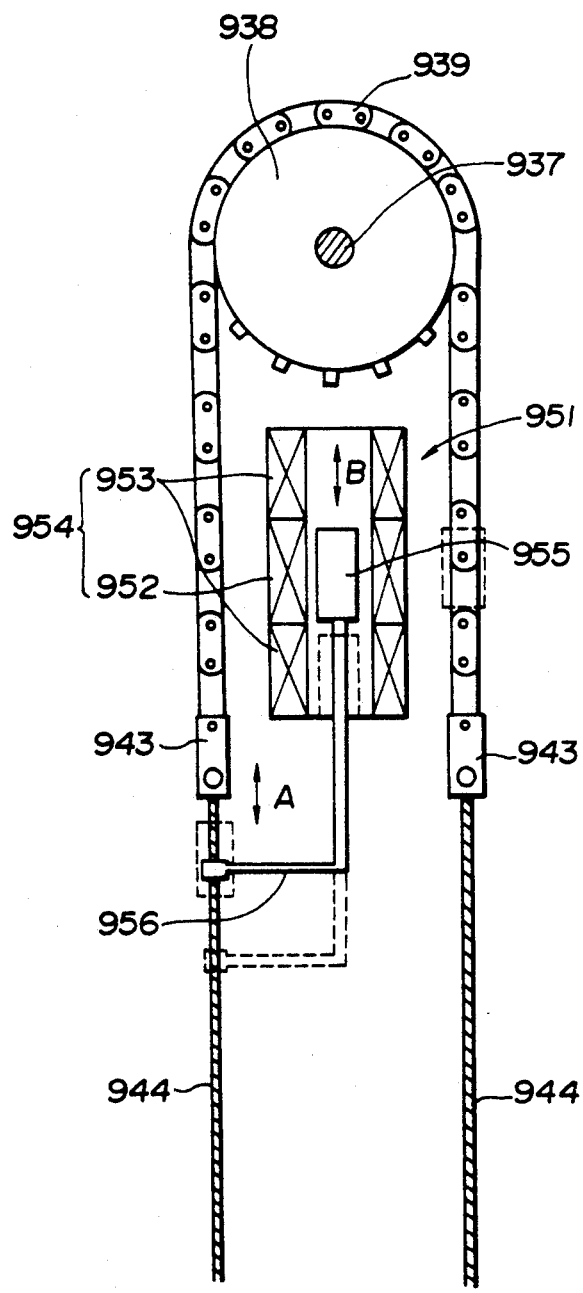
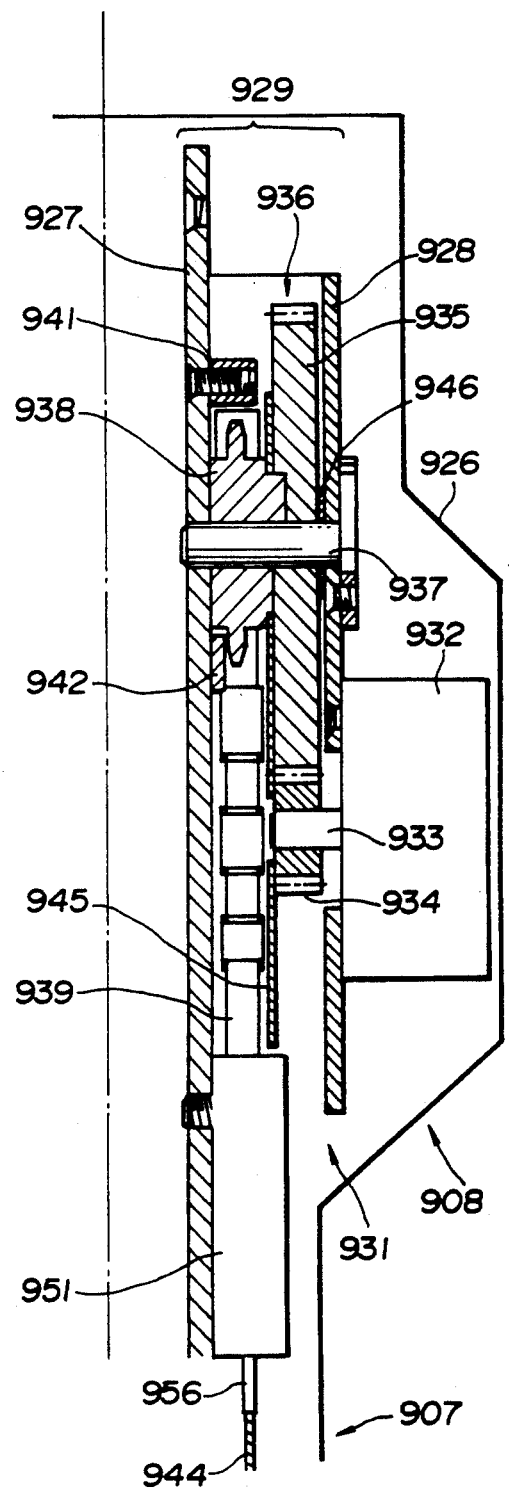

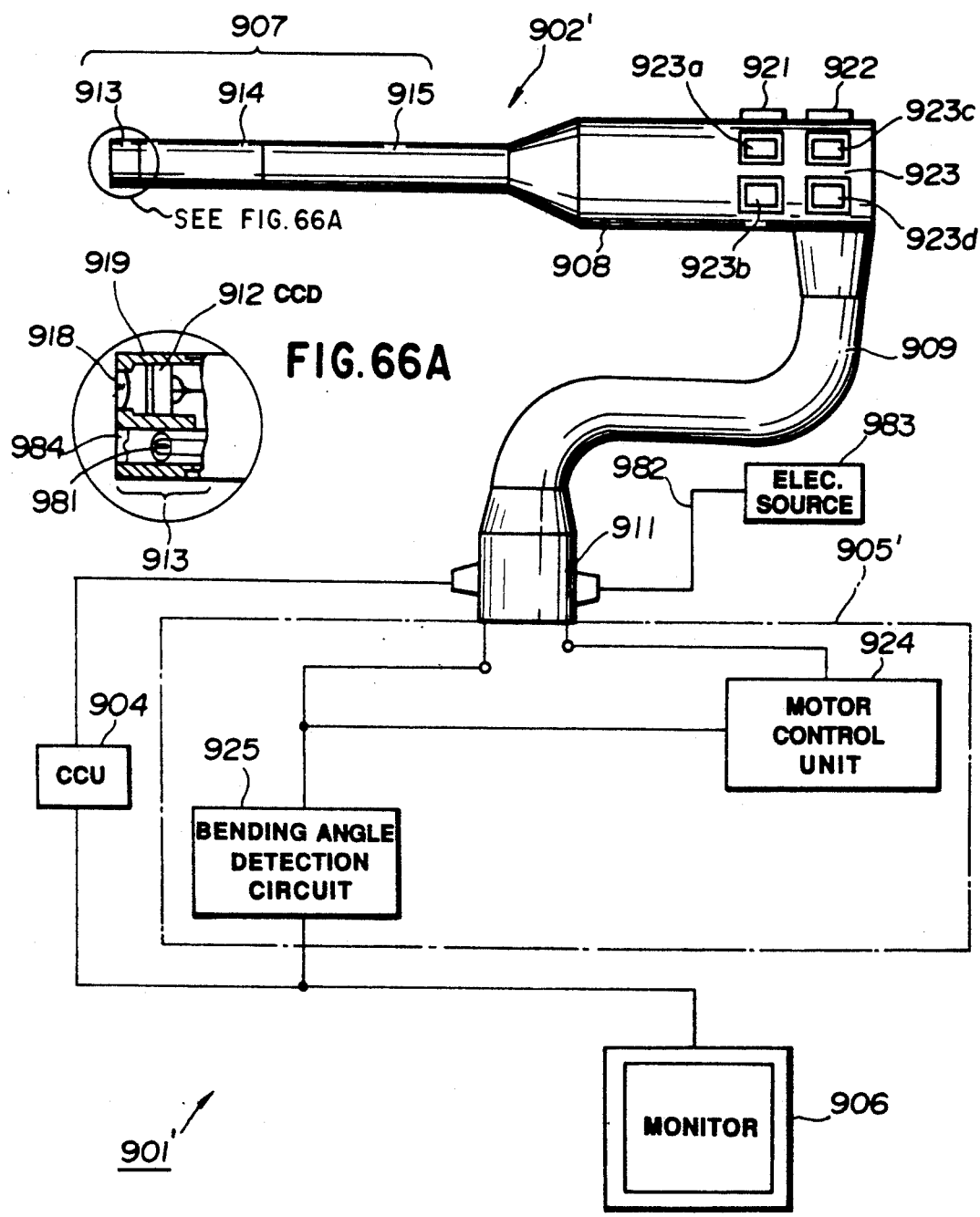

ELECTRONIC ENDOSCOPE SYSTEM PROVIDED WITH A SEPARATE CAMERA CONTROLLING UNIT AND MOTOR CONTROLLING UNIT

BACKGROUND OF THE INVENTION

Field of the Invention and Detailed Description of the Related Art

This invention relates to an electronic endoscope system wherein a camera controlling unit processing video signals for an imaging device and a motor controlling unit driving and controlling a bending driving motor or the like are made separate bodies.

Recently, there is extensively utilized an endoscope whereby organs within a body cavity can be observed by inserting an elongate insert section into a body cavity and various therapeutic treatments can be made by using a treating instrument inserted through a treating instrument channel as required.

The above mentioned endoscope is provided on the distal end side of the insert section with a bendable portion so as to be controllable by a bending means on the hand base side and to be insertable into a bent body cavity or the like.

As shown in the publication, for example, of Japanese Patent Application Laid Open No. 26042/1987, in a means for operating the above mentioned bendable portion, a bending operation knob is provided in an operating section so that, when this bending operation knob is rotated and operated, one of a pair of bending wires will be pulled but the other will be relaxed so as to be able to bend the bendable portion so that the pulled side may be inside. In the case of pulling/relaxing a pair of wires manually as in this prior art example, a considerable power will be required. Therefore, there is an electrically operated endoscope wherein such bending driving means as an electric motor is provided so that, when it is switched on/off by a switch or the like, the motor will be controlled to rotate/stop to be able to bend and control the bendable portion.

Recently, instead of a fiber scope transmitting an optical image through an image guide, there is also used an electronic endoscope (electronic scope) wherein such solid state imaging device as a charge coupled device (CCD) is arranged in the image forming position of an objective lens. In the case of observing with this electronic endoscope, it will be used as an electronic endoscope system wherein an image signal made by photoelectrically converting an optical image with a solid state imaging device is transmitted to a signal processing means through a signal cable and a video signal obtained by processing the signal by the signal processing means can be displayed in a monitor. Also, in this electronic endoscope system, instead of using the electronic endoscope, there may be used a TV camera externally fitted scope fitted with a TV camera in the eyepiece portion of a fiber scope.

The above mentioned endoscope system has an advantage that an image can be more easily recorded, reproduced and sought than by an optical endoscope system and is to be used extensively in the future.

For example, in U.S. Pat. No. 4,621,618 there is disclosed a system in which a bending motor control unit (abbreviated as a bending MCU hereinafter), camera control unit (abbreviated as a CCU hereinafter), light source apparatus and monitor are made integral. Also, in U.S. Pat. 4,941,456 there is disclosed a system in which a bending MCU and CCU are made integral and a monitor is separate.

Either of the above mentioned two U.S. patents in which the bending MCU and CCU are made integral can be used in the endoscope exclusively for its system but can not be substantially used by using the existing electronic endoscope. Also, the TV camera externally fitted scope in which the fiber scope connector and TV camera connector are separate from each other can not be used.

Generally, an (electronic) endoscope proper for the uses is selected and used and is therefore desirable to be of a system which can be used by replacing only the (electronic) endoscope. There is also a defect that it is not interchangeable with the existing (electronic) endoscope and can not be used for a new (electronic) endoscope made by improving the existing one.

OBJECTS AND SUMMARY OF THE INVENTION

An object of the present invention is to provide an electronic endoscope system which can be easily formed by replacing only the endoscope.

Another object of the present invention is to provide an electronic endoscope system for which either an electronic scope or TV camera externally fitted scope can be used.

Another object of the present invention is to provide an electronic endoscope system which can be easily expanded.

In the present invention, an electronic endoscope system comprises:

an electronic endoscope provided with an elongate flexible insert section, an illuminating light emitting means for transmitting an illuminating light fed from outside and emitting it from an illuminating window in the distal end component of the above mentioned insert section, an objective optical system provided in the distal end component of the above mentioned insert section, an imaging means for photoelectrically converting an optical image based on the above mentioned objective optical system and a first connector connected to a cable connected with the above mentioned imaging means;

an electric operating means for electrically making at least one of an operation of bending a bendable portion provided in the above mentioned insert section, an operation of the advancing and retreating movement of the above mentioned insert portion in the axial direction of the above mentioned insert portion and an operation of rotating the above mentioned insert portion around the axial direction of the above mentioned insert portion;

a second connector connected to a cable connected with the above mentioned electric operating means and formed as separated from the above mentioned first connector; first connector receptacle which can connect the above mentioned first connector, processing a signal for the above mentioned imaging means and producing a video signal;

a means for electrically driving in response to the operation of the above mentioned electric operating means at least one of a bending driving means for bending and driving the above mentioned bendable portion, an advancing and retreating driving means for advancing and retreating moving the above mentioned insert portion in the axial direction of the above mentioned insert portion and a rotating driving means for rotating driving the above mentioned insert section around the axial direction of the above mentioned insert section;

a controlling unit formed separately from the above mentioned video signal processing unit, provided with a second connector receptacle which can connect the above mentioned second connector and controlling the above mentioned electrically driving means in response to the operation of the above mentioned electrically operating means;

a light source apparatus provided with a connector receptacle which can connect the connector of the above mentioned illuminating light emitting means and feeding the above mentioned illuminating light; and a monitor means for displaying the above mentioned video signal;

so that either of an existing electronic scope and a TV camera externally fitted scope may be used.

BRIEF DESCRIPTION OF THE DRAWINGS

FIGS. 1 to 5 relate to the first embodiment of the present invention.

FIG. 1 is a general formation diagram of an electronic endoscope system of the first embodiment.

FIG. 2 is an explanatory diagram showing as sectioned the electronic endoscope system of the first embodiment.

FIG. 3 is a perspective view of the electronic endoscope system of the first embodiment.

FIG. 4 is a block diagram showing the formation of a camera controlling unit.

FIG. 5 is a formation view of a TV camera externally fitted scope which can be used instead of the electronic scope.

FIGS. 6 to 8 are perspective views showing a modification of the first embodiment of the present invention.

FIGS. 9 and 10 relate to the second embodiment of the present invention.

FIG. 9 is a perspective view showing the appearance of an endoscope system of the second embodiment.

FIG. 10 is a general formation diagram of the endoscope system.

FIG. 11 is a perspective view showing the appearance of a modification of the second embodiment.

FIG. 12 is a perspective view showing the appearance of an endoscope system of the third embodiment.

FIG. 13 is a block diagram for explaining the functional formation of the endoscope system.

FIG. 14 is a flow chart showing the control of a freezing and releasing function.

FIG. 15 is a flow chart showing the control of a moving picture display of a sub-screen at the time of freezing and releasing.

FIG. 16 is an explanatory view for explaining the imaging of a panorama image.

FIG. 17 is a flow chart showing the control of the display of a panorama picture.

FIGS. 18 to 22 are perspective views showing respective modifications of the third embodiment.

FIG. 24 is a formation diagram showing a scheme of an endoscope system of the fifth embodiment.

FIG. 25 is a block diagram showing a general formation of the endoscope system.

FIGS. 27 to 47 relate to the seventh embodiment of the present invention.

FIG. 27 is a block diagram showing a formation of an endoscope system.

FIG. 28 is an explanatory view showing the appearance of the endoscope system.

FIG. 29 is a block diagram showing the formation of a bending, advance, retreat and rotation controlling circuit.

FIGS. 30a-30n are timing charts for explaining the operation of the endoscope system at the time of an ordinary bending operation.

FIGS. 31a-31p are timing charts for explaining the operation of the endoscope system at the time of a non-bending operation in a minute vibration mode in the same direction.

FIGS. 32a-32p are timing charts for explaining the operation of the endoscope system at the time of a bending operation in a minute vibration mode in the same direction.

FIGS. 33a-33p are timing charts for explaining the operation of the endoscope system in a minute vibration mode in the right angle direction.

FIGS. 34a-33p are timing charts for explaining the operation of the endoscope system at the time of a rotating motion.

FIGS. 35a-35p are timing charts for explaining the operation of the endoscope system at the time of the operation of a rotating minute vibration and bending minute vibration.

FIGS. 36a-36p are timing charts for explaining the operation of the endoscope system at the time when the conditions of the rotating, minute vibration are changed.

FIGS. 37a-37p are timing charts for explaining the operation of the endoscope system at the time of the operation of an advancing and retreating minute vibration and bending minute vibration.

FIGS. 38a-38p are timing charts for explaining the operation of the endoscope system at the time when the conditions of the advancing and retreating minute vibration are changed.

FIG. 39 is an explanatory view showing a minute vibration in the vertical direction.

FIG. 40 is an explanatory view showing a minute vibration in the horizontal direction.

FIG. 41 is an explanatory view showing a rightward swing motion.

FIG. 42 is an explanatory view showing a leftward swing motion.

FIG. 43 is an explanatory view showing an advancing and retreating minute vibration.

FIG. 44 is an explanatory view showing a rotating minute vibration.

FIG. 45 is an explanatory view showing a part of a mode displaying part of a monitor.

FIGS. 46 and 47 relate to the eighth embodiment of the present invention.

FIG. 46 is a block diagram showing the formation of an endoscope system of the eighth embodiment.

FIG. 47 is an explanatory view showing the appearance of the endoscope system.

FIG. 48 is an explanatory diagram showing a schematic formation of an endoscope system of the ninth embodiment.

FIG. 49 is an explanatory view showing the appearance of the endoscope system.

FIG. 50 is an explanatory diagram showing a schematic formation of an endoscope system of the modification the ninth embodiment.

FIG. 51 is an explanatory view showing the appearance of the endoscope system.

FIGS. 52 to 54 relate to the tenth embodiment of the present invention.

FIG. 52 is a general formation diagram of the tenth embodiment.

FIG. 53 is a sectioned view showing the structure of a bending operation apparatus provided within an operating section.

FIG. 54 is an elevation showing a differential transformer as arranged in a space part formed by a sprocket and chain within the operating section.

FIG. 56 is an explanatory diagram showing the whole of an endoscope system.

FIG. 57 is a half-sectioned view of a motor unit.

FIGS. 59 to 63 relate to the fourteenth embodiment of the present invention.

FIG. 59 is a block diagram showing the formation of an endoscope system.

FIG. 60 is a side view of a driving apparatus.

FIG. 61 is a side view of a distal end component.

FIG. 62 is a perspective view of an extending base part.

FIG. 63 is an explanatory view of the operating section as held.

FIG. 64 is a block diagram showing the formation of an endoscope system.

FIG. 65 is a side view of a driving apparatus.

FIG. 66 is a general formation diagram of the sixteenth embodiment of the present invention.

FIGS. 67 and 68 relate to the seventeenth embodiment of the present invention.

FIG. 67 is a perspective view of an endoscope system of the seventeenth embodiment.

DETAILED DESCRIPTION OF THE PREFERRED EMBODIMENTS

Figure 1:
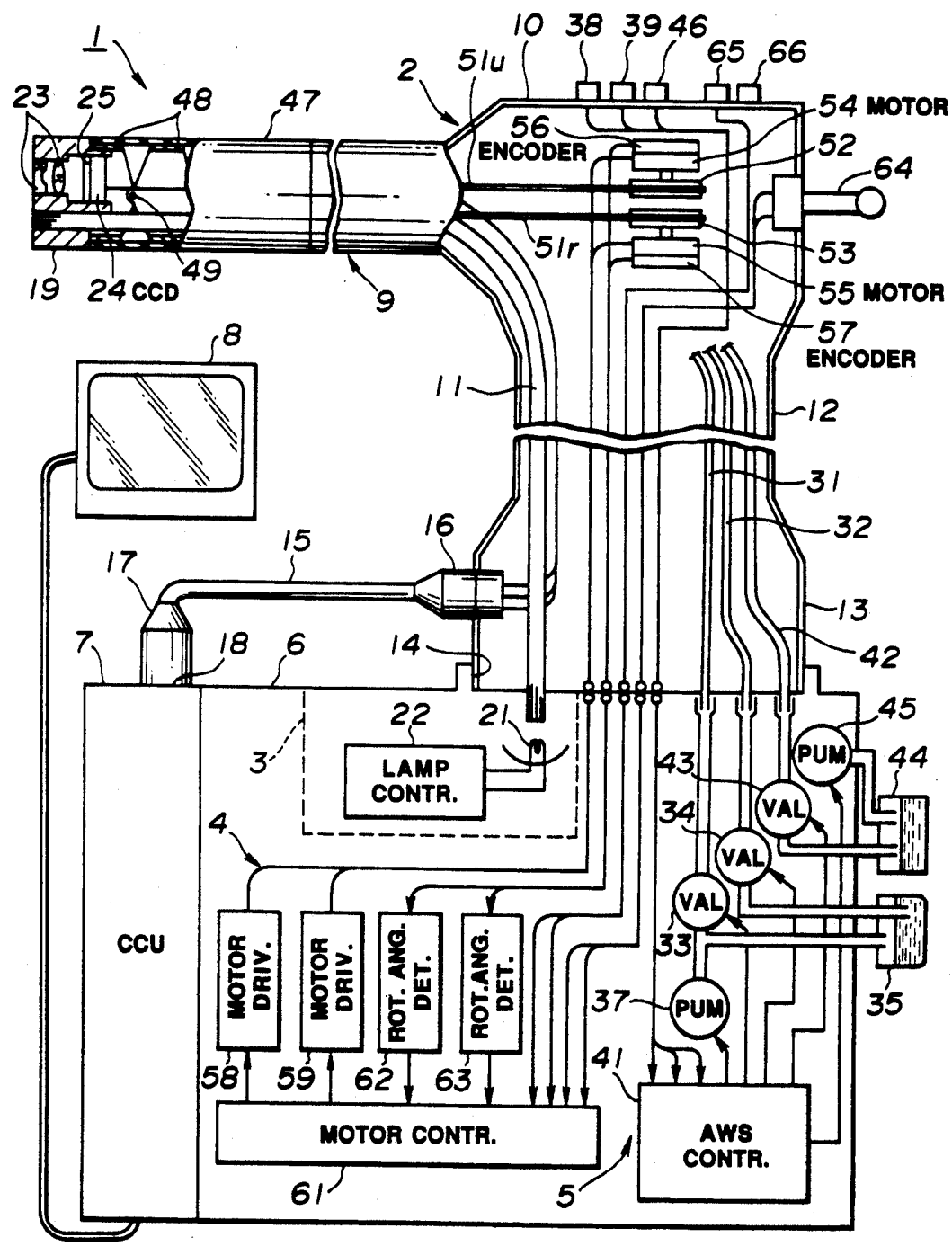
Figure 3:
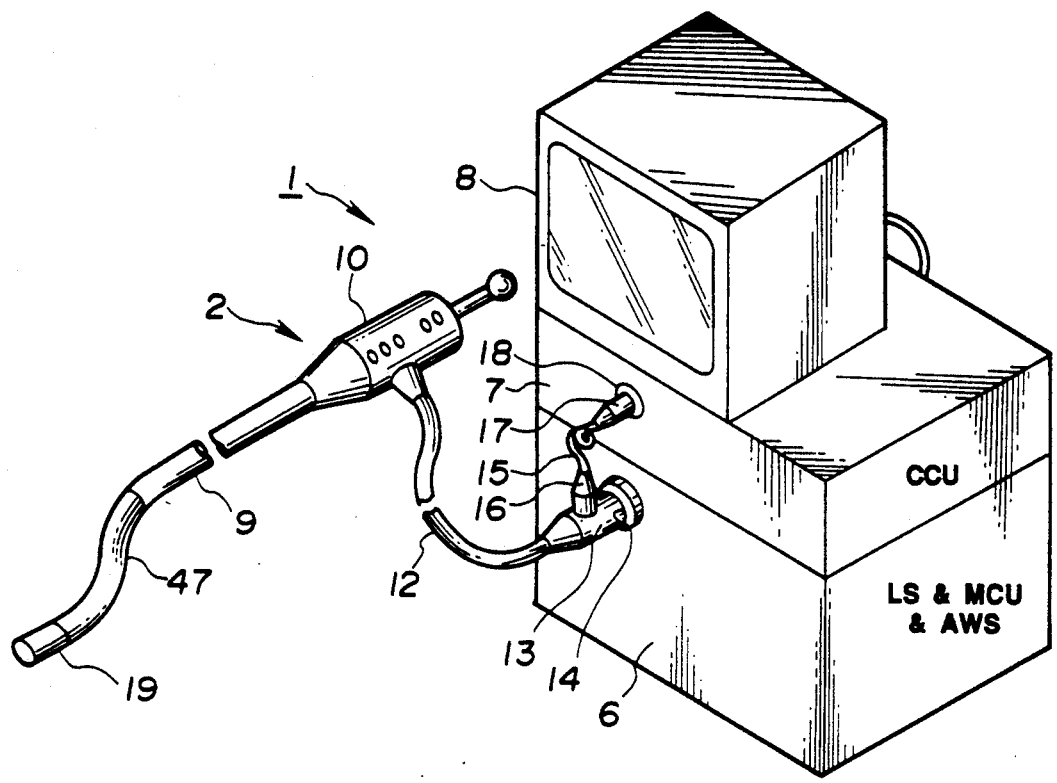

As shown in FIG. 1 or 3, an electronic endoscope system 1 of the first embodiment comprises an electronic scope 2 having an imaging means built-in, a light source & MCU & AWS 6 having a light source apparatus 3 feeding an illuminating light to this electronic scope 2, a motor control unit (abbreviated as an MCU hereinafter) 4 and an air-feed/water-feed and suction controlling apparatus (abbreviated as an AWS hereinafter) 5 built-in, a camera controlling unit (abbreviated as a CCU or mentioned also as a video processor) 7 separate from this light source & MCU & AWS 6 and processing a video signal for the above mentioned imaging means and a monitor 8 color-displaying the video signal output from this CCU 7.

The above mentioned electronic scope 2 has a flexible elongate insert section 9 and a thick operating section 10 formed at the rear end (base end) of this insert section 9. A light guide 11 for transmitting an illuminating light is inserted through the above mentioned insert section 9 and is further inserted through a universal cord 12 extended out of an operating section 10 and a connector 13 at the end of this universal cord 12 can be fitted to a connector receptacle 14 of the light source & MCU & AWS 6. A connector 16 provided at one end of a signal cable 15 is connected to the connector 13 on the side and a connector 17 provided at the other end can be connected to a connector receptacle 18 of the CCU 7.

When the above mentioned connector 13 is connected to the connector receptacle 14 of the light source & MCU & AWS 6, the illuminating light of the light source 3 will be fed to one end surface to be an entrance side of the light guide 13, will be transmitted through this light guide 13 and will be emitted forward from the other end surface fixed to the distal end component 19 of the insert section to illuminate a forward object to be imaged. The above mentioned light source apparatus 3 comprises a lamp 21 and a lamp controlling circuit 22 for controlling the emitted light amount of this lamp 21.

Figure 4:
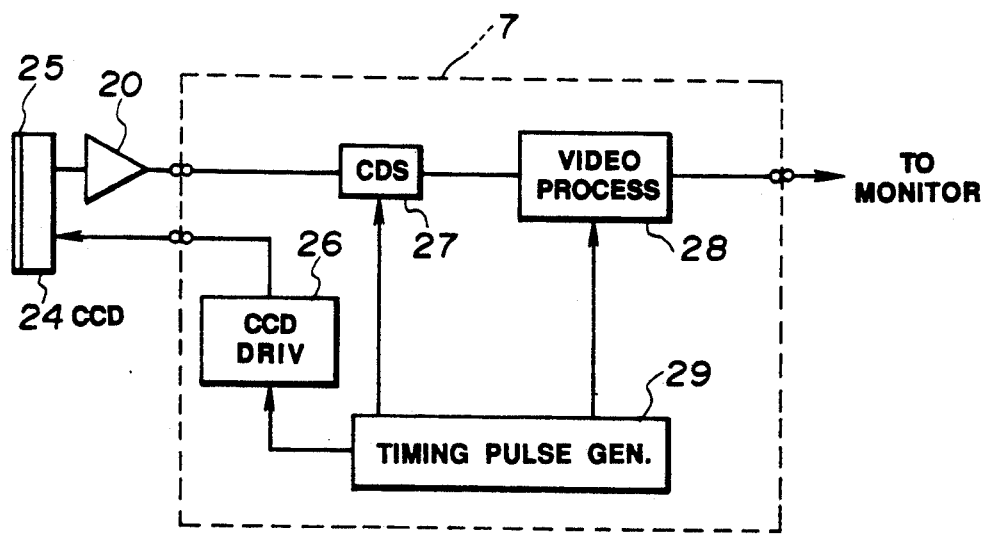

An optical image of the object illuminated by the illuminating light emitted from the end surface on the distal end side of the above mentioned insert section 9 will be formed on the light receiving surface (photoelectrically converting surface) of a CCD 24 arranged in the focal plane by an objective lens 23 fitted to the distal end component 19. Such color separating filter as a mosaic filter 25 is fitted to the front surface of this CCD 24 to color-separate respective pixels. The signal photoelectrically converted by this CCD 24 is accumulated as an electric charge, is read out by the application of a driving signal output from a CCD driving circuit 26 within the CCU 7 as shown in FIG. 4, is amplified by a preamplifier 20, for example, within the electronic scope 2, is then input into a correlated double sampling (CDS) circuit 27 within the CCU 7, has a resetting noise or the like removed and is further signal-processed in a video processing circuit 28 (this circuit 28 is mentioned, for example, in U.S. Pat. No. 4,884,134) to produce an NTSC signal and an object image is color-displayed in the monitor 8. The respective circuits are controlled by a timing pulse generator 29.

An air feeding tube 31 and water feeding tube 32 for feeding air and water are inserted through the above mentioned insert section 9 and are further inserted through the universal cord 14 and will be connected with an air and water feeding tank 35 respectively through valves 33 and 34 when the connector 13 is connected to the connector receptacle 14 of the light source & MCU & AWS 6.

The above mentioned air and water feeding tank 35 is connected to the valve 33 and pump 37 through a tube. The operating section is provided with an air feeding switch 38 and water feeding switch 39 for feeding respectively air and water. The signals of these air feeding and water feeding switches 38 and 39 are input into an AWS controlling circuit 41.

Figure 2:
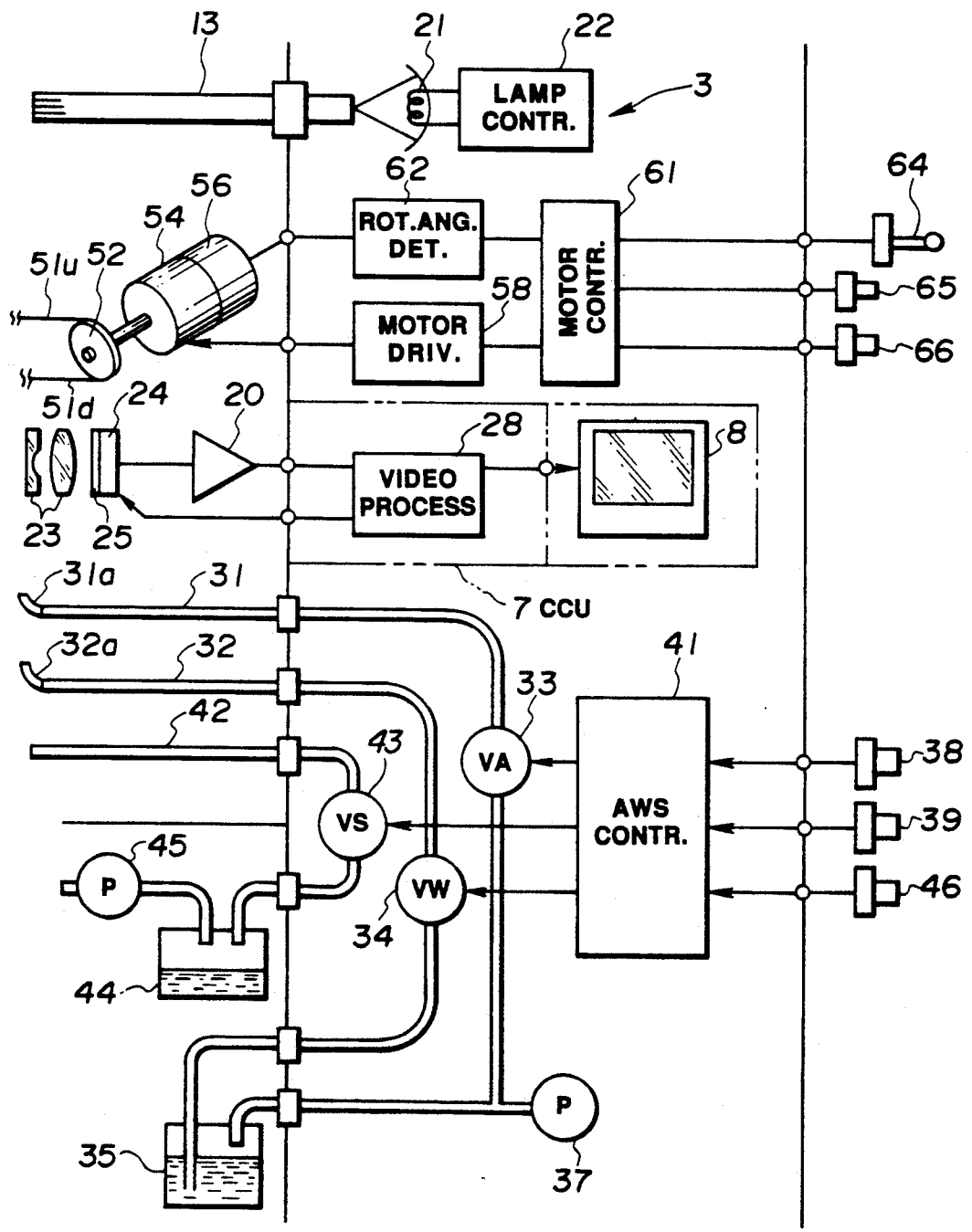

When the air feeding switch 38 is operated, this AWS controlling circuit 41 will open the valve 33 and will operate the pump 37 to pressurize the tank 39 and deliver air through the air feeding tube 31. Also, when the water feeding switch 39 is operated, this AWS controlling circuit 41 will open the valve 34 and operate the pump 37 to pressurize the tank 39 and deliver water through the water delivering tube 32. As shown in FIG. 2, nozzles 31a and 32a are formed respectively at the tips of the air feeding tube 31 and water feeding tube 32 so that the fed air and water may be jetted onto the outer surface of the opposed objective lens 23 respectively through the nozzles 31a and 32a, the mucus or the like deposited on the outer surface of this objective lens 23 may be blown or washed away to set a visual field desirable for the observation.

Further, a suction tube 42 for suction is inserted through the insert section 9 and is further inserted through the universal cord 12 and will be connected through a valve 43 with a suction pump 45 fitted through a drainage tank 44 when the connector 13 is connected to the connector receptacle 14 of the light source & MCU & AWS 6.

The above mentioned valve 43 and suction pump 45 are switched on/off by operating a suction switch 46 so that the body liquid or the like obstructing the observation of the body interior may be drained by suction into the drainage tank 44.

A bendable portion 47 is formed adjacently to the distal end component 19 in the above mentioned insert section and consists of many articulate frames 48 rotatably connected in tandem with each other bY connecting parts 49 in the axial direction of the insert section 9 Further, respective pairs of wires 51u and 51d and wires 51r and 51l for the bending operation are fixed at one end in respective vertical and horizontal positions in the foremost end articulate frame 48 and at the other end to pulleys 52 and 53 within the operating section 12.(Only the wires 51u and 51r on one side are shown in FIG. 1 and only one pair of the wires 51u and 51d are shown in FIG. 2.)

The above mentioned respective pulleys 52 and 53 are connected respectively to the rotary shafts of a vertically bending motor 54 and horizontally bending motor 55 and the rotation amounts of the respective motors 54 and 55 can be detected respectively by a vertically bending angle detecting encoder 56 and a horizontally bending angle detecting encoder 57. The respective motors 54 and 55 are rotated and driven by motor driving signals respectively from motor driving circuits 58 and 59.

The output signals of the encoders 56 and 57 are input respectively into rotation angle detecting circuits 62 and 63, the rotation angles of respective motors 54 and 55 are detected and are output to a motor controlling circuit 61.

Further, the above mentioned operating section 10 is provided with a joystick 64 for vertically and horizontally bending a bendable portion 47, a straight switch 65 for straightening the bendable portion 47 and a vibration switch 66 for minutely vibrating the bendable portion 47. When the joystick 64, straight switch 65 and vibration switch 66 are operated, signals corresponding to the operations will be input into a motor controlling circuit 61 and operating states corresponding to the operations will be made under the control of this motor controlling circuit 61.

For example, if the joystick 64 is inclined upward, by the encoder built-in at the base end of this joystick 64, a signal corresponding to the upward inclination and the inclination angle will be output to the motor controlling circuit 61. When this signal is input, the motor controlling circuit 61 will rotate in the positive direction the vertically bending motor 54 through a motor driving circuit 58, the rotation angle of this motor 54 will be detected through the encoder 56 and rotation angle detecting circuit 62 and the motor 54 will be controlled to rotate until the detected rotation angle coincides with the angle by the operation of the joystick 64. When the motor 54 rotates in the positive direction, the wire 51u in the pair of the wires 51u and 51d will be wound up by the pulley 52 and will be pulled. On the other hand, the other wire 51d will be payed out of the pulley 52 and will be relaxed and therefore the bendable portion 47 will be bent upward. That is to say, when the joystick is operated to be inclined, the bendable portion 47 will be bent in the inclined direction and the bent amount of the bendable portion 47 will correspond to the inclined angle.

Also, when the straight switch 65 is operated, the motor controlling circuit 61 will control the motors 54 and 55 so that the detected angles detected by the rotating angle detecting circuits 62 and 63 just before this switch 65 is operated may be zero.

Further, when the vibration switch 66 is operated, the motor controlling circuit 61 will control the motors 54 and 55 so that driving signals vibrating to rotate the motors 54 and 55 by minute angles alternately in the positive direction and reverse direction just before this switch is operated may be fed. By this control, the bendable portion 47 will have a minute vibration further applied to the ordinary bending (also to the straight state). This slight vibration is beneficial in that, in the case of inserting into a bent part, if this minute vibration is applied, the insertion will be made more smoothly.

In the electronic endoscope apparatus 1 of this first embodiment, it is a feature that the light source & MCU & AWS 6 and the CCU 7 are made separate from each other.

Therefore, the scope which can be used in this electronic endoscope apparatus 1 is not limited to the electronic scope 2 shown in FIG. 1 but there can be used such scopes in which the connector 17 for connecting to the CCU 7 and the connector 13 for connecting to the light source & MCU & AWS 6 are separate from each other as, for example, the TV camera externally fitted scope 2C in which, as shown in FIG. 5a, the TV camera 2B is fitted to the fiber scope 2A and the TV camera externally fitted scope 2E in which, as shown in FIG. 5b, the TV camera 2B is fitted to the fiber scope 2D.

In the fiber scope 2A shown in FIG. 5a, the distal end surface of the image guide 71 is fixed in the focal plane of the objective lens 23 in the electronic scope 2 in FIG. 1 so that an optical image formed on this distal end surface will be transmitted by the image guide 71 to the end surface on the operating section 10 or eyepiece portion 72 side and will be magnified and observed through the eyepiece lens 73. In this fiber scope 2A, a cable 74 through which the light guide 11 and the like from the operating section 12 are inserted is extended out and is fitted at the end with a connector 75A for connecting the light source & MCU & AWS.

The same as in the case of the electronic scope 2, the operating section 10 is provided with the joystick 64 for bending the bendable portion by an electric operation, straight switch 65 for operating to straighten the bendable portion and vibration switch 66 for operating to minutely vibrate the bendable portion 47.

On the other hand, as shown in FIG. 5b, the fiber scope 2D is provided with a bending operation knob 76 for manually operating to bend the bendable portion 47. In this fiber scope 2D, as the bendable portion 47 is manually operated to be bent, no bending driving motor is built-in and therefore the straight switch 65 and vibration switch 66 are also not provided. This fiber scope 2D has a light source & AWS connecting connector 75B. The other same members as of the formation of the electronic scope 2 are shown by bearing the same reference numerals.

When the TV camera 2B is fitted to the eyepiece portion of the above mentioned fiber scope 2A or 2D, an optical image transmitted to the end surface on the eyepiece portion 72 side will be formed on the CCD 79 by the image forming lens 78. A mosaic filter 80 is fitted to the front surface of this CCD 79 to optically separate colors. This CCD 79 is connected with a cable 81 through which signal lines are inserted and is fitted at the end with a CCU connecting connector 82.

In the above mentioned TV camera externally fitted scope 2C, the CCU connecting connector 82 and the light source & MCU & AWS connecting connector 75A (at least the MCU connecting connector) are necessarily separate from each other. Therefore, in the apparatus of the prior art example in which the CCU and MCU are made integral with each other, as the respective CCU and MCU connecting connector receptacles provided in the apparatus are made integral with each other, the TV camera externally fitted scope 2C, which will have the same function as the electronic scope 2, can not be connected. On the other hand, in this embodiment, if the connector 13 and connector 75A are made to be of the same shape or an interchangeable structure and the connector 17 and connector 82 are made to be of the same shape or an interchangeable structure, the TV camera externally fitted scope 2C will be able to be used instead of the electronic scope 2.

Also, if the connector 13 and connector 75B are made to be of the same shape or an interchangeable structure, even the TV camera externally fitted scope 2E using the fiber scope 2d in which the bending driving motor shown in FIG. 5b is not built-in will become a system which can be used.

Also, a system can be formed by connecting the fiber scope 2A or 2D to the light source & MCU & AWS 6.

That is to say, as the CCU 7 and the light source & MCU & AWS 6 (at least MCU) are made separate from each other, the scope can be used with a component exclusively for this system 1 and can be easily used with another component replacing this component. In case an electronic scope of more pixels is to be used instead of, for example, the electronic scope 2, the signal processing system will have to be replaced but, in this case, only the CCU 7 may be replaced. On the other hand, in the prior art example, it is substantially impossible to replace only the CCU. That is to say, in the case of the expansion, this embodiment will be more advantageous than the prior art example.

The first modification of the first embodiment shall be explained with reference to FIG. 6. In this system 100, the light source & MCU & AWS 6 in the first embodiment is separated into a light source apparatus unit 101 and an MCU & AWS 6. The universal cable 12 of the electronic scope 2 is fitted with a connector 104 to be connected to a connector receptacle 103 of the light source apparatus unit 101.

On the side of this connector 104, connectors 107a and 107b fitted to the respective other ends of cables 106a and 106b connected respectively through connectors 105a and 105b can be connected respectively to the connector receptacle 18 of the CCU 7 and a connector receptacle 108 of the MCU & AWS 102.

Also, a video tape recorder (VTR) or video cassette recorder (VCR) 110a and a photographing apparatus 110b are connected respectively through cables 109a and 109b to the video output terminal of the CCU 7. The video input terminal of the CCU 7 is connected to the video output terminal of the VTR or VCR 110a through a cable 109a.

The above mentioned photographing apparatus 110b is formed of a monitor and a still camera photographing a video image displayed on the picture surface of this monitor. In this system 100, a video image displayed in the monitor 8 can be electrically recorded by the VTR or VCR 110a, the recorded video image can be reproduced in the monitor 8 and the video image can be photographed by the photographing apparatus 110b.

The other formations are the same as in the first embodiment. This first modification has substantially the same operation and effect as of the first embodiment.

Figure 7:
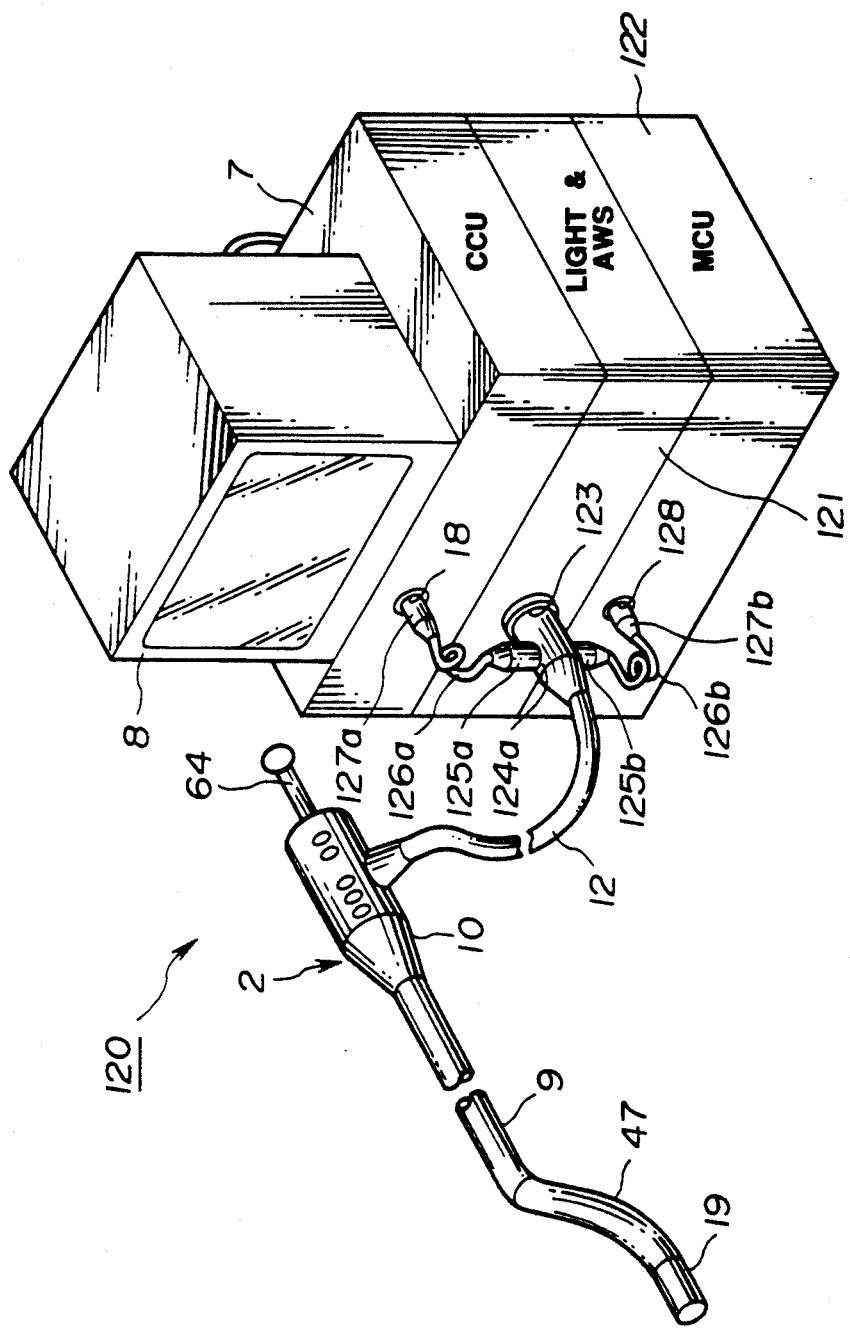

The second modification of the first embodiment shall be explained with reference to FIG. 7. In this system 120, the light source & MCU & AWS 6 in the first embodiment is separated into a light source & AWS 121 and an MCU 122. The universal cable 12 of the electronic scope 2 is fitted with a connector 124 to be connected to a connector receptacle 123 of the light source & AWS 121.

On the side of this connector 124, connectors 127a and 127b fitted to the respective other ends of cables 126a and 126b to be connected respectively through connectors 125a and 125b can be connected respectively to the connector receptacle 18 of the CCU 7 and a connector receptacle 128 of the MCU 122.

The other formations are the same as in the first embodiment. This second modification has substantially the same operation and effect as of the first embodiment.

The third modification of the first embodiment shall be explained with reference to FIG. 8. In this system 140, the MCU & AWS 102 in the first modification is further separated into an MCU 141 and AWS 142.

The connector 107b fitted to the cable 106b connected through the connector 105 with the connector 104 of the electronic scope 2 is connected to a first connector receptacle 143 of an MCU 141 provided with a second connector receptacle 144 electrically connected with a connector receptacle 145 of the AWS 142 through a cable 148 fitted at both ends with connectors 146 and 147.

On the side of the connector 13 of the electronic scope 2, an air feeding mouthpiece, water feeding mouthpiece and sucking mouthpiece are projected and can be connected respectively to an air feeding mouthpiece, water feeding mouthpiece and sucking mouthpiece of the AWS 142 respectively through an air feeding tube 151, water feeding tube 152 and sucking tube 153. The others are the same as in the first modification. This third modification has substantially the same operation and effect as in the first modification.

By the way, the connector (such as 13) of the universal cable 12 is to be connected to the apparatus including the light source apparatus but is not limited to this and may be connected to any other apparatus.

The second embodiment of the present invention shall be explained with reference to FIGS. 9 and 10. In this system 201, the air feeding/water feeding & sucking means by an electric operation in the first embodiment is made an air feeding/water feeding & sucking means by a manual operation. Therefore, the light source & MCU & AWS 6 in the first embodiment is formed of a light source & MCU 202.

The electronic scope 2 is not provided with the air feeding switch 38, water feeding switch 39 and sucking switch 46 but is provided with an air feeding/water feeding switching button 203 and a sucking button 209.

Figure 10:
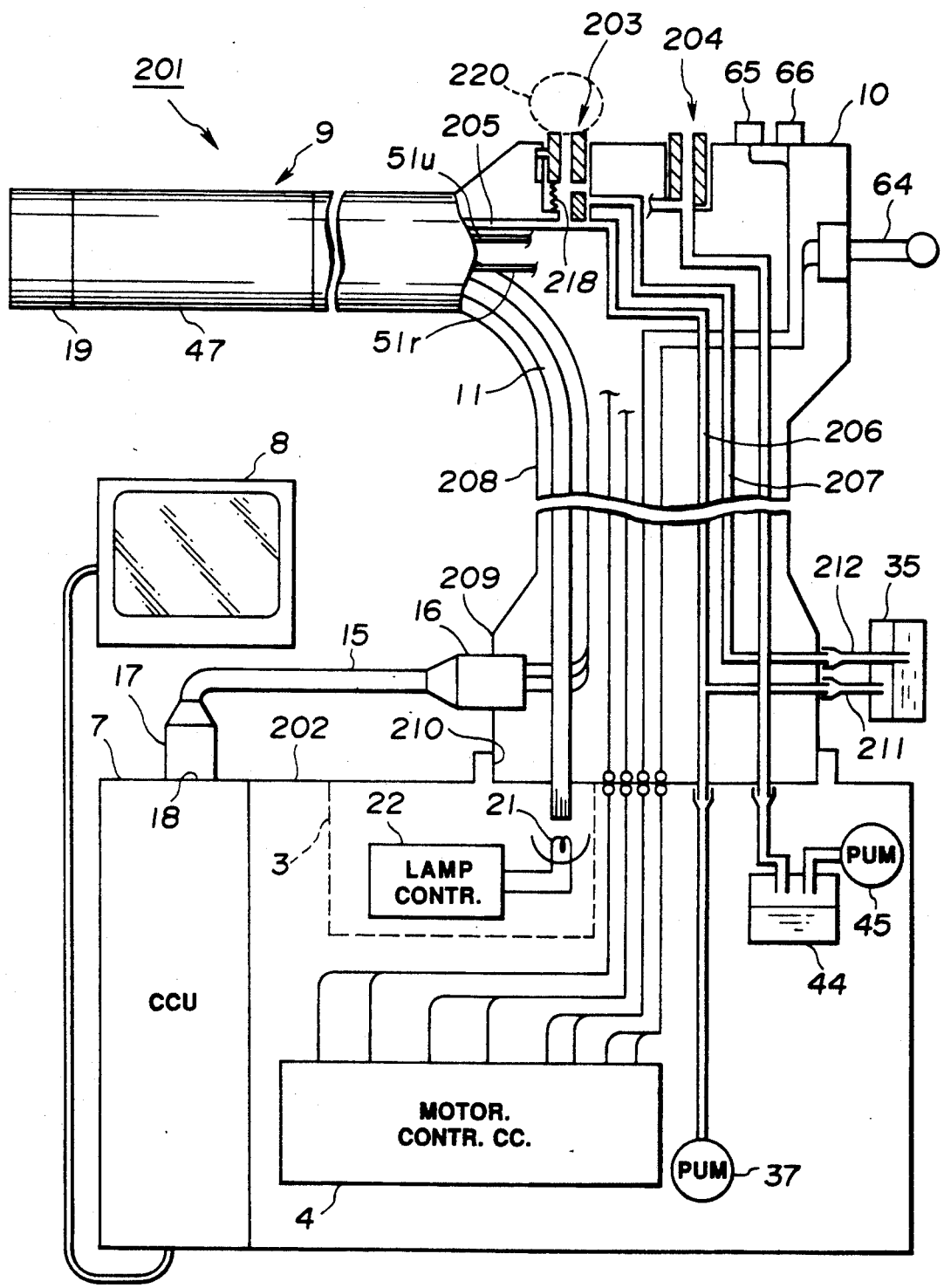

As shown in FIG. 10, an air feeding/water feeding tube 205 for feeding air or feeding water is inserted through the insert section 9 and is branched into an air feeding tube 206 and water feeding tube 207 from an air feeding/water feeding switching button 203 and the tubes lead to a connector 209 through a universal cable 208. The air feeding tube 206 is branched in a connector 209. One branch is connected to an air feeding/water feeding pump 37 within this light source & MCU 202 through a connector receptacle 210 of the light source & MCU 202. The other branch is connected to an air feeding/water feeding tank 35 through a tube 211 extended out of the connector 209. The water feeding tube 207 is also connected to this air feeding/water feeding tank 35 through a tube 212 extended out of the connector 209.

In the above mentioned air feeding/water feeding switching button 203, a cylindrical piston 217 provided with a leaking hole 216 is fitted into a cylinder 215 formed in the operating section 10 and is energized by a spring 218 so as to project at the top 215a out of the cylinder 215. This cylinder 215 normally communicates with the air feeding/water feeding tube 205 and will communicate with the air feeding tube 206 when in the illustrated state but will be interrupted from the water feeding tube 207 by the piston 217 when in the illustrated state. In the air feeding & water feeding pump 37, when the air feeding/water feeding switching button 203 is not operated normally in the operating state, air will be discharged through the leaking hole 216.

On the other hand, when the air feeding/water feeding switching button 203 is clogged with a finger 220 as shown by the dotted line, air will be fed to the air feeding/water feeding tube 205 side through the air feeding tube 206. Also, when the air feeding/water feeding switching button 203 is clogged with the finger 203 and is further pushed down against the spring 218, the piston 217 will clog the air feeding tube 206 and will make the water feeding tube 207 communicate (with the air feeding/water feeding tube 205) and water will be fed to the air feeding/water feeding tube 205 side through the water feeding tube 207.

The above mentioned sucking button 204 is provided to connect a sucking tube 221a inserted through the insert section 9 and a sucking tube 221b inserted through the universal cable 208 with each other. The sucking tube 221b is connected with the suction pump 45 through the drainage tank 44 within the light source & MCU 202. This suction pump 45 is held in a normally operating state.

In the above mentioned sucking button 204, a cylindrical piston 224 provided with a leaking hole 223 is fitted into a cylinder 222 so that, when this leaking hole 222 is clogged, air will be actually sucked from the distal end side through the sucking tube 221a though usually air is sucked from the leaking hole 222.

The other formations are the same as in the first embodiment and the operation and effect are also substantially the same as in the first embodiment.

A modification of the second embodiment shall be explained with reference to FIG. 11. In this system 250, the light source & MCU 202 in the second embodiment is made separate into a light source apparatus unit 251 and an MCU 252. The universal cable 208 of the electronic scope 2 is fitted with a connector 254 connected to a connector receptacle 253 of the light source unit 251.

On the side of this connector 254, connectors 257a and 257b fitted to the respective other ends of cables 256a and 256b connected respectively through connectors 255a and 255b can be connected respectively to the connector receptacle 18 of the CCU 7 and a connector receptacle 258 of the MCU 252.

The other formations are the same as in the second embodiment and the operation and effect are also substantially the same as in the second embodiment.

Figure 12:
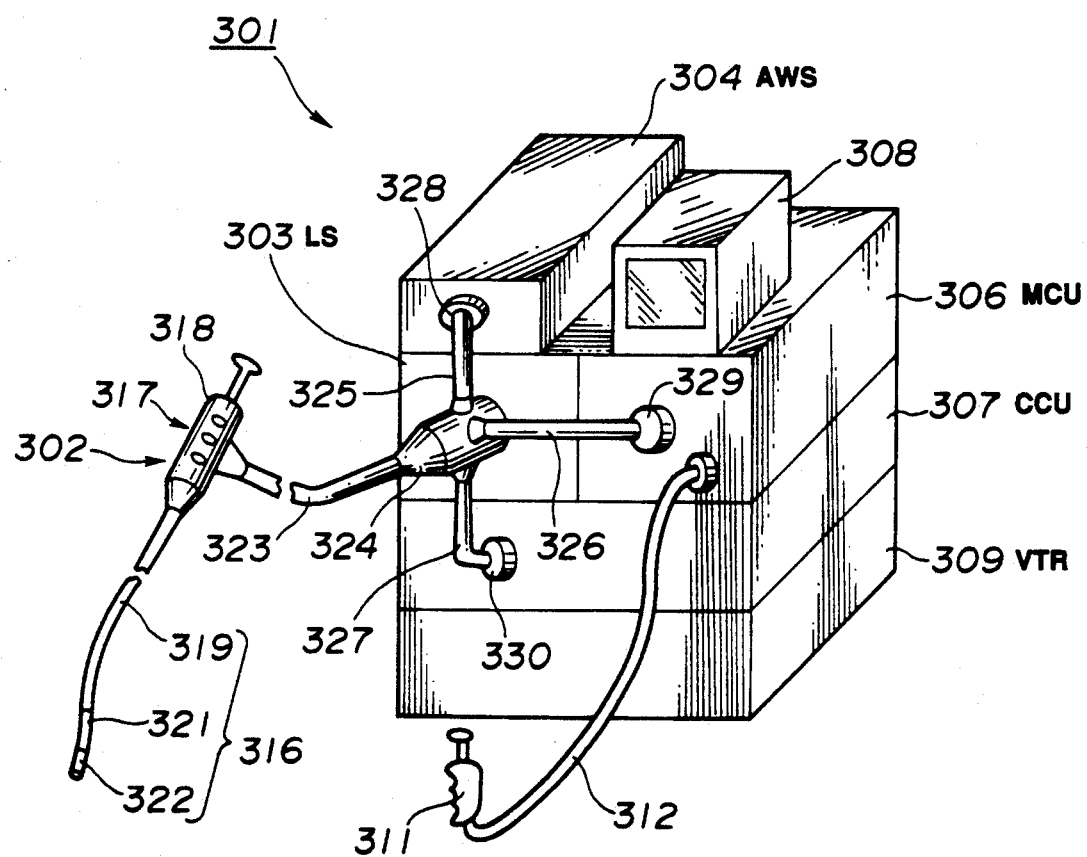
FIGS. 12 to 17 relate to the third embodiment of the present invention.

FIG. 12 shows the third embodiment of the present invention. As shown in FIG. 12, an endoscope system 301 comprises an electronic scope 302 to be inserted, for example, into a body cavity, a light source apparatus 303 for feeding an illuminating light to this electronic scope 302, an air feeding/water feeding & sucking apparatus 304 for feeding air and water to this electronic scope 302 and sucking, for example, impurities within a body cavity, an MCU 306 for driving and controlling a later described motor 354 bending and driving this electronic scope 302, a CCU 307 for processing a video signal from a solid state imaging device arranged at the distal end of this electronic scope 302 and controlling the above mentioned MCU 306, a monitor 308 displaying the video signal processed by this CCU 307 and a VTR 309 recording this video signal, a remote controlling operating section 311 remote controlling the above mentioned MCU 306 being connected to this MCU 306 through a cable 312.

The above mentioned electronic scope 302 is provided with an elongate flexible insert section 316 to be inserted into a body cavity and an operating section 318 provided at the base end of this insert section 316 and having a switching part 317 controlling predetermined operations. This insert section 316 is formed of a flexible portion 319 connected at the base end to the above mentioned operating section 318, a bending driving bendable portion 321 provided at the distal end of this flexible portion 319 and a distal end component 322 provided at the distal end of this bendable portion 321.

The above mentioned electronic scope 302 is removably connected to the above mentioned light source apparatus 303 by a connector 324 through a universal cable 323. Cables 325, 326 and 327 are extended out of this connector 324 and connectors 328, 329 and 330 fitted to the respective ends of the cables are connected, respectively, to an air feeding/water feeding and sucking apparatus 304, MCU 306 and CCU 307.

Figure 13:
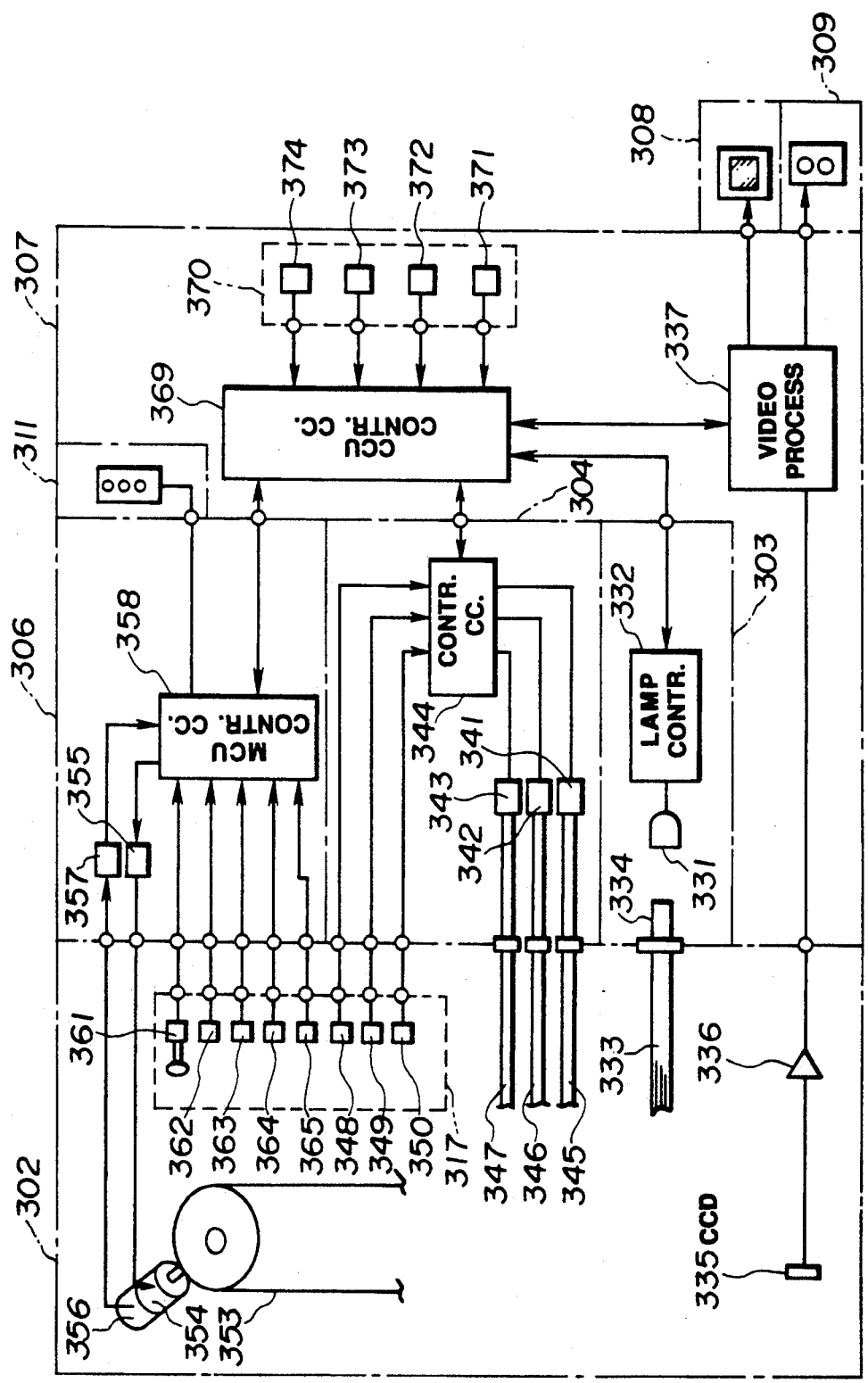
Figure 14:
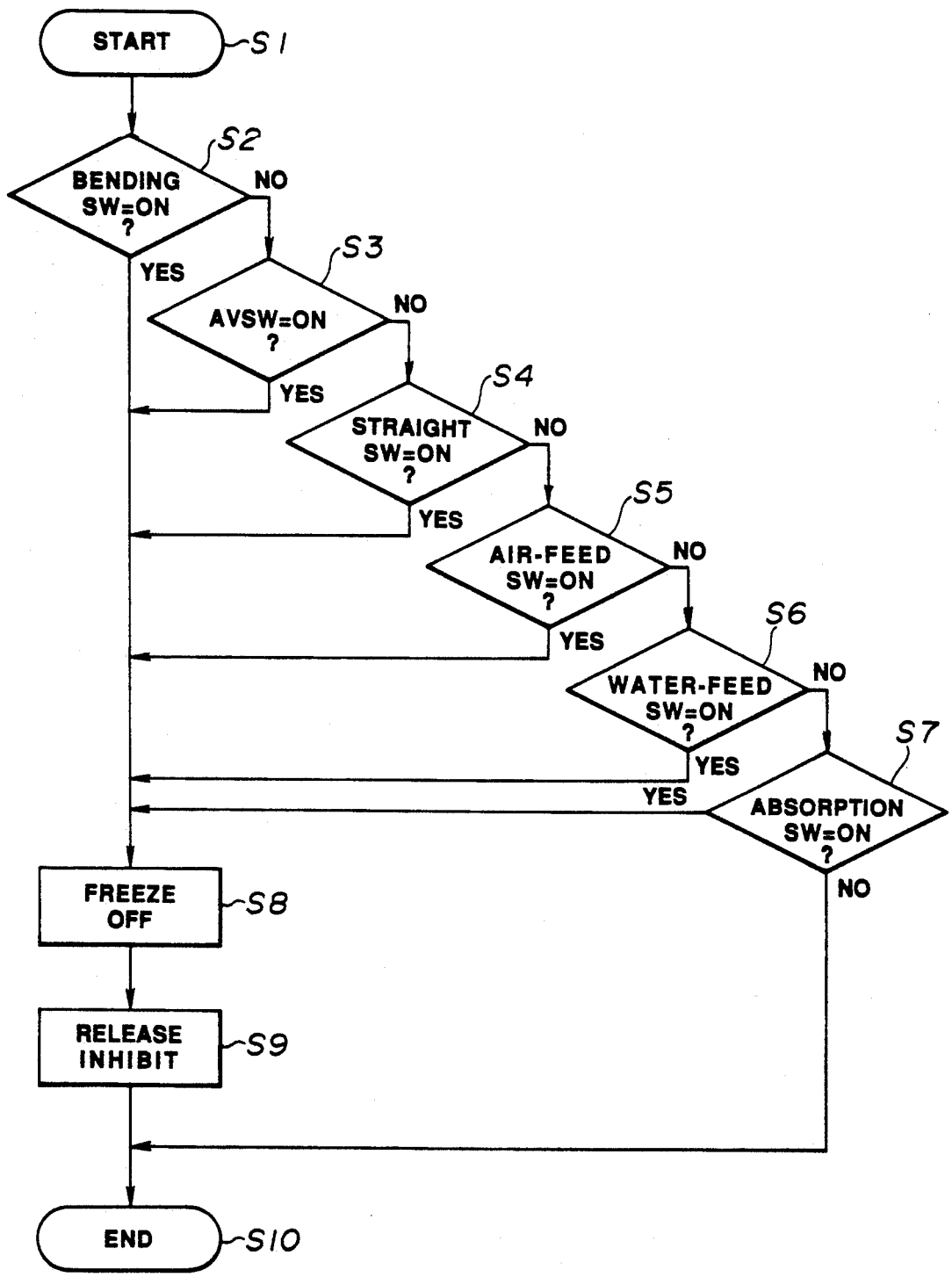

As shown in FIG. 13, the above mentioned light source apparatus 303 is provided with a light source lamp 331, a controlling circuit 332 controlling the light of this light source lamp 331 and a light guide connector receptacle 334 to be a connecting portion feeding the light from this light source lamp 331 to a light guide 333 of the electronic scope 302. The light guide 333 is inserted through the above mentioned universal cable 326 and insert section 316, transmits the illuminating light and radiates it forward of the above mentioned distal end component 322.

Within the above mentioned distal end component 322, such solid state imaging device as, for example, a simultaneous type single plate CCD 335 is arranged to image an object image radiated by a radiating light from the above mentioned light source apparatus 306.

The imaged object image is amplified by a preamplifier 336 within the above mentioned electronic scope 302 and is input into a video processing circuit 337 within the CCU 307 converting the amplified imaging signal to a video signal through a cable not illustrated inserted through the above mentioned universal cable 326. This video processing circuit 337 is to output the video signal to the above mentioned monitor 308, VTR 309 and a camera photographing apparatus not illustrated.

The above mentioned air feeding, water feeding and sucking apparatus 304 is provided with, for example, an air feeding valve 341, water feeding valve 342 and sucking valve 343 consisting of electromagnetic valves for controlling the air feeding, water feeding and sucking of the above mentioned scope 302 and a controlling circuit 344 for controlling these air feeding valve 341, water feeding valve 342 and sucking valve 343 and is connected to the above mentioned scope 302 through pipes 345. 346 and 347. This controlling circuit 344 is connected to an air feeding switch 348 instructing feeding air, a water feeding switch 349 instructing feeding water and a sucking switch instructing sucking in the above mentioned switch portion 317 provided in the operating section 318 of the scope 302.

The above mentioned MCU 306 has a driver 355 driving a motor 354 within the above mentioned scope 302 to vertically bend the above mentioned bendable portion 321 through a driving cable 353 within the above mentioned scope 302 and a bending angle detecting circuit 357 detecting the bending angle in the vertical direction of the bending portion 321 by a detecting signal from an encoder 356 within the scope 302 to detect the rotation amount of this motor 352. By the way, here, though not illustrated, also in the horizontal direction, the MCU 30 has a driver of a bending motor driving bending and a bending angle detecting circuit detecting the horizontal bending angle of the bending portion 321 by detecting the rotation amount of this motor.

Further, an MCU controlling circuit 358 inputting the detecting signal from this bending angle detecting circuit 357 and controlling the driver 355 is provided and is connected to a bending switch 361, speed switch 362, free/lock (abbreviated as F/L hereinafter) switch 363, angle vibration switch (abbreviated as AV hereinafter) switch 364 and straight switch 365 in the above mentioned switch portion 317 provided in the operating section 318 of the scope 302.

By the way, the respective switches in the above mentioned switch portion 317 are to instruct the above mentioned MCU 306 as predetermined. That is to say, the bending switch 361 is formed, for example, of a joystick and instructs the vertical and horizontal bending drive of the above mentioned bendable portion 321, the speed switch 362 instructs the speed of the bending drive, the F/L switch 363 instructs whether the bending of the bendable portion 321 is to be released or held, the AV switch 364 instructs the minute AV operation of the distal end of the scope 302, the straight switch 365 instructs whether the straightening function making zero the bending angle of the bent bendable portion 321 is to be carried out or not and the air feeding switch 348, water feeding switch 349 and sucking switch 30 respectively instruct the air feeding, water feeding and sucking apparatus 304 to feed air, feed water and suck as predetermined.

The above mentioned CCU 307 controls the above mentioned video processing circuit 337 and is provided with a CCU controlling circuit 369 communicating with this video processing circuit 337, a controlling apparatus 332 within the above mentioned light source apparatus 303, a controlling apparatus 344 within the above mentioned air feeding, water feeding and sucking apparatus 304 and the above mentioned MCU controlling circuit 358. This CCU controlling circuit 369 is connected to a freezing switch 371, releasing switch 372, panorama switch 373 and blur preventing switch 374 in the switch portion 370 provided in the CCU 307.

By the way, the respective switches in the above mentioned switch portion 370 are to give predetermined instructions to the above mentioned CCU 307. That is to say, the freezing switch 371 instructs, for example, whether the freezing function of freezing taking in an image of a frame memory not illustrated to obtain a still picture is to be operated or not, the releasing switch 372 instructs whether this freezing function is to be operated to obtain a still picture or not and whether a camera photographing apparatus not illustrated is to photograph this still picture or not, the panorama switch 373 instructs whether the panorama function of obtaining a later described panorama picture is to be operated or not and the blur preventing switch 374 instructs whether the blur preventing function for preventing a later described image blur is to be operated or not.

The operation of the thus formed endoscope system 301 shall be explained in the following.

First of all, the control of the freezing function or releasing function and various functions shall be explained.

Figure 24:
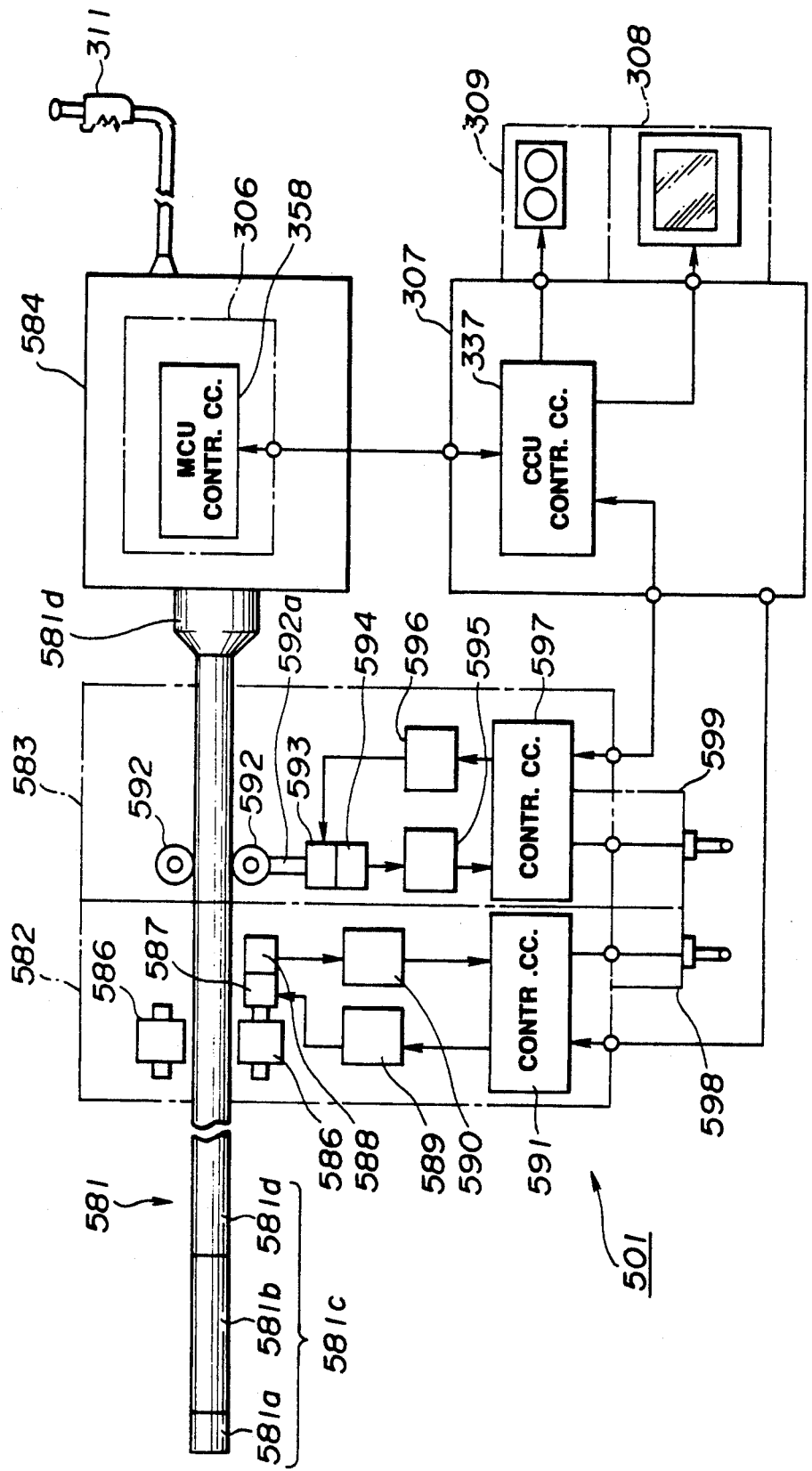
FIGS. 24 and 25 relate to the fifth embodiment of the present invention.

In carrying out the freezing function or releasing function, when the respective switches in the switch portion 317 are pushed, according to such flow as is shown in FIG. 24, the flow will start at a step (abbreviated as S hereinafter) 1, in S2, the CCU controlling circuit 369 judges the state of the bending switch 361 by the communication with the MCU controlling circuit 358 and, when this bending switch 361 is on, the flow will proceed to S8 in which the freezing function is switched off, in S9, the release is inhibited and a moving picture is displayed in the monitor 308 and the flow will proceed to S10 in which the flow ends.

In the above mentioned S2, when the bending switch 361 is off, the CCU controlling circuit 369 will judge in S3 the state of the AV switch 364 by the communication with the MCU controlling circuit 358, will judge in S4 the state of the straight switch 365, further will judge in S5 the state of the air feeding switch 350 by the communication with the controlling apparatus 344 within the air feeding, water feeding and sucking apparatus 304, will judge in S6 the state of the water feeding switch 349 and will judge in S7 the state of the sucking switch 348. When the respective switches are on, the flow will proceed to S8 but, when they are off, the flow will proceed to S10 to end the flow.

Figure 15:
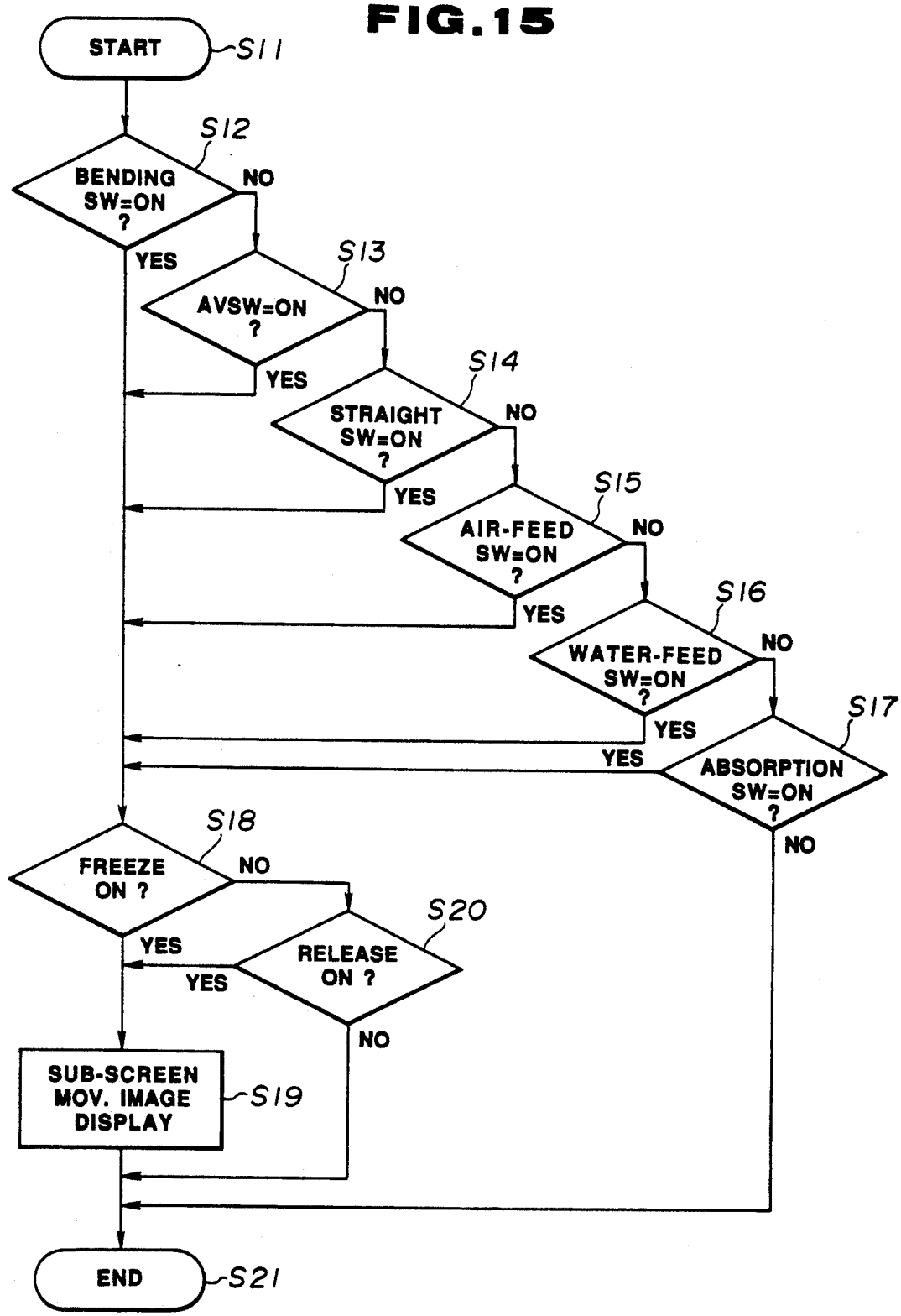

Further, in case a mode in which an image can be displayed in a sub-screen on the monitor 308 is switched on by a mode switching switch not illustrated, when the respective switches in the switch portion 317 are pushed, according to such flow as is shown in FIG. 15, the flow will start at S11, in S12, the state of the bending switch 361 is judged and, when this bending switch 361 is on, it will be judged in S18 whether the freezing function is on or not and, if the freezing function is on, the flow will proceed to S19 but, if it is off, the flow will proceed to S20. In S19, a still picture is displayed on the main screen in the monitor 308 and a moving picture is displayed on the sub-screen in the monitor 308. Then the flow will proceed to S21 to be ended. In S20, it is judged whether in the released state or not. If in the released state, the flow will proceed to S19 but, if not in the released state, the flow will proceed to S21.

In the above mentioned S12, when the bending switch 361 is off, in S13, the state of the AV switch 364 will be judged, in S14, the state of the straight switch 365 will be judged, in S15, the state of the air feeding switch 350 will be judged, in S16, the state of the water feeding switch 349 will be judged and, in S17, the state of the sucking switch 348 will be judged. When the respective switches are on, the flow will proceed to S18 but. when they are off, the flow will proceed to S21 to be ended.

Also, the state of the freezing switch 371 and releasing switch 372 is judged by the communication with the CCU controlling circuit 369. In case the freezing switch 371 or releasing switch 372 is on, the MCU controlling circuit 358 will stop the bending drive, AV operation and straightening function and further the controlling apparatus 344 within the air feeding, water feeding and sucking apparatus 304 will inhibit the air feeding, water feeding and sucking operations.

Thus, by the communication of the MCU controlling circuit 358 and the controlling apparatus 344 within the air feeding, water feeding and sucking apparatus 304 with the CCU controlling circuit, in case the scope 302 bends and drives, the still picture and moving picture will be able to be switched over to each other or the moving picture will be able to be displayed on the sub-screen and, in case the freezing function or releasing function operates, it will be possible to stop bending and driving the endoscope and therefore the operator can easily and safely perform a therapy and treatment.

Figure 16:
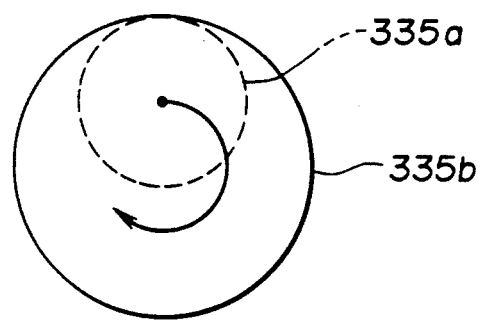

As shown in FIG. 16, a panorama picture is a picture of a region 335b obtained by synthesizing imaging regions 335a of a CCD 335 indicated by the broken line when the distal end of the scope 302 is rotated as indicated by the arrow by the AV operation.

Concretely, in case the AV operation makes one rotation in ⅓ second and the time for taking in a picture of one frame is 1/30 second, a picture of 10 frames will be able to be obtained by one rotation and, when coinciding images within the picture of the 10 frames are detected and synthesized by processing the picture, for example, in the video processing circuit 337, a panorama picture will be obtained.

Figure 17:
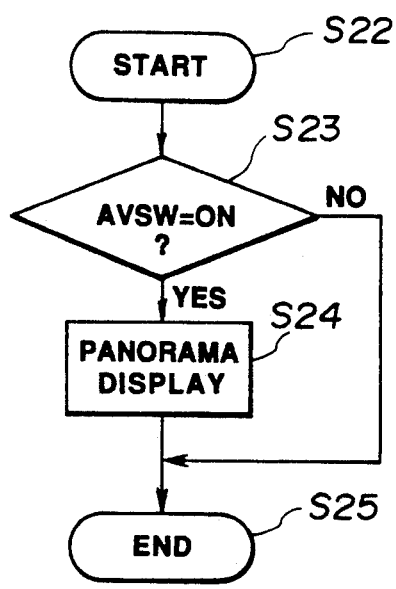
Figure 18:
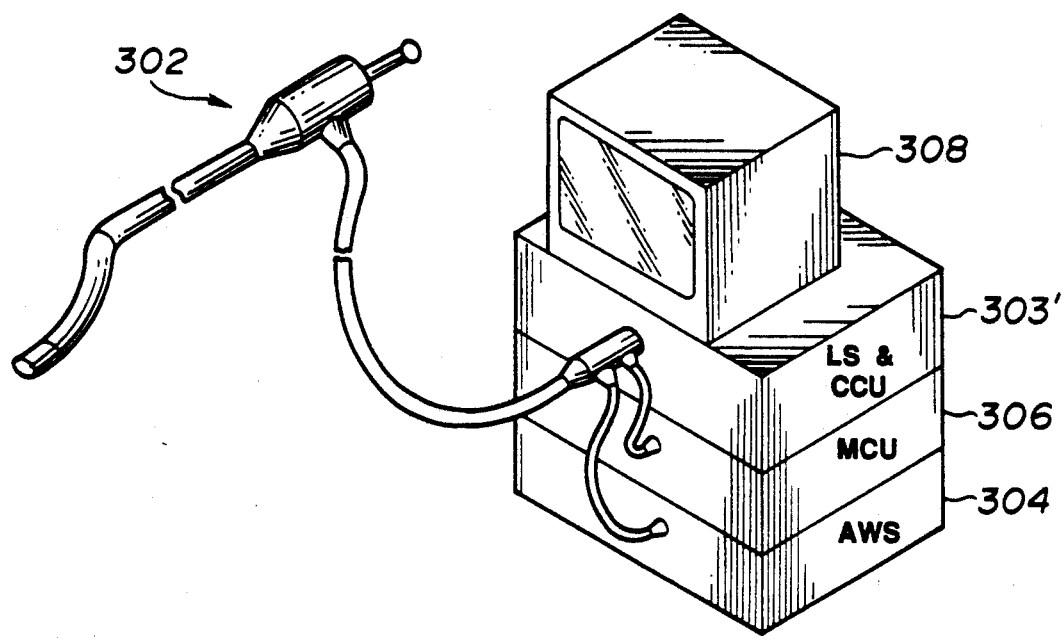
Figure 19:
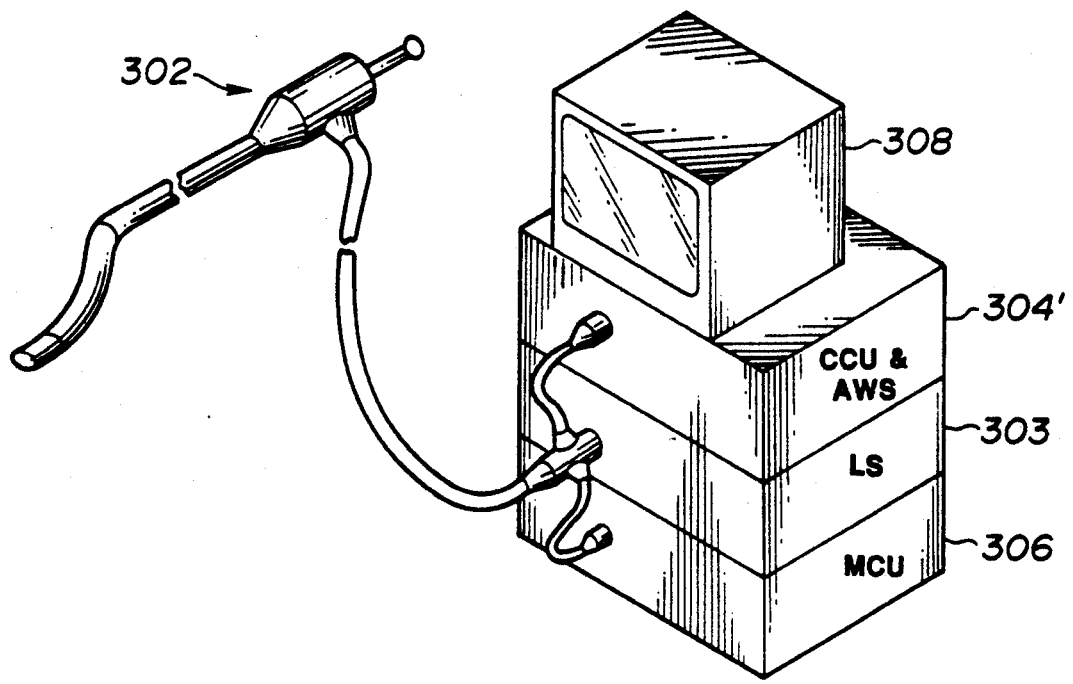

Such panorama picture displaying mode is selected by a mode switching switch not illustrated. As shown in FIG. 17, by the communication with the MCU controlling circuit 358, the CCU controlling circuit 369 starts at S22, in S23, the state of the AV switch 364 is judged and. if the AV switch 364 is on, the flow will proceed to S24 in which this panorama picture is displayed in the monitor 308 and then the flow will proceed to S25 in which the flow ends.

Further, by the communication with the CCU controlling circuit 369, the MCU controlling circuit 358 judges the state of the panorama switch 373. If the panorama switch 373 is on, the AV operation starting mode will be selected by a mode switching switch not illustrated.

By the way, by the mode switching switch not illustrated, not only the panorama picture displaying mode but also various displaying modes can be selected. For example, a displaying mode displaying only the image imaged always within the imaging region 335a (See FIG. 16) of the CCD 335 in which the distal end of the scope 302 is rotated by the AV operation can be selected.

Also, at the time of not only the AV operation but also, for example, the bending driving operation, by the communication with the MCU controlling circuit 358, the CCU controlling circuit 369 will be able to select a mode of displaying a panorama picture in the bending moving direction obtained by synthesizing pictures until the bending angle becomes a predetermined angle by a mode switching switch not illustrated and, by the communication with the CCU controlling circuit 369, the MCU controlling circuit 358 will judge the state of the panorama switch 373 and, if the panorama switch 373 is on, a mode of bending and driving until a predetermined angle will be able to be selected by the mode switching switch not illustrated.

Further, the switching switch may be formed of a keyboard or the like.

Thereby, the operator can easily obtain such various pictures as panorama pictures by selecting the mode.

When the CCU controlling circuit 369 communicates with the MCU controlling circuit 358 and the controlling apparatus 344 within the air feeding, water feeding and sucking apparatus 304, the CCU 307 will display various information in the monitor 308.

That is to say, for example, in case the power source of the MCU 306 is off, the signal from the MCU controlling circuit 358 will not be able to be detected and therefore the CCU controlling circuit 369 will judge the power source to be off, will output a predetermined command to the video processing circuit 337 and will display the informations "MCU OFF Bending Impossible" and "Switch ON MCU Power Source" in the monitor 308.

In case such abnormality as overrunning is caused to the MCU 306, the communication with the MCU controlling circuit 358 will become impossible and therefore the CCU controlling circuit 369 will judge that such abnormality as overrunning has been caused, will output a predetermined command to the video processing circuit 337 and will display in the monitor 308 an error message showing the contents of the abnormality together with the information "MCU Abnormal Bending Impossible". This error message is such information as, for example, "Overcurrent Flows To Motor" or "Input Signal from Encoder is Abnormal" in response to the contents of the abnormality.

For example, when the power source of the MCU 306 is switched on, the communication with the MCU controlling circuit 358 will be resumed and therefore the CCU controlling circuit 369 will detect the signal of the return of the MCU 306 and will display in the monitor 308 the information, for example, "Apply UP Bending".

Further, the MCU controlling circuit 358 judges the state of the bending switch 361 and displays in the monitor 308 such information as, for example, "↑", "↓", "→" or "←" in response to the state.

Also, the state of the F/L switch 363 is judged and the information "Free" or "Lock" is displayed in the monitor 308 in response to the state.

Further, the state of the AV switch 36 is judged and, in case the AV switch 364 is on, the information "AV ON" will be displayed in the monitor 308. Here, the AV operation designates the AV mode. For example the AV operation mode, AV period and AV speed are set by a mode switching means formed of a keyboard not illustrated and the information is displayed in the monitor 308 in response to these settings. That is to say, in case the AV operation mode is set, for example, to rotate clockwise (abbreviated as CW hereinafter), the information "CW" will be displayed in the monitor 308. In case the AV period is set, for example, to be ⅛ second, the information "Period ⅛ Second" will be displayed in the monitor 308. Also, in case the A/V speed is, for example, a speed of 45 degrees/second, the information "Speed 1" will be displayed in the monitor 308.

Also, the state of the speed switch 362 is judged and the information, for example, "Speed 1" is displayed in the monitor 308 in response to the speed.

Further, on the basis of the output of the bending angle detecting circuit 357 detecting the bending angle the information for example. "UP 60° "is displayed in the monitor 308.

For the bending resistance, for example, when the electric power which the driver 355 feeds to the motor 354 is detected by the MCU controlling circuit 358, the information, for example, "24W" will be displayed in the monitor 308.

In case such abnormality as overrunning is caused to the air feeding, water feeding and sucking apparatus 304, the communication with the controlling apparatus 344 will become impossible and therefore the CCU controlling circuit 369 will judge that such abnormality as overrunning has been caused to the air feeding, water feeding and sucking apparatus 304, will output a predetermined command and will display in the monitor 308 an error message showing the contents of the abnormality together with the information "Air Feeding, Water Feeding and Sucking Apparatus ABNORMAL". In response to the contents of the abnormality, this error message displays in the monitor 308 such information as "Electromagnetic Valve Not Good", "Suction Pressure Abnormal", "Signal Abnormal" or "Suction Bottle Contents Overflow".

Further the state of the air feeding switch 350, water feeding switch 349 and sucking switch 348 is judged and, in response to the state, the controlling apparatus 344 within the air feeding, water feeding and sucking apparatus 304 controls the air feeding valve 341, water feeding valve 342 and sucking valve 343 and, by communicating with the CCU controlling circuit 369, displays in the monitor 308 such information as, for example, "Feeding Air", "Feeding Water" or "Sucking".

Such various informations are displayed in the monitor 308 that the operator can easily hold the state of the endoscope system 301 and make a proper treatment.

The treatment of the case that the image can not be displayed in the monitor 308 shall be explained in the following.

First of all, in case the power source of the CCU 307 is off or in case such abnormality as overrunning is caused to the CCU 307, the communication with the CCU controlling circuit 369 will become impossible and therefore the MCU controlling circuit 358 will judge that the power source of the CCU 358 is off or such abnormality as overrunning is caused and will stop the bending drive, AV operation and straightening function.

In case the illumination is impossible because the power source of the light source apparatus 303 is off or the like and the picture can not be displayed in the monitor 308, the communication with the controlling circuit 332 within the light source apparatus 303 will become impossible and therefore the CCU controlling circuit 369 will judge that such abnormality that the power source of the light source apparatus 303 is off has been caused, will transmit a predetermined command to the video processing circuit 337, will display in the monitor 308 such information as, for example, "Illumination Impossible", will communicate with the MCU controlling circuit 358 and will stop the bending drive, AV operation and straightening function.

Thus, even in case no image can be displayed in the monitor 308, all the drives of the scope 302 will be stopped and therefore the body cavity interior will not be injured and will be safe.

The imaging signal of the image formed in the CCD 335 is input into the video processing circuit 337 through the preamplifier 336. This video processing circuit circuit 337 judges whether the luminance signal of this input imaging signal is above a predetermined threshold level or not and, in case it is above the threshold level, will judge that the distal end of the scope 302 is so close to the imaged object that the entire image is too bright to be seen and will transmit a predetermined signal to the CCU controlling circuit 369 and, on the basis of this signal, the CCU controlling circuit 369 will communicate with the MCU controlling circuit 358 and will stop the bending drive, AV operation and straightening function.

Thus, even in case the entire image is too bright to be seen, all the drives of the scope 302 will be stopped and therefore the body cavity interior will not be injured and will be safe.

Also, the video processing circuit 337 detects from the imaging signal water as mounted on the observing window or the like provided at the distal end of the scope 302 and transmits a predetermined signal to the CCU controlling circuit 369 and, on the basis of this signal, the CCU controlling circuit 369 communicates with the controlling circuit and controls to open and close as predetermined the air feeding valve 341, water feeding valve 342 and sucking valve 343 to remove the mounted water.

Thereby, the operator can always clearly obtain the image formed by the CCD 335 without requiring any special operation.

Further, when the blur preventing switch 374 is switched on, as described below, the CCU controlling circuit 369 will communicate with the MCU controlling circuit 358 and will control the MCU 306. That is to say, in case the distal end component 322 of the scope 302 approaches the imaged object or in the case of a magnified observation, the delicate movement of the distal end component 322 will be connected with the blur of the image. Therefore, in order to prevent it, the bendable portion 321 is controlled to be driven in the direction having no blur. That is to say, on the basis of the imaging signal of the image imaged by the CCD 335, the video processing circuit 337 compares the image with the image just before it, detects the coincidence and transmits the blur direction to the CCU controlling circuit 369 which communicates with the MCU controlling circuit 58 and controls the drive in the direction having no blur until there is no blur.

The thereby obtained image has substantially no blur.

In case a preferential switch not illustrated provided in a remote controlling portion 311 is set to prefer the scope 302 body, the CCU controlling circuit 369 will judge the state of the preferential switch through the MCU controlling circuit 358 and will display in the monitor 308 the operating information of the remote controlled operating part, for example, the information "Endoscope Operating Section PREFERRED". For example, here, "Endoscope Operating Section PREFERRED" is only displayed in the monitor 308 but the actual bending control follows the operation of the switch portion 317. Thereby, the scope 302 is controlled in response to the operating states of the respective switches in the switch portion 317 of the operating section 318 of the scope 302. Therefore, for example, in case a skilled person operates the remote controlling portion 311 and a beginner operates the switch portion 317 of the scope 302, with reference to the operation by the skilled person in each scene, the beginner will be able to actually operate the switches and therefore the educational effect is very high.

On the other hand, the operation information operated by the remote controlling portion 311 is transmitted from the MCU controlling circuit 358 to the CCU controlling circuit 369 and, for example, in the case of the switch controlling the bending drive, in response to the control contents, such information as "↑", "↓", "→" or "←" will be displayed in the monitor 308.

Thus, in the endoscope system 301 of the third embodiment, at least the CCU 307 and MCU 306 communicate and control with each other and therefore the system 301 is so high in the operability as to be able to be easily operated by the operator. Further, as various informations are displayed in the displaying monitor 308, not only the operability and safety are high but also the educational effect is very high. It has also the same effects as of the first embodiment.

In the third embodiment, as shown in FIG. 12, the respective functions are made separate but, as shown in FIGS. 18 to 22, different functions may be made integral. The system shown in FIG. 18 has a light source & CCU 303' in which the light source 303 and CCU 307 in FIG. 12 are made integral and has the MCU 306 and AWS 304 made separate. The system shown in FIG. 19 has a CCU & AWS 304' in which the CCU 307 and AWS 304 are made integral and has the light source apparatus 303 and MCU 306 made separate. The system shown in FIG. 20 has a light source & CCU 303' in which the light source apparatus 303 and CCU 307 are made integral and further has an MCU & AWS 306' in which the MCU 306 and AWS 304 are made integral. The system shown in FIG. 21 has a light source & MCU 303" in which the light source apparatus 303 and MCU 306 are made integral and further a CCU & AWS 307' in which the CCU 307 and AWS 304 are made integral. The system shown in FIG. 22 has a light source & CCU & AWS 304" in which the light source apparatus 303, CCU 307 and AWS 304 are made integral and a separate MCU 306.

The fourth embodiment of the present invention shall be explained with reference to FIG. 23. The fourth embodiment relates to a so-called external electric bending motor type endoscope system in which the bending motor of the third embodiment is provided outside the scope or, for example, within the MCU.

The same case as the third embodiment shall bear the same reference numeral and shall not be explained here.

Figure 23:
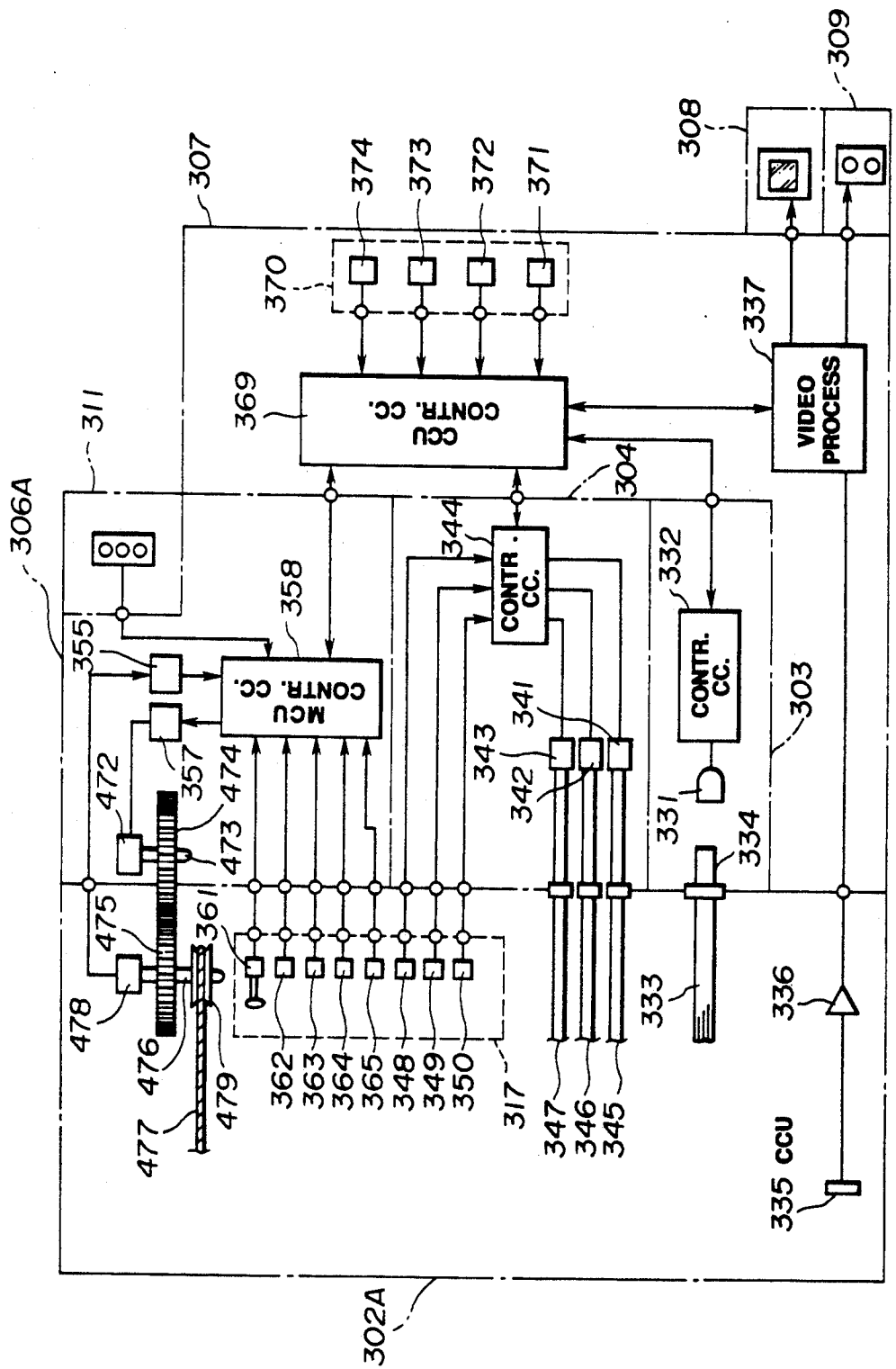
FIG. 23 is a formation diagram showing a schematic formation of an endoscope system of the fourth embodiment of the present invention.

As shown in FIG. 23, a bending driving motor 472 is arranged within an MCU 306A and a gear 474 is secured to a shaft 473 of this motor 472. A connector not illustrated of the scope 302A is connected and fixed to the MCU 306A and a gear 475 engaging with the above mentioned gear 474 is provided within this connector. A pulley 479 is secured to a shaft 476 of this gear 475 so as to be able to drive a bending cable 477. An encoder 478 is secured to the shaft 476 of the gear 475 so as to be able to detect a bent amount. The other formations are the same as in the third embodiment.

In the thus formed endoscope system of the fourth embodiment, when the blur preventing switch 374 is switched on, as described below, the CCU controlling circuit 369 will communicate with the MCM controlling circuit 358 and will control the MCU 306A. That is to say, the video processing circuit 337 will cut out only a part of all the pixels of the CCD 335 and will display them in the monitor 308. In case the distal end component 322 of the scope 302 blurs and the image moves within the CCD 335, the distal end component 322 will be moved so as to follow only a part of all the above mentioned pixels.

Thereby, even if the distal end component 322 blurs, the image displayed in the monitor 308 will not blur.

By the way, even in case not only the blur preventing switch 374 but also, for example, the AV switch 364 is switched on, this blur preventing operation may be started. As a result, even if the bendable portion 321 AV-operates and the distal end component 322 blurs, the image displayed in the monitor 308 will not blur.

When the panorama switch 373 is switched on, as described below, the CCU controlling circuit 369 will communicate with the MCU controlling circuit 358 and will control the MCU 606A. That is to say, when it is judged that the panorama switch 373 is switched on, the CCU controlling circuit 369 will control the bending drive for the MCU controlling circuit 358 to be up, straight, down, straight, right, straight, left and straight in the order mentioned and the video processing circuit 337 will take in a plurality of pictures in this driving state and will synthesize these pictures to obtain a panorama picture.

By the way, the method of obtaining a panorama picture is not limited to this but may be the method (See FIG. 6) shown in the third embodiment.

The other operations and effects are the same as in the third embodiment.

Figure 25:
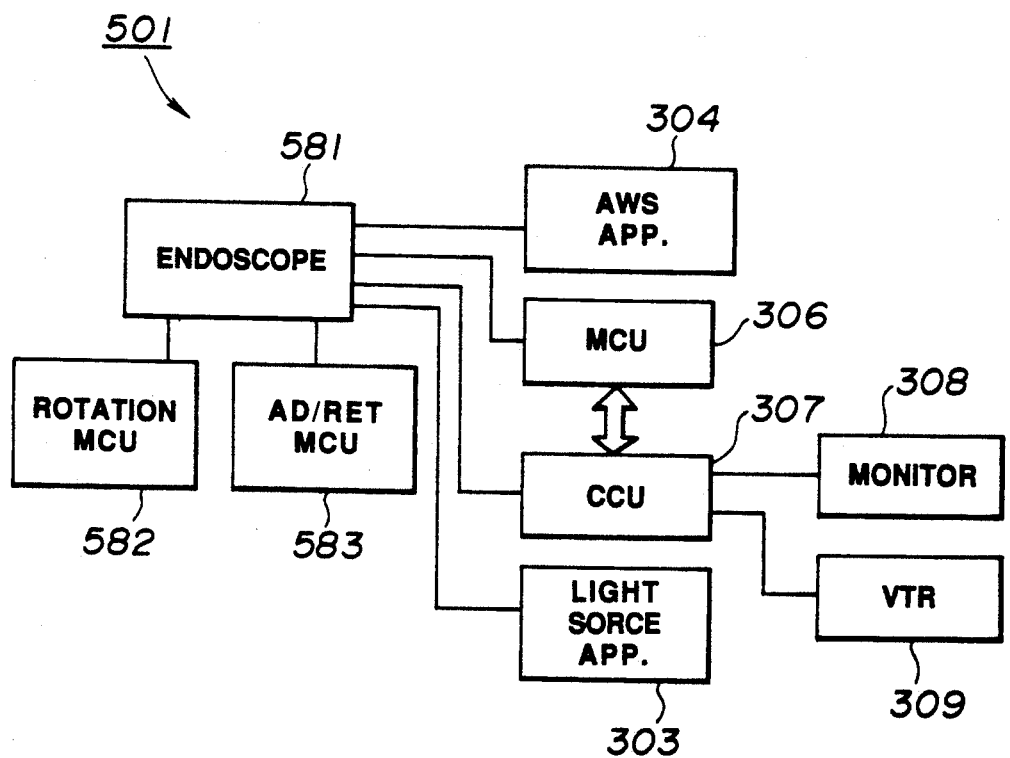

FIGS. 24 and 25 show an endoscope system 501 of the fifth embodiment. The fifth embodiment is provided with an inserting motor and rotating motor in addition to the bending motor of the third embodiment. Therefore, the motor controlling unit for the bending motor shall be represented by an MCU or bending MCU, the motor controlling unit for the inserting motor (advancing and retreating moving motor) shall be represented by an advancing and retreating MCU and the motor controlling unit for the rotating motor shall be represented by a rotating MCU.

The same case as the third embodiment shall bear the same reference numeral and shall not be explained here. A scope 581 is connected through a connector 581*d* to a controlling unit (abbreviated as a CU hereinafter) 584 having the bending MCU 306 built-in. This scope 581 comprises an insert section 581c fitted at the base end with the connector 581d, a bending driving bendable portion 581b provided at the distal end of a flexible portion 581 forming the base end side of this insert section 581c and a distal end component 581a provided at the distal end of this bendable portion 581b.

The above mentioned insert section 581c is provided on the base end side with an advancing and retreating MCU 583 advancing and retreating the scope 581 in the axial direction of the insert section 581c and a rotating MCU 582 rotating and driving the scope 581 around the axial direction of the insert section 581c.

This advancing and retreating MCU 583 has advancing and retreating drums 592 advancing and retreating the scope 581 and contacting the outer peripheral surface of the insert section 581c so that, when these drums 592 are rotated, the scope 581 will be able to be advanced and retreated. These advancing and retreating drums 592 are connected through bevel gears not illustrated and a shaft 592a to an advancing and retreating motor 593 driven by a driver 596. An encoder 594 detecting the advancing and retreating amount is connected to the shaft of this advancing and retreating motor 593 and is connected to an inserted amount detecting circuit 595. Further, the driver 596 and the inserted amount detecting circuit 595 are connected to an advance and retreat controlling circuit 597.

This rotating MCU 582 has rotating drums 586 rotating and driving the scope 581 and connected through bevel gears not illustrated and a shaft to a rotating motor 587 driven by a driver 589. An encoder 588 detecting a rotated amount is connected to the shaft of this rotating motor 587 and is connected to a rotating amount detecting circuit 590. Further, the driver 589 and rotated amount detecting circuit 590 are connected to a rotation controlling circuit 591.

As shown in FIG. 25, the endoscope system 501 of the fifth embodiment is formed by adding the advancing and retreating MCU 583 and rotating MCU 582 to the formation of the endoscope system 301 of the third embodiment.

Also, the above mentioned advance and retreat controlling circuit 597 and rotation controlling circuit 591 can communicate with a CCU controlling circuit 337.

The other formations are the same as in the first embodiment.

The thus formed endoscope system 501 of the fifth embodiment is formed by adding an advancing and retreating driving advancing and retreating MCU 583 and a rotating driving rotating MCU 582 to the endoscope system 301 of the third embodiment. These advancing and retreating MCU 583 and rotating MCU 582 communicate with the CCU controlling circuit 369 to operate substantially the same as the MCU 306.

Here, the advancing and retreating MCU 583 can be explained by replacing the description of bending with that of advancing and retreating in the operation of the MCU 306 of the third embodiment and the rotating MCU 582 can be explained by replacing the description of bending with that of rotating in the operation of the MCU 306 of the third embodiment. Therefore, they shall not be explained here.

Also, the advancing and retreating MCU 583 and rotating MCU 582 may be combined to operate simultaneously.

By the way, the CCU controlling circuit 369 may be provided with a pipe hollow detecting function so that the distal end component 581a of the scope 581 may be bent and controlled so as to be always directed to the center of the pipe hollow. That is to say, the darkest part is detected from the output of the video processing circuit 337, in which direction from the center of the CCD 335 the CCU controlling circuit 369 is positioned is judged by communicating with the MCU controlling circuit 358 and the result is transmitted to the MCU controlling circuit 358.

On the basis of the transmission, the MCU controlling circuit 358 bends the bendable portion 581b, for example, in the up and right directions. When the darkest part coincides with the center of the CCD 335, the CCD controlling circuit 369 will transmit a command to stop the bending operation to the MCU controlling circuit 358 of the MCU 306. Thereby, the bendable portion 581 will stop and the distal end component 581a will be always directed in the center direction of the pipe hollow.

By communicating with the CCU controlling circuit 369, when the output signal of the CCU controlling circuit 369 is a command to stop the bending operation, the advance and retreat controlling circuit 597 of the advancing and retreating MCU 583 will insert the scope 581 and, when the output signal of the CCU controlling circuit 369 is a command of the bending operation, the scope 581 inserting operation will be stopped so that the automatic insertion may be possible. By the way, the rotating MCU 582 may also properly participate in the automatic inserting operation.

The other operations and effects are the same as in the third embodiment.

Figure 26:
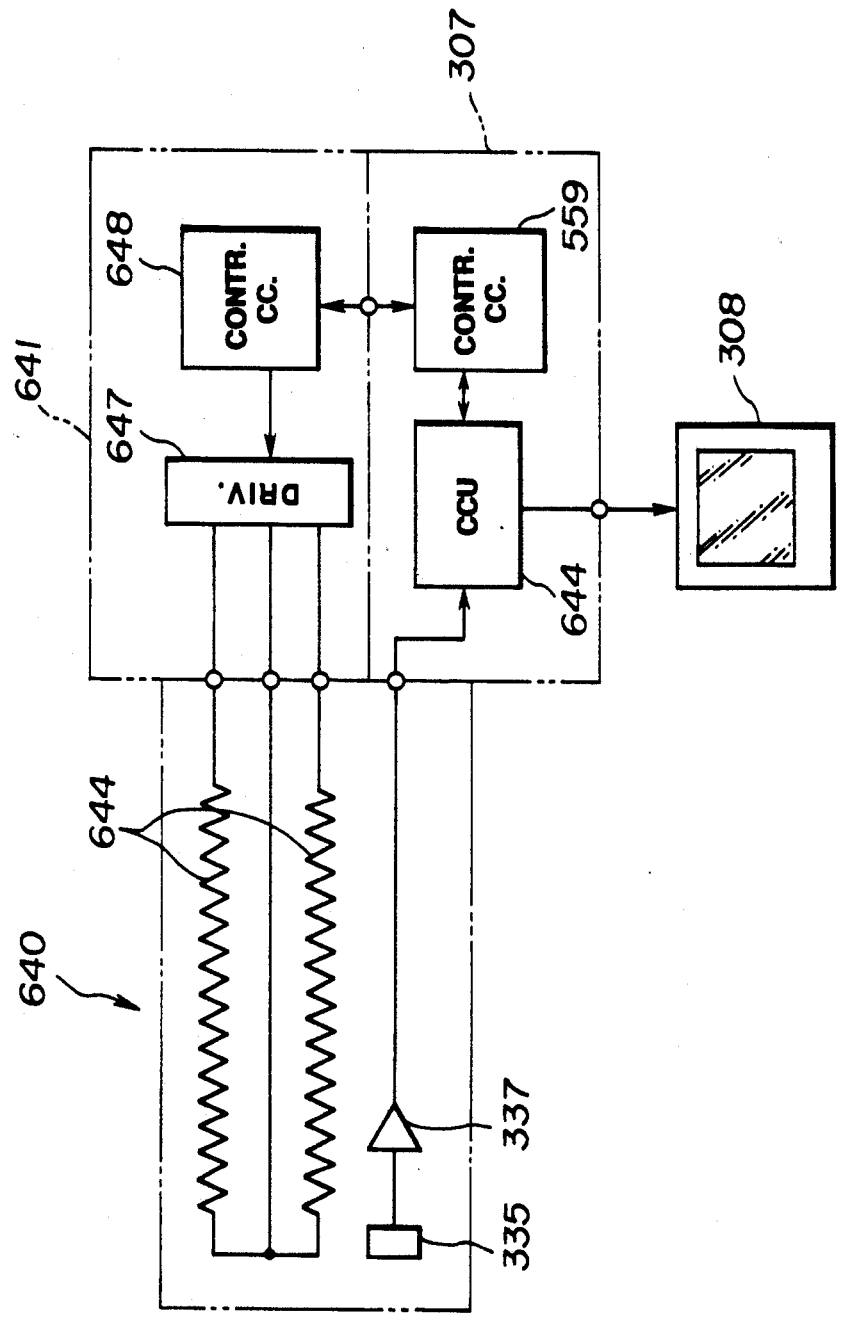
FIG. 26 is a formation diagram showing a schematic formation of an endoscope system of the sixth embodiment of the present invention.

FIG. 26 is a block diagram for explaining the functional formation of an endoscope system relating to the sixth embodiment.

In the sixth embodiment, a shape memorizing alloy is used for the driving means instead of the motor in the third embodiment.

The same case as of the third embodiment shall bear the same reference numeral and shall not be explained here.

As shown in FIG. 26, for example, a shape memorizing alloy (abbreviated as an SMA hereinafter) 644 is arranged as a bending driving means within a scope 640 and is connected to a driver 647 within an SMA controlling unit bending driving when the SMA 644 is electrified. This driver 647 is connected to an SMA controlling circuit 648 controlling bending and capable of communicating with the CCU controlling circuit 369. This driver 647 can detect a bent amount by an electric power amount electrifying the SMA 644.

The other formations, operations and effects are the same as in the third embodiment.

The seventh embodiment of the present invention shall be explained in the following.

Figure 27:
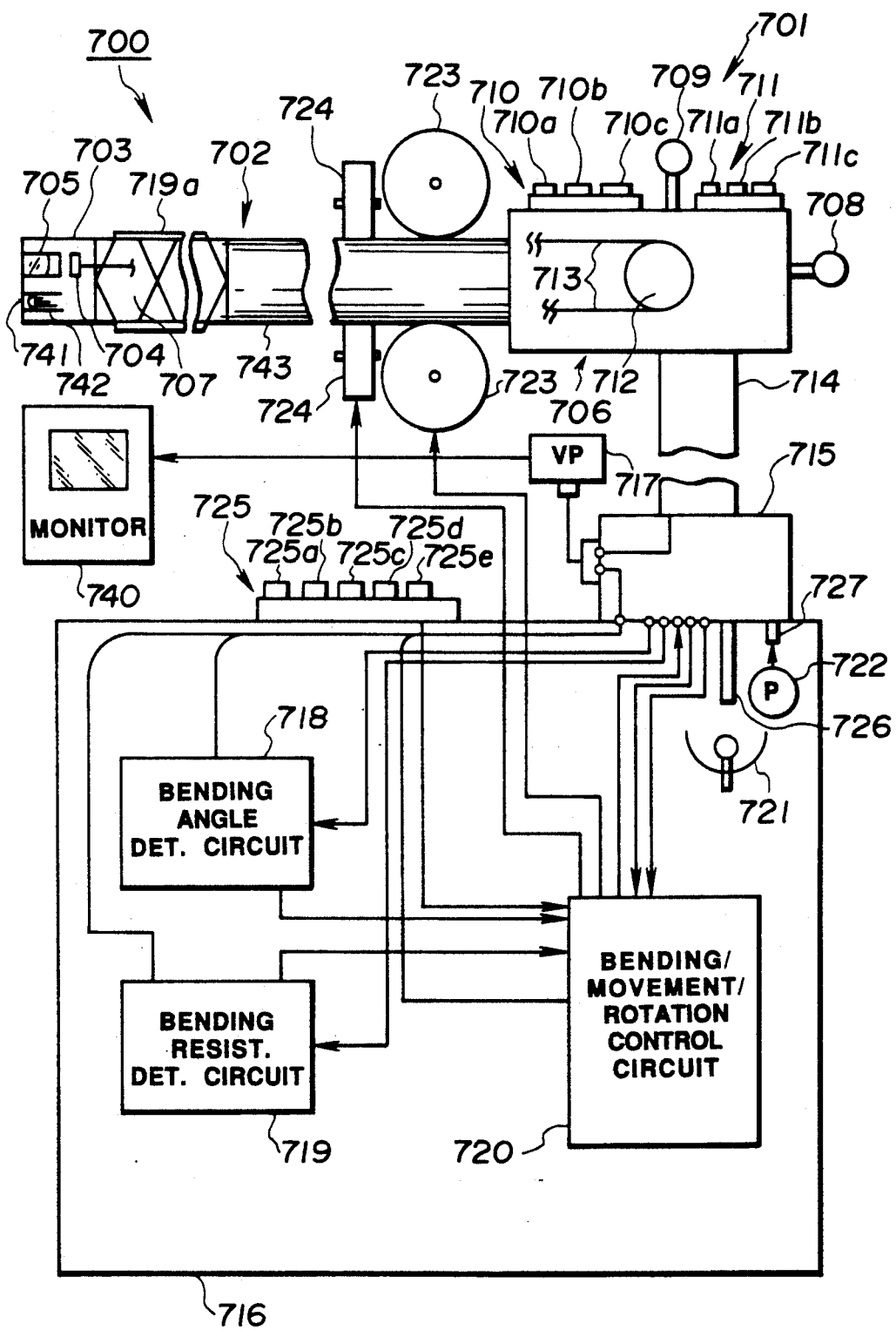
Figure 28:
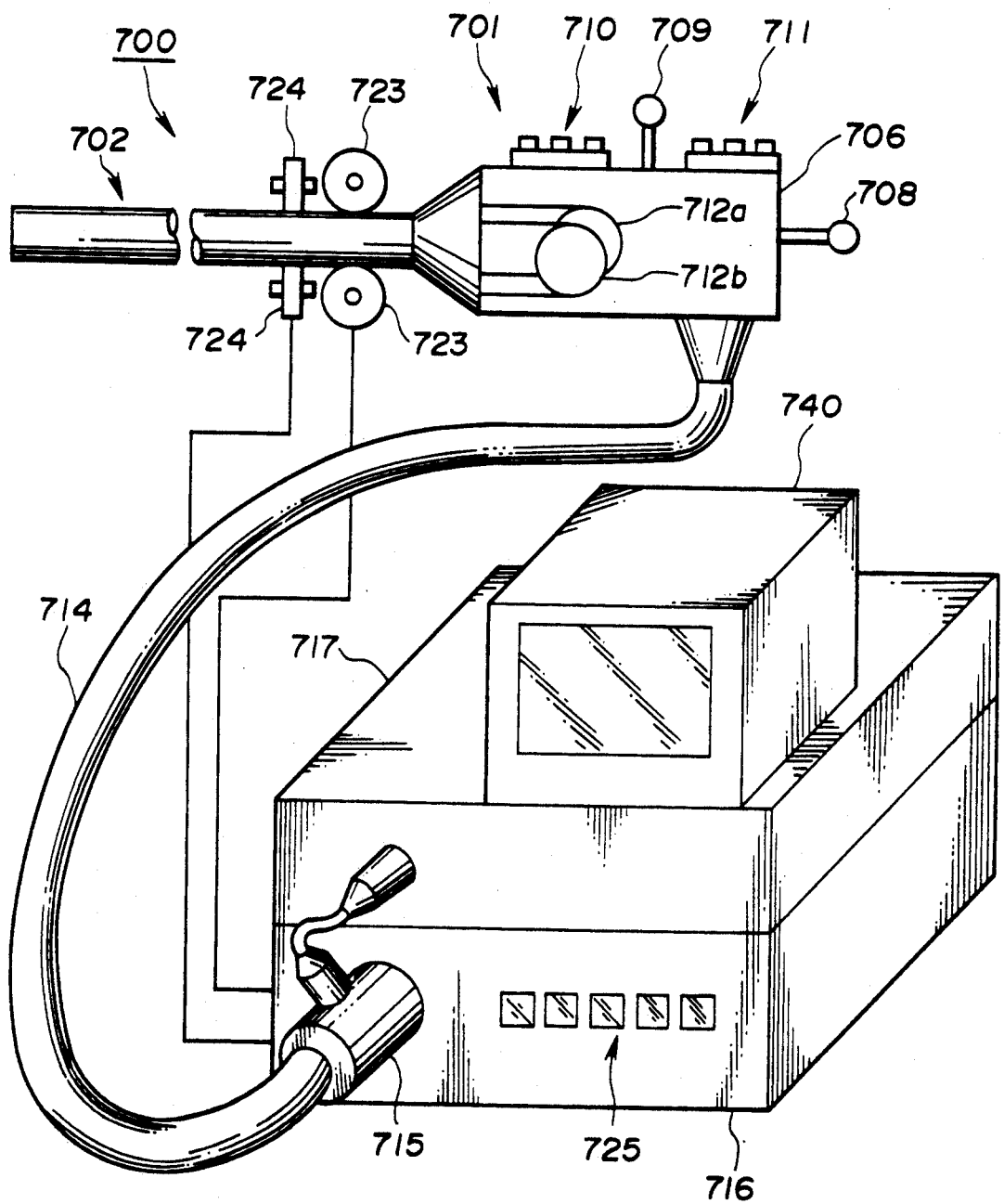
Figure 39:
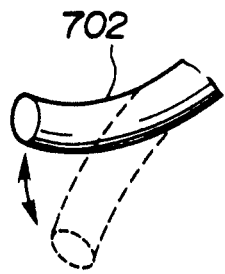
Figure 40:
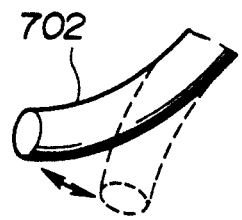
Figure 41:
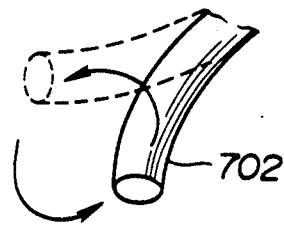
Figure 42:
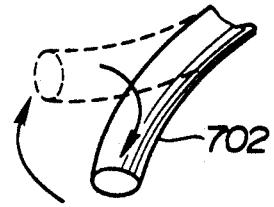
Figure 43:
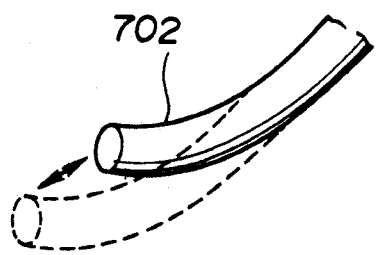
Figure 44:
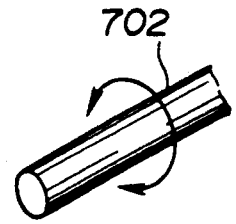

As shown in FIGS. 27 and 28, an endoscope system of this embodiment comprises an electronic endoscope 701, a controller 716, a CCU (expressed by a VP in this embodiment) 717 to which the endoscope 701 is connectable and a monitor 740 connected to the VP 717.

The endoscope 701 comprises an elongate and flexible insert section 702, a larger diameter operating section 706 continuously provided at the rear end of the insert section 702 and a universal cable 714 extended laterally from the operating section 706. A connector 715 removably connected to the controller 716 is provided at the opposite end of the universal cable 714. The insert section 702 comprises a pliable portion 743 coupled with the operating section 706, a bendable portion 707 continuously provided at the front end of the pliable portion 743 and capable of bending and a distal end component 703 continuously provided at the front end of the bendable portion 707.

The distal end component 708 is provided with an observing window 705a, an illuminating window 741a and an air feeding/water feeding port (not illustrated). The observing window 705a includes an objective lens 705. A solid state imaging device 704 is disposed in the focus position of the objective lens 705. A signal line connected to the solid state imaging device 704 is extended through the insert section 702, operating section 706 and universal cable 714 and is connected to the connector 715. A light distributing lens 741 is fitted in the illuminating window 741a and a light guide 742 is continuously provided at the rear end of the light distributing lens 741. The light guide 742 is extended through the insert section 702, operating section 706 and universal cable 714 and is connected at the entrance end to a light guide pipe 726 extending from the connector 715. The air feeding/water feeding port is connected to an air feeding/water feeding tube which is inserted through the insert section 702, operating section 706 and universal cable 714 and is connected to an air feeding pipe 727 extending from the connector 715.

A contact pressure sensor 719a is provided on the outer periphery of the bendable portion 707. A signal line connected to the contact pressure sensor 719a is extended through the insert section 702, operating section 706 and universal cable 714 and is connected to the connector 715.

The operating section 706 is provided with a joystick 708 for bending the bendable portion 707, a joystick 709 for moving (advancing/retreating) and rotating the insert section 702 and switches 710 and 711 described later.

The operating section 706 is provided with a pair of bending driving motors 712a and 712b. A bending wire 713 inserted through the insert section 702 is attached to the bending driving motor 712 (representing each of 712a and 712b) and is secured at the fore end to the distal end of the bendable portion 707. By rotating the bending driving motor 712, the bending wire 713 is pushed or pulled to bend the bendable portion 707 upward, downward, rightward and leftward. Further, an encoder 718a is attached to the bending driving motor 712. A signal line connected to the encoder 718a is extended through the insert section 702, operating section 706 and universal cable 714 and is connected to the connector 715.

The controller 716 houses therein a bending angle detecting circuit 718 connected to the encoder 18a through the connector 715, a bending resistance detecting circuit 719 connected to the contact pressure sensor 719a through the connector 715, a bending/movement (advance & retreat)/rotation controlling circuit 720, a lamp 721 and a pump 722.

The VP 717 connected to the solid state imaging device 704 through the connector 715 and cable 700 processes an output signal of the solid state imaging device 704 into a video signal which is output to the monitor 740. Then, the monitor 740 displays an image of an object to be examined. On the basis of an output of the encoder 718a, the bending angle detecting circuit 718 detects a bending angle of the bendable portion 707 and displays the detected bending angle in the monitor 740 through the VP 717. The information of the bending angle from the bending angle detecting circuit 718 is also transmitted to the bending/movement/rotation controlling circuit 720. On the basis of an output of the contact pressure sensor 719a provided in the bendable portion 707, the bending resistance detecting circuit 719 detects a bending resistance and displays the detected bending resistance in the monitor 740 through the VP 717. The information of the bending resistance from the bending resistance detecting circuit 719 is also transmitted to the bending/movement/rotation controlling circuit 720. The lamp 721 is so arranged as to project an illuminating light beam onto the entrance end of the light guide 742 within the light guide pipe 726. Further, the pump 722 is so arranged as to feed air to the air feeding pipe 727.

As shown in FIG. 29, the bending/movement/rotation controlling circuit 720 drives the bending driving motors 712a and 712b, a movement motor 723a for driving movement rollers 723 held on the periphery of the insert section 702 and a rotation motor 724a for driving rotation rollers 724 held on the periphery of the insert section 702. As shown in FIG. 28, a set of switches 725 is provided on the outer surface of the controller 716. Also, as shown in FIG. 29, the joysticks 708 and 709 and switches 710, 711 and 725 are connected to the bending/movement/rotation controlling circuit 720 so that the controlling circuit 720 may display the operating conditions of the joysticks 708 and 709 and switches 710, 711 and 725 in the monitor 740 through the VP 717.

In addition, as shown in FIG. 29, the bending/movement/rotation controlling circuit 720 includes a controlling circuit 728 for receiving the information from the joysticks 708 and 709, the switches 710, 711 and 725, the bending angle detecting circuit 718, the bending resistance detecting circuit 719, drivers 732a, 732b, 732c and 732d for driving the motors 712a, 712b, 723a and 724a, respectively, speed controlling circuits 729a to 729d, rotating direction indicating circuits 730a to 730d and free/lock circuits 731a to 731d for controlling the drivers 732a, 732b, 732c and 732d on the basis of the information from the controlling circuit 728, respectively.

As shown in FIG. 27, the switch 710 comprises a minute bending vibration on/off switch 710a, a minute moving (advancing and retreating) vibration on/off switch 710b and a minute rotating vibration on/off switch 710c. The switch 711 comprises a bending free/lock switch 711a, a movement free/lock switch 711b and a rotation free/lock switch 711c. The switch 725 comprises a set of a minute bending vibration selecting switch 725a, bending/movement/rotation/swing setting selecting switch 725b, angle specifying switch 725c, speed specifying switch 725d and all-free switch 725e.

The angle specifying switch 725c is so arranged as to specify an angle or length of each minute vibration at such three stages as, for example, a narrow angle (N), medium angle (M) and wide angle (W). The speed specifying switch 725d is so arranged as to specify a speed of each minute vibration at such three stages as, for example, a low speed (L), medium speed (M) and high speed (H).

The joysticks 708 and 709 are so arranged that, when their levers are tilted upward, downward, rightward or leftward, they will output the information of the direction and degree of each tilting and the output information will be applied to the controlling circuit 728.

The operation of this embodiment shall now be described. The endoscope apparatus of this embodiment can make various forms of operations by combining such three types of motions as the bending, movement (advance and retreat) and rotation with three types of minute vibrations of the bending, movement and rotation. The following typical operations shall be described below in the order with reference to FIGS. 30 to 38.

(I) The operation during the normal bending process (FIG. 30).

(II) The operation during the non-bending process in a parallel minute vibration mode (FIG. 31).

(III) The operation during the bending process in a parallel minute vibration mode (FIG. 32).

(IV) The operation in an orthogonal minute vibration mode (FIG. 33).

(V) The operation based on a swing motion, minute moving vibration and minute rotating vibration (FIG. 34).

(VI) The operation in a combination of a minute rotating vibration and minute bending vibration (FIG. 35).

(VII) The operation when the conditions of a minute rotating vibration are changed (FIG. 36).

(VIII) The operation in a combination of a minute moving vibration and minute bending vibration (FIG. 37).

(IX) The operation when the conditions of a minute moving vibration are changed (FIG. 38).

In FIG. 30, (a) and (b) represent operations of the joysticks 708 and 709, respectively, and (c) to (e) represent operations of the speed controlling circuit 729a, the rotating direction indicating circuit 730a and the free/-lock circuit 731a for the bending driving motor 712a, respectively. Likewise, (f) to (h) represent operations of the respective circuits 729b, 730b and 731b for the bending driving motor 712b; (i) to (k) represent operations of the respective circuits 729c, 730c and 731c for the movement motor 723a; (l) to (n) represent operations of the respective circuits 729d, 730d and 731d for the rotation motor 724a.

Also, in FIGS. 31 to 38, (a) to (c) represent operations of the switches 710a to 710c, respectively; (d) and (e) represent operations of the joysticks 708 and 709, respectively; and (f) to (h) represent operations of the switches 725a, 725c and 725d, respectively. Furthermore, (i) and (j) represent operations of the speed controlling circuit 729a and the rotating direction indicating circuit 730a for the bending driving motor 712a, respectively. Likewise, (k) and (l) represent operations of the respective circuits 729b and 730b for the bending driving motor 712b; (m) and (n) represent operations of the respective circuits 729c and 730c for the movement motor 723a; and (o) and (p) represent operations of the respective circuits 729d and 730d for the rotation motor 724a, respectively.

First, (I) the operation during the normal bending process shall be described with reference to FIG. 30.

When the joystick 708 is operated in the upward (referred to as U hereinafter) direction as shown at (a) in FIG. 30, the voltage depending on the tilting degree will be transmitted from the controlling circuit 728 to the speed controlling circuit 729a. The speed controlling circuit 729a will output pulses of a frequency depending on the applied voltage value as shown at (c). In other words, the speed controlling circuit 729a will output pulses of a lower frequency when the voltage is low and pulses of a higher frequency when it is high. The motor 712a will be thereby rotated in the direction corresponding to the U direction at a gradually increased speed. Note that the motors 712a, 712b, 723a and 724a are respectively stepping motors. The rotating direction indicating circuit 730a will output a high level (referred to as an H hereinafter) when the joystick 708 is operated in the downward (referred to as D hereinafter) direction but a low level (referred to as an L hereinafter with it in mind that the L means a low level for signals but a left for directions) in other cases. As shown at (d), the rotating direction indicating circuit 730a controls the motor 712a so that it will rotate forward when the output is at an L but backward when the output is at an H. The free/lock circuit 731a will output an L when the freely bending state is indicated by the free/lock switch 11a or the all-free switch 725e but an H in other cases. As shown at (e), the free/lock circuit 731a controls the motor 712a so that it will be locked when the output is at an H but will be set free when the output is at an L.

The foregoing similarly applies to the other D of the rightward (referred to as R hereinafter) and leftward (referred to as L hereinafter) directions as shown at (a) and (c) to (h) and hence the explanation of those directions shall be omitted here.

Then, when the joystick 709 is operated in the advance (designated by "Push" in the drawing), the voltage depending on the tilting degree will be fed from the controlling circuit 728 to the speed controlling circuit 729a as shown at (i) so that the motor 723a will be rotated forward and the insert section 702 will be advanced by the movement rollers 723. As shown at (j), the rotating direction indicating circuit 730c will output an H when the joystick 709 is operated in the retreating (designated by "Pull" in the drawing) direction but will output an L in other cases. It is to be noted that the retreating or pulling operation is also similarly performed as shown at (b) and (i) to (k) and therefore shall not be explained here.

Next, when the joystick 709 is operated in the R rotating direction, the voltage depending on the tilting degree will be fed from the controlling circuit 728 to the speed controlling circuit 729a as shown at (l) so that the motor 724a will be rotated forward and the insert section 702 will be rotated rightward by the rotating rollers 723. As shown at (m), the rotating direction indicating circuit 730d will output an H when the joystick 709 is operated in the L-rotating direction but will output an L in other cases. It is to be noted that the L-rotating operation is also similarly performed as shown at (b) and (l) to (n) and therefore shall not be explained here.

When the free/lock switches 711a, 711b and 711c are operated together, the free/lock circuits 731a to 731d will output L's to set the motors 712a, 712b, 723a and 724a free. The latter process will also occur when the all-free switch 725e is turned on.

Further, the minute bending vibration mode selector switch 725a is a switch for selecting the directions of the minute vibration and the directions of the swing motion by turns. More specifically, whenever depressed, the switch 725a will cyclically select one of the minute vibration in the same direction as the bending direction (referred to as a parallel minute vibration hereinafter), the minute vibration orthogonal to the bending direction (referred to as an orthogonal minute vibration hereinafter), the rightward swing motion and the leftward swing motion. The bending/movement/rotation/swing setting selecting switch 725b will make it possible to set a minute vibrating angle and minute vibrating speed in various forms of operations, whenever depressed. For example, when the operator desires to set an angle and speed of the minute rotating vibration, the switch 725b will be depressed twice to get into the rotation setting state and then the speed specifying switch 725d and angle specifying switch 725c will be depressed so as to make a minute rotating vibration at the desired speed and angle. Incidentally, the switch 725b is arranged to cyclically select one of the bending, movement, rotation and swing by turns.

Next, (II) the operation during the non-bending process in a parallel minute vibration mode shall be described with reference to FIG. 31.

When the minute bending vibration switch 710a is turned on as shown at (a) in FIG. 31, the bendable portion 707 will develop a minute vibration (reciprocal motion) under the conditions set by the switches 725a, 725c and 725d. More specifically, when the switch 725a is set in the parallel minute vibration mode as shown at (f), the switch 725c is set in a low speed as shown at (g) and the switch 725d is set in a narrow angle as shown at (h), the rotating direction indicating circuit 730a for the UD motor 712a will successively output an H and L alternately as shown at (j) and the speed controlling circuit 729a will output pulses with the pulse width depending on a speed value set by the switch 725c as shown at (i). Therefore, the motor 712a will be repeatedly rotated forward and backward so that the bendable portion 707 will develop minute vibrations in the UD directions. When the switch 725c is set at a high speed as shown at (g), the width of the pulses output from the speed controlling circuit 729a will be reduced as shown at (i) and thereby the bendable portion 707 will develop a minute vibration at a high speed. When the bending angle is set at a wide angle, the bendable portion 707 will develop a minute vibration with a larger amplitude.

Although in this embodiment the bending angle is set on the basis of the output frequency of the rotating direction indicating circuit 730a as shown at (j), the bending angle may be controlled by detecting an angle of rotation of the motor 712a from the output of the encoder 718a.

Further, when an orthogonal minute vibration mode is set by the switch 725a, the RL motor 712b will be operated upon turning on the switch 10a, causing the bendable portion 707 to develop minute vibrations in the RL directions.

Note that the foregoing description corresponds to the case that the switch 710a is operated without operating the joystick 708.

Now, (III) the operation during the bending process in a parallel minute vibration mode shall be described with reference to FIG. 32. In other words, the case of depressing the switch 710a while operating the joystick 708 shall be described. For brevity of the explanation, the operation of the joystick shall be limited to the on/off control (that is, the tilting degree of the joystick 708 shall not be taken into account) and the minute vibration shall be limited to a low speed and narrow angle in the following description. As with the foregoing operation in which the joystick 708 is not operated, however, it is possible to selectively set the speed (high speed/low speed, etc.) and angle (wide angle/narrow angle, etc.) by the switches 725c and 725d.

In case a parallel minute vibration mode is set as shown at (f) in FIG. 32, when the switch 710a is turned on and the joystick 708 is operated in the U direction, the rotating direction indicating circuit 730a will output an H and L alternately as shown at (j) so that the L will last longer than the H. Thus, the driving period in the U direction will be longer than that in the D direction. At this time, the speed controlling circuit 729a will output pulses depending on the specified speed as shown at (i). Therefore, the bendable portion 707 will be bent in the U direction while minutely vibrating in the UD directions.

When the joystick 708 is turned off, that is, returned to a neutral position, the bendable portion 707 will develop just minute vibrations in the UD directions.

Further, when the joystick 708 is turned toward the D side, the rotating direction indicating circuit 730a will output an H and the speed controlling circuit 729a will output pulses depending on a specified speed, whereby the bendable portion 707 will be bent toward the D side. In this case, when the switch 710a is turned on, the rotating direction indicating circuit 730a will output pulses with the duration of the H longer than that of the L and the speed controlling circuit 729a will output pulses depending on a specified speed. Therefore, the bendable portion 707 will be bent in the D direction while minutely vibrating in the UD directions.

Likewise, when the joystick 708 is operated in the R direction, the bendable portion will be bent in the R direction while minutely vibrating in the RL directions. Also, when the joystick 708 is operated in the L direction, the bendable portion will be bent in the L direction while minutely vibrating in the RL directions.

Next, (IV) the operation in an orthogonal minute vibration mode shall be described with reference to FIG. 33.

For brevity of the explanation, the operation of the joystick 708 shall be limited to the on/off control and the minute vibration shall be limited to a low speed and narrow angle in the following description as well.

When the switch 710a is operated without operating the joystick 708 as shown at (a) and (d) in FIG. 33, the bendable portion 707 will develop minute vibrations in the RL directions as mentioned above.

When the joystick 708 is operated in the U direction under the above condition, the bendable portion 707 will be bent in the U direction as shown at (i) and (j) while minutely vibrating in the RL directions as shown at (k) and (1). Likewise, when the joystick 708 is operated in the D direction, the bendable portion 707 will be bent in the D direction while minutely vibrating in the RL directions.

Further, when the joystick 708 is operated in the L direction, the bendable portion 707 will be bent in the L direction as shown at (k) and (l) while minutely vibrating in the UD directions as shown at (i) and (j). Likewise, when the joystick 708 is operated in the R direction, the bendable portion 707 will be bent in the R direction while minutely vibrating in the UD directions.

Although the foregoing explanation has been made as operating the joystick in any one of the U, D, R and L directions, the joystick may be operated to include either one of the UD directions and either one of the RL directions in a combined manner. In this case, the bendable portion 707 will be bent in a direction intermediate between the two directions in which the joystick is operated while minutely vibrating in the UD and RL directions.

Next, (V) the operation based on the swing motion, minute moving vibration and minute rotating vibration shall be described with reference to FIG. 34.

Here, the case that the switch 725a is set in a rightward swing mode or a leftward swing motion mode as shown at (f) shall be explained along with other cases of performing the movement and rotation.

When the switch 710a is turned on as shown at (a), the speed controlling circuits 729a and 729b will output pulses depending on the speed set by the switch 725c as shown at (i) and (k). At this time, the rotating direction indicating circuits 730a and 730b will output respective trains of pulses which are 90 degrees out of phase as shown at (j) and (1). The setting of the switch 725a determines whether a rightward or leftward swing motion. In the case of a rightward swing, the output pulses of the rotating direction indicating circuit 730a will be 90 degrees ahead of those of the rotating direction indicating circuit 730b. In the case of a leftward swing, the phase relationship will be reversed. The bendable portion 707 will be thereby caused to develop a rightward or leftward swing motion. Note that this swing motion is also one form of the minute vibration (reciprocal motion). This is because the swing motion results from a combination of a linear minute vibration in the UD directions and a linear minute vibration in the RL directions. Therefore, by appropriately setting a phase difference between two trains of the output pulses from the rotating direction indicating circuits 730a and 730b, an elliptic swing motion can be also made.

When the joystick 708 is operated in the R direction, for example, during the above swing motion, the rotating direction indicating circuit 730b will output pulses with the duration of the H shorter than that of the L. This allows the bendable portion 707 to bend in the R direction while continuing the swing motion. As to the other directions, the bendable portion 707 is similarly bent while continuing the swing motion in the corresponding direction in which the joystick 708 is operated. The more detailed explanation shall be omitted here.

There shall now be described minute moving and rotating vibrations. Note that the speed and angle (length) of the movement and the speed and angle of the rotation can be set by the switches 725c and 725d after the switch 725b is set in a movement or rotation mode. In the example in FIG. 34, the movement and rotation are both set in a low speed and narrow angle mode.

Under the condition that the minute moving vibration switch 710b and the minute rotating vibration switch 710c are turned off as shown at (b) and (c), when the joystick 709 is operated so as to include both of the advance (Push) direction and the R rotating direction (i.e., operated obliquely between the Push direction and the R rotating direction) as shown at (e), the rotating direction indicating circuits 730c and 730d will output L's as shown at (n) and (p) and the speed controlling circuits 729c and 729d will output pulses in a low speed mode as shown at (m) and (o). Therefore, the insert section 702 will advance while rotating rightwards.

On the other hand, when the minute moving vibration switch 710b and the minute rotating vibration switch 710c are turned off as shown at (b) and (c), the rotating direction indicating circuits 730c and 730d will output pulses in a narrow angle mode as shown at (n) and (p). Then, the speed controlling circuits 729c and 729d will output pulses in a low speed mode as shown at (m) and (o). Therefore, the insert section 702 will develop a minute moving vibration (minute movement) while continuing a minute rotating vibration (minute rotation).

Now, when the joystick 709 is operated obliquely between the retreating (Pull) direction and R rotating direction during the combined operation of the minute rotating vibration and minute moving vibration, the speed controlling circuits 729c and 729d will output pulses in a low speed mode, the rotating direction indicating circuit 730c will output pulses with the duration of the H longer than that of the L and the rotating direction indicating circuit 730d will output pulses with the duration of the L longer than that of the H. Therefore, the insert section 702 will rotate in the R direction while continuing a minute rotating vibration and will also retreat while continuing a minute moving vibration.

Likewise, when the joystick 709 is operated obliquely between the advancing (Push) direction and the L rotating direction during the combined operation of a minute rotating vibration and a minute moving vibration, the insert section 702 will rotate in the L direction while continuing a minute rotating vibration and will also advance while continuing a minute moving vibration.

Although the minute bending vibration, minute rotating vibration and minute moving vibration have been explained above, it is needless to say that these vibrations can be performed in any desired combination. It should also be understood that the bending operation can be added during the process of any minute vibration.

Next, (VI) the operation in a combination of a minute rotating vibration and a minute bending vibration shall be described with reference to FIG. 35. For brevity of the explanation, the following shows an example in which a parallel minute vibration mode is set as shown at (f) and the minute rotating and bending vibrations are both set in a narrow angle and low speed mode.

When the minute bending vibration switch 710a and the minute rotating vibration switch 710c are turned on as shown at (a) and (c), the rotating direction indicating circuits 730a and 730d will output pulses in a narrow angle mode as shown at (j) and (p) and the speed controlling circuits 729a and 729d will output pulses in a low speed mode as shown at (i) and (o). Therefore, the insert section 702 will develop a minute bending vibration while continuing a minute rotating vibration. Note that, when the switch 710a or 710c is solely operated, a minute bending vibration or minute rotating vibration will be performed independently as mentioned above.

Now, when the joystick 708 is operated in the U direction as shown at (d) under the condition that the minute bending vibration switch 710a and minute rotating vibration switch 710c are turned on, the rotating direction indicating circuit 730a will output pulses with the duration of the L longer than that of the H as shown at (j). The remaining process is the same as in the case that the joystick 708 is not operated. Therefore, the insert section 702 will be bent in the U direction while continuing both minute rotating vibration and minute bending vibration. Likewise, when the joystick 708 is operated in the D, R or L direction, the insert section 702 will be bent in the D, R or L direction, respectively, while continuing both minute rotating vibration and minute bending vibration.

Next, (VII) the operation upon the change in the conditions of the minute rotating vibration shall be described with reference to FIG. 36.

In a narrow angle and low speed mode as shown at (g) and (h), when the minute rotating vibration switch 710c is turned on as shown at (c), the rotating direction indicating circuit 730d will output pulses in a narrow angle mode as shown at (p) and the speed controlling circuit 729d will output pulses in a low speed mode as shown at (o). Therefore, the insert section 702 will develop a minute rotating vibration in a narrow angle and low speed mode. Now, when the switch 725d is operated to select a high speed mode, the speed controlling circuit 729d will output pulses in a high speed mode as shown at (o). Thus, the pulse frequency will be increased, causing the insert section 702 to develop a minute rotating vibration in a narrow angle and high speed mode.

Further, when the switch 725c is operated to select a wide angle mode, the rotating direction indicating circuit 730d will output pulses in a wide angle mode as shown at (p). Thus, the pulse frequency will be increased, causing the insert section 702 to develop a minute rotating vibration in a wide angle and high speed mode. In addition, when the switch 725d is operated to select a low speed mode, the speed controlling circuit 729d will output pulses in a low speed mode as shown at (o), causing the insert section 702 to develop a minute rotating vibration in a wide angle and low speed mode.

Next, (VIII) the operation in a combination of a minute moving vibration and a minute bending vibration shall be described with reference to FIG. 37. For brevity of the explanation, the following shows an example in which a parallel minute vibration mode is set as shown at (f) and minute moving and bending vibrations are both set in a narrow angle and low speed mode.

When the minute bending vibration switch 710a and the minute moving vibration switch 710b are turned on as shown at (a) and (b), the rotating direction indicating circuits 730a and 730c will output pulses in a narrow angle mode as shown at (j) and (n) and the speed controlling circuits 729a and 729c will output pulses in a low speed mode as shown at (i) and (m). Therefore, the insert section 702 will develop a minute bending vibration while continuing a minute moving vibration. Note that, when the switch 710a or 710b is solely operated, a minute bending vibration or minute moving vibration will be performed independently as mentioned above.

Now, when the joystick 708 is operated in the U direction as shown at (d) under the condition that the minute bending vibration switch 710a and the minute moving vibration switch 710b are turned on, the rotating direction indicating circuit 730a will output pulses with the duration of the L longer than that of the H as shown at (j). The remaining process is the same as in the case that the joystick 708 is not operated. Therefore, the insert section 702 will be bent in the U direction while continuing both minute moving vibration and minute bending vibration. Likewise, when the joy stick 708 is operated in the D, R or L direction, the insert section 702 will be bent in the D, R or L direction, respectively, while continuing both minute moving vibration and minute bending vibration.

Next, (IX) the operation upon the change in the conditions of the minute moving vibration shall be described with reference to FIG. 38.

In a narrow angle and low speed mode as shown at (g) and (h), when the minute moving vibration switch 710b is turned on as shown at (b), the rotating direction indicating circuit 730c will output pulses in a narrow angle mode as shown at (n) and the speed controlling circuit 729c will output pulses in a low speed mode as shown at (m). Therefore, the insert section 702 will develop a minute moving vibration in a narrow angle (short distance) and low speed mode. Now, when the switch 725d is operated to select a high speed mode, the speed controlling circuit 729c will output pulses in a high speed mode as shown at (m). Thus, the pulse frequency will be increased, causing the insert section 702 to develop a minute moving vibration in a narrow angle (short distance) and high speed mode.

Further, when the switch 725c is operated to select a wide angle mode, the rotating direction indicating circuit 730c will output pulses in a wide angle mode as shown at (n). Thus, the pulse frequency will be decreased, causing the insert section 702 to develop a minute moving vibration in a wide angle (long distance) and high speed mode. In addition, when the switch 725d is operated to select a low speed mode, the speed controlling circuit 729c will output pulses in a low speed mode as shown at (m), causing the insert section 702 to develop a minute moving vibration in a wide angle (long distance) and low speed mode.

FIGS. 39 to 44 show behaviors of minute bending vibrations in the UD directions, minute bending vibrations in the RL directions, rightward swing motion, leftward swing motion, minute moving vibration and minute rotating vibration, respectively.

Figure 45:
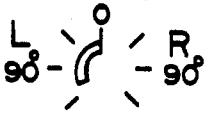

FIG. 45 shows a part of a mode displaying section on the screen of the monitor 740. More specifically, the mode displaying section displays the inserted length and rotating angle of the insert section 702 and the bending angle and bending resistance of the bendable portion 707. The mode displaying section displays also the on/off states of a minute moving vibration, minute rotating vibration and minute bending vibration as well as the mode of a minute bending vibration (that is, a parallel minute vibration, orthogonal minute vibration, leftward swing motion or rightward swing motion). Further, the mode displaying section displays the conditions of the speed (for example, in the three stages of the L, M and H) and the length and angle (for example, in the three stages of the N, M and W) of each minute vibration.

Moreover, the monitor is so arranged that, if the output of the bending resistance detecting circuit 719 exceeds a predetermined critical value, it will give an alarm to stop the respective minute vibrations of the bending, movement and rotation.

With this embodiment, as described above, the insert section 702 will be subjected to a minute vibration for reducing the contact resistance exerted on the insert section 702 and improving the operability of the insertion. The application of a minute bending vibration will cause the rear part of the bendable portion 707 and hence the front end part of the pliable portion 743 to develop a minute vibration for reducing the contact resistance exerted on those parts.

During the minute bending vibration, since the insert section 702 vibrates of itself in the direction crossing the axial direction thereof, even when it is not in contact with the inner wall of the body cavity, the impact against the inner wall of the body cavity will be reduced.

Further, since the conditions of the minute vibration can be appropriately selected for the proper operation depending on the state of an object to be examined into which the insert section is to be inserted or the like, it is possible to reduce the bending resistance exerted on the insert section 702 including the bendable portion 707 without damaging the object to be examined or the like into which the insert section is to be inserted, thus further improving the operability of the insertion.

In addition, since the angle (length) and direction of each minute vibration can be appropriately chosen, the conditions of the optimum minute vibration can be selected depending on the size, configuration or other factors of a tract or cavity as an object into which the insert section is to be inserted. Since the speed of each minute vibration can be appropriately chosen, it is also possible to select a proper speed in accordance with the kind of the disease.

As to the minute bending vibration, since the direction of the minute vibration can be selectively set to be parallel (that is, in the same direction as) or orthogonal to the bending direction and the rightward swing motion and leftward swing motion can be selectively added, it is possible to select the optimum mode depending on the state of the tract or cavity.

Since the respective minute vibrations are turned on/off by the switches 710a to 710c, it is possible to turn off the minute vibration which may possibly perforate a diverticulum region of an organ wall, for example, thereby ensuring a high degree of safety. In an attempt to insert the insert section while closely observing the internal state of the object, for example, a clearer object image free from a blur and noise can be obtained by turning off the minute vibration.

Further, since the minute bending vibration is performed by the motors 712a and 712b used for the bending, it is not required to provide a motor for the minute vibration separately from the bending motor, thereby avoiding an increase in the size and weight of the endoscope.

In addition, the insert section 702 can be subjected to a minute moving vibration and/or minute rotating vibration. Therefore, even when a minute bending vibration is hard to develop or has no effect, for example, the contact resistance exerted on the insert section 702 will be able to be reduced to improve the operability of the insertion by effecting a minute moving vibration and/or minute rotating vibration.

In an orthogonal minute vibration mode of a minute bending vibration, even when the bending is ceased halfway, it will be able to be surely continued. More specifically, in the case that the bending is ceased halfway, the bendable portion 707 will be subjected to the tension in the direction opposite the bending direction and therefore a large actuating torque will be required at the time of resuming the bending. Accordingly, the bending may become hard to resume and perform in such case. Nevertheless, by imparting a minute vibration to the bendable portion 707 in the direction orthogonal to the bending direction, the bending can be easily resumed.

Since the bendable portion 707 can be bent while applying various forms of minute vibrations, it is possible to insert the bendable portion 707 along a bent tract or cavity while developing a desired minute vibration and to improve the operability of the insertion through a bent object in particular.

Further, either one or both of the movement and rotation of the insert section 702 can be performed by the joystick 709 with the result of a very high operability.

Since one or more of such various forms of minute vibrations as minute bending vibrations (a parallel minute vibration, orthogonal minute vibration, rightward swing motion and leftward swing motion), a minute moving vibration of the insert section and a minute rotating vibration of the insert section can be operated in combination, it is possible to select the optimum depending on the state of the tract or cavity.

Each minute vibration is only needed to develop at least one cycle of the minute vibration (reciprocal motion). It is preferable that the angle of each minute vibration except a minute moving vibration is in a range of 1 to 180 degrees, the length of a minute moving vibration is in a range of 1 to 5 cm, the speed of each minute vibration except a minute moving vibration is in a range of 1 to 90 degrees/sec and the speed of a minute moving vibration is in a range of 1 to 50 mm/sec. However, the above respective ranges may be appropriately modified at the operator's discretion.

When a minute vibration is set in an extremely high speed mode or an extremely wide angle mode, the resulting visual field and angle of view of the endoscope will make it very hard to observe the object image. In such case, the image quality will be able to be improved by properly utilizing a freezing function so as to give an intermittent display.

In addition, by displaying various minute vibration modes and other parameters on the same screen as of the observed image, as shown in FIG. 45, the conditions of the respective minute vibrations can be confirmed at a glance, resulting in a higher operability.

The speed of each minute vibration may be changed gradually from a low speed to a high speed or the angle of each minute vibration may be changed gradually from a narrow angle to a wide angle. Also, the minute bending vibration may be shifted from the vertical direction to the horizontal direction or from a rightward swing motion to a leftward swing motion.

Finally, the insert section 702 may be so arranged as to return to the state prior to the minute vibration when the minute vibration switch is turned off.

Figure 46:
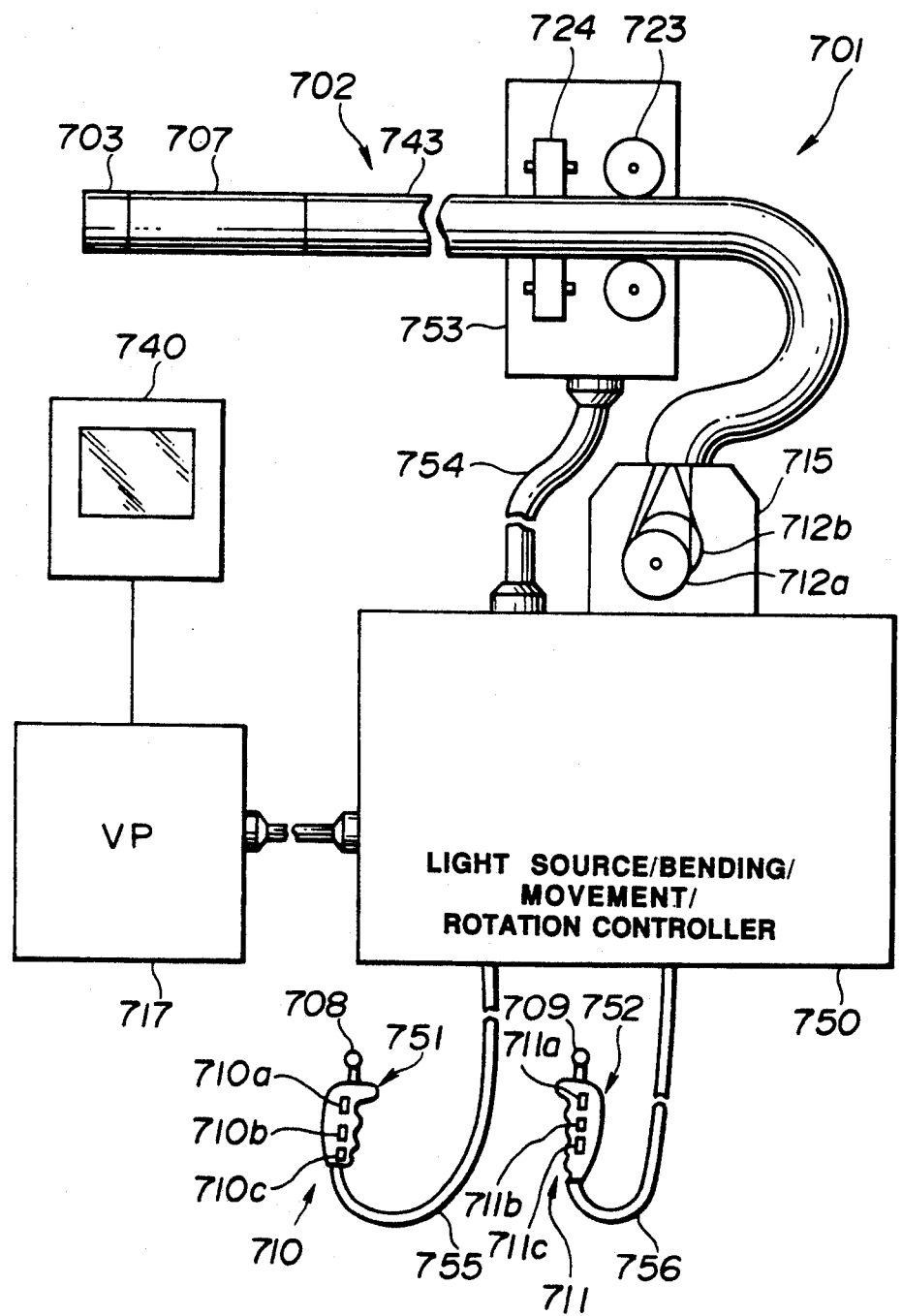
Figure 47:
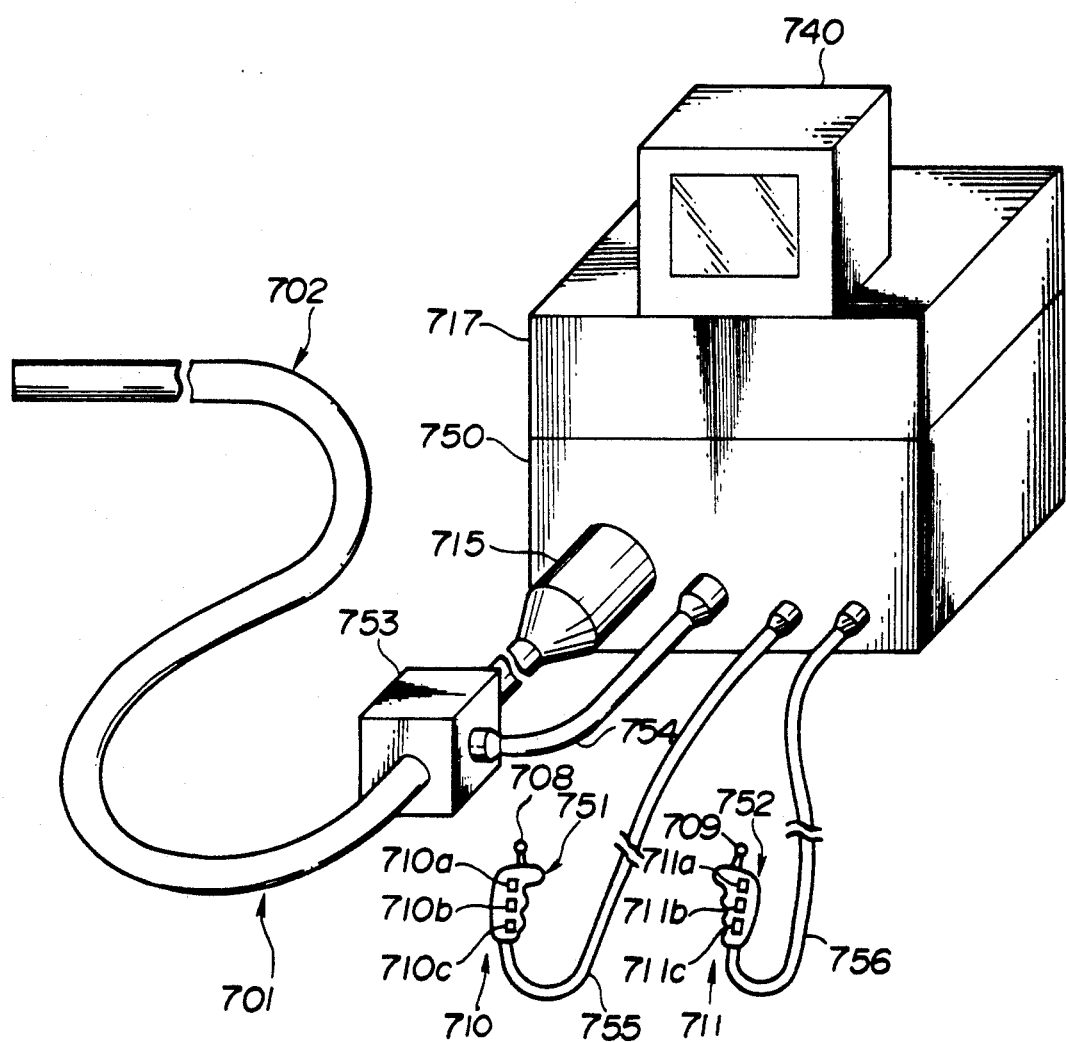

FIGS. 46 and 47 illustrate the eighth embodiment of the present invention.

Note that the same components as in the seventh embodiment shall be represented by the same reference numerals and shall not be explained here.

As shown in FIG. 47, an endoscope system of this embodiment comprises an endoscope 701, a light source and bending/movement/rotation controller 750 to which this endoscope 701 is connected, a VP 717 connected to the controller 750, a monitor 740 connected to the VP 717 and a movement/rotation device 753 attached to an insert section 702 of the endoscope 701.

The endoscope 701 of this embodiment includes no operating section and a connector 715 is directly provided at the base end of the insert section 702. As will be seen from FIG. 46, motors 712a and 712b are provided in the connector 715 which is connectable to the light source and bending/movement/rotation controller 750. This controller 750 includes the bending/movement/rotation controlling circuit 720, bending angle detecting circuit 718, bending resistance detecting circuit 719, lamp 722 and switch 725 in the above mentioned seventh embodiment. Thus, the controller 750 has the same structure as of the controller 716 of the seventh embodiment. The VP 717 is connectable to the controller 750. A bending operating unit 751 and a movement/rotation operating unit 752 are also connected to the controller 750 through coupling cables 755 and 756, respectively. The bending operating unit 751 includes a joystick 708 and switch 710. The movement/rotation operating unit 752 includes a joystick 709 and switch 711.

The movement/rotation device 753 is attached to the insert section 702, includes the movement rollers 723, motor 723a, rotation rollers 724 and motor 724a in the seventh embodiment and is connectable to the controller 750 through a coupling cable 754.

It is to be noted that the connectors provided at the ends of the coupling cables between the respective components can be freely attached and detached.

With this embodiment, since the motors 712a and 712b are provided in the connector 715, it is not required to provide an operating section midway in the insert section 702. This eliminates the need of gripping the heavy operating section incorporating motors and others and requires only to grip the lighter operating units 751 and 752, thereby facilitating the operation.

Where the movement/rotation device 753 is not provided, it is possible to perform the bending alone. In this case, the bending can be performed, for example, by holding the operating unit 751 by the left hand and the insert section 702 by the right hand.

In case the movement/rotation device 753 is provided, the operating units 751 and 752 will be able to be operated while being held by the respective hands, resulting in a very high operability. By holding the bending operating unit 751 by the left hand and the movement/rotation operating unit 752 by the right hand, for example, the operator can perform the bending in a familiar manner, because this allotment of the roles to the respective hands is approximate to that usually practiced in the manual operation, that is, the left hand manipulating a bending operating knob and the right hand moving and rotating (twisting) the insert section.

Moreover, in case the movement/rotation device 753 is not provided, it will be further possible to motorize only the bending operation. Needless to say, a minute bending vibration is also possible.

The other structures, operations and effects are the same as in the seventh embodiment.

Figure 48:
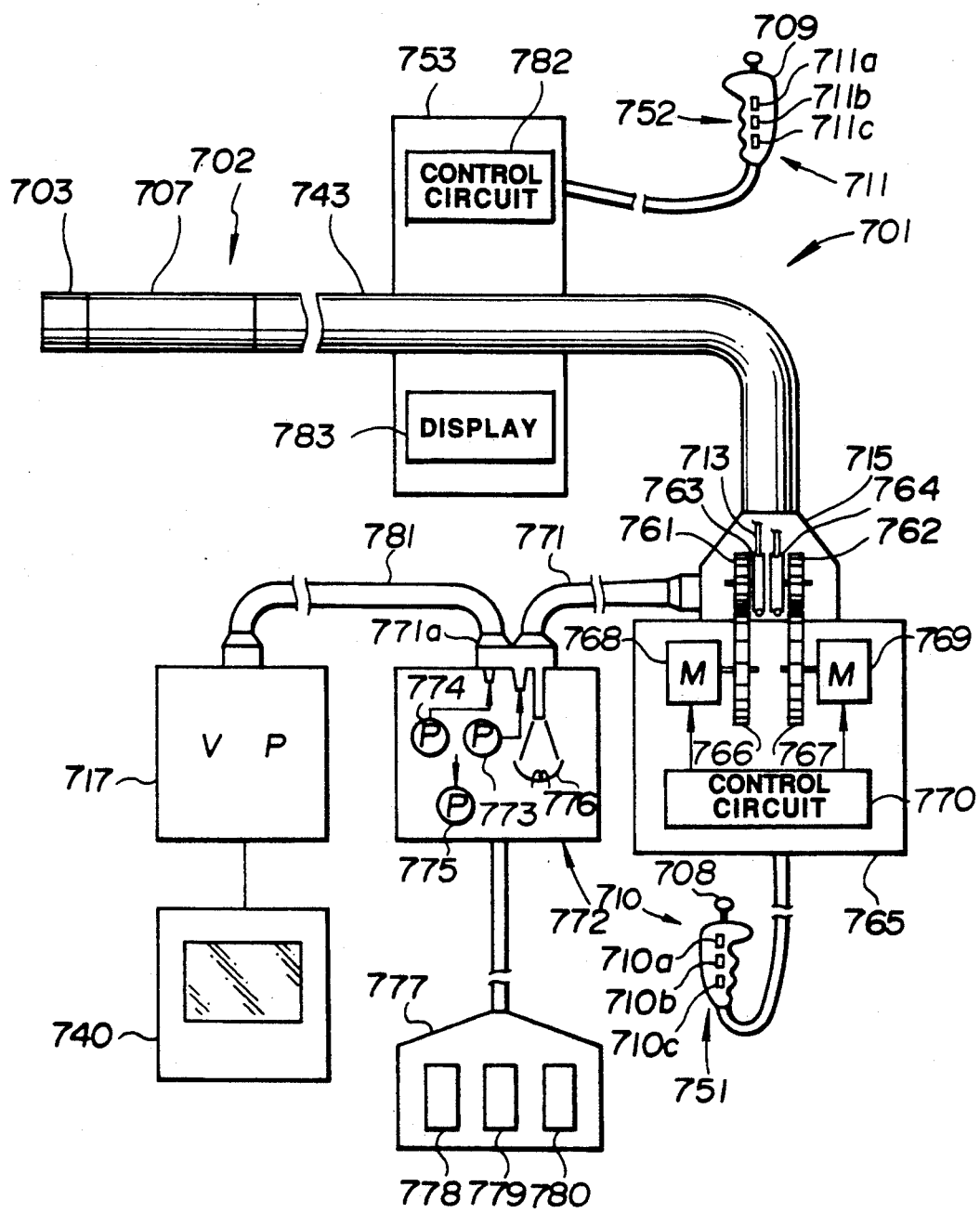
FIGS. 48 and 49 relate to the ninth embodiment of the present invention.
Figure 49:
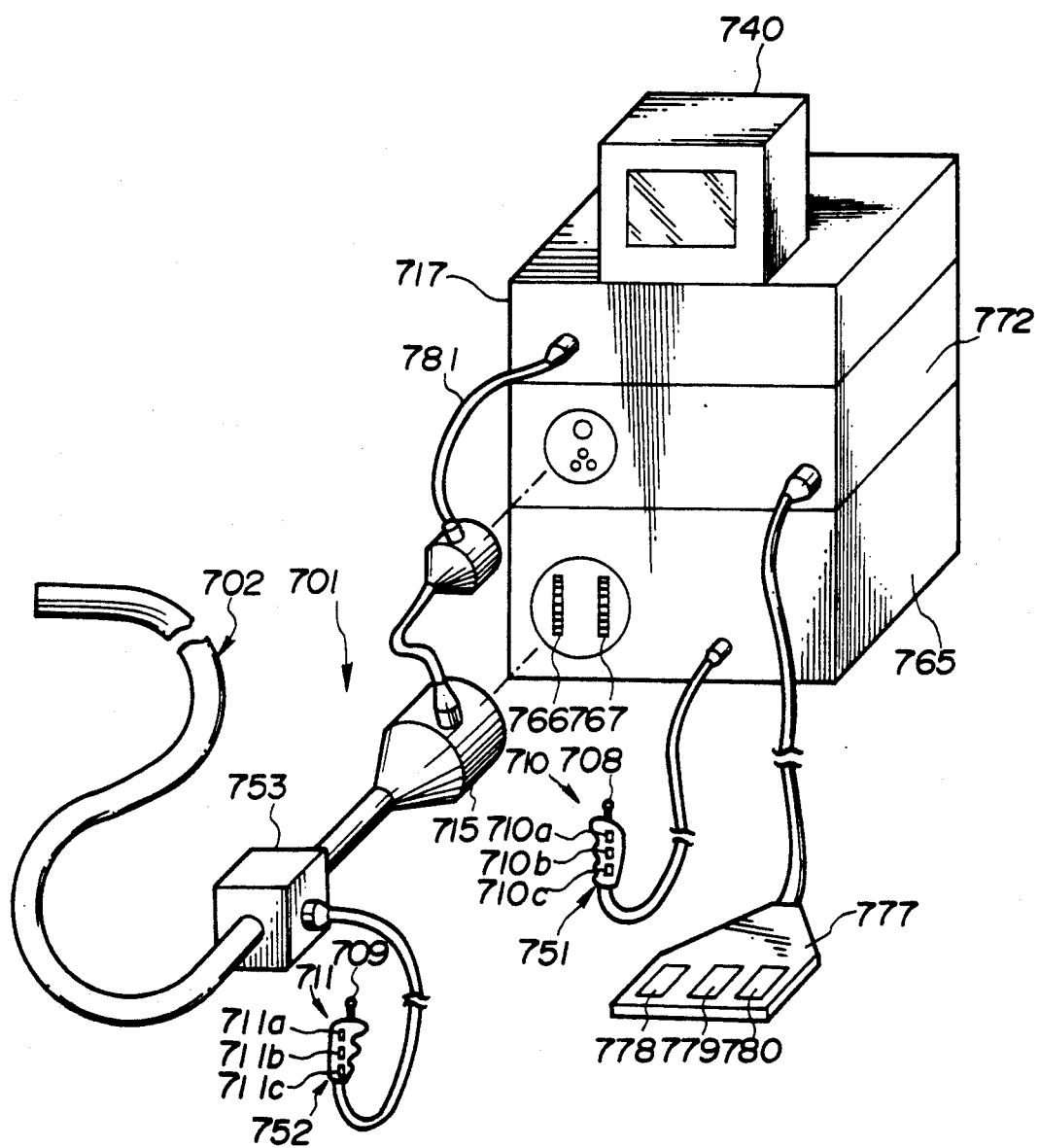

FIGS. 48 and 49 illustrate the ninth embodiment of the present invention.

Note that the same components as in the seventh and eighth embodiments are represented by the same reference numerals and shall not be explained here.

As shown in FIG. 49, an endoscope system of this embodiment comprises an endoscope 701, a bending device 765 connected to the endoscope 701, a light source unit 772, a VP 717, a monitor 740 connected to the VP 717 and a movement/rotation device 753 attached to an insert section 702.

The endoscope 701 of this embodiment includes no operating section as in the seventh embodiment and a connector 715 is directly provided at the base end of the insert section 702. As will be seen from FIG. 48, transmission gears 761 and 762 are provided in the connector 715 and pulleys 763 and 764 are mounted on rotary shafts of the transmission gears 761 and 762, respectively. A bending wire 713 is attached to each of the pulleys 763 and 764. On the other hand, the bending device 765 includes motors 768 and 769, transmission gears 766 and 767 mounted on output shafts of the motors 768 and 769, respectively, and a controlling circuit 770 for controlling the motors 768 and 769. Under the condition that the connector 715 is connected to the bending device 765, the gears 761 and 762 in the connector 715 mesh with the gears 766 and 767, respectively, in the bending device 765. Also connected to the bending device 765 is a bending operating unit 751 the same as in the seventh embodiment. The controlling circuit 770 drives the motors 768 and 769 depending on the operation of the bending operating unit 751 to control the bending (including a minute bending vibration) as explained in the seventh embodiment.

The connector 715 is also connectable to the light source unit 772 through a coupling cable 771. The light source unit 772 incorporates an air feeding pump 773, water feeding pump 774, suction pump 774 and lamp 776. A foot switch 777 is connected to the light source unit 772. Treading on pedals 778, 779 and 780 of the foot switch 777 actuates air feeding, water feeding and suction, respectively.

A coupling cable 781 is extended from a connector 771a of the above mentioned cable 771 on the same side as of the light source unit 772 and is connectable to the VP 717.

Further, connected to the movement/rotation device 753 is a movement/rotation operating unit 752 the same as in the eighth embodiment. The movement/rotation device 753 incorporates a controlling circuit 782 and has a display 783. The controlling circuit 782 drives movement motors 723a and rotation motors 724a depending on the operation of the movement/rotation operating unit 752 to control the movement and rotation including a minute moving vibration and minute rotating vibration explained in the seventh embodiment. The display 783 displays the inserted length of the insert section 708, the rotating angle of the insert section 702, the on/off state of the minute moving vibration, the speed (L, M and H) of the minute moving vibration, the length (N, M and W) of the minute moving vibration, the on/off state of the minute rotating vibration, the speed (L, M and H) of the minute rotating vibration and the angle (N, M and W) of the minute rotating vibration.

Meanwhile, the monitor 740 displays the bending angle, the bending resistance, the on/off state of the minute bending vibration, the speed (L, M and H) of the minute bending vibration and the angle (N, M and W) of the minute bending vibration.

In this embodiment, as the foot switch 777 is provided, feeding air, feeding water and suction can be controlled by using the foot switch 777 even while the operating units 751 and 752 are gripped by respective hands.

In case only the movement/rotation device 753 is provided in a usual endoscope of a manually bending type, it will be possible to motorize the operation of the movement and rotation and to develop a minute moving vibration and minute rotating vibration.

In this embodiment, since the bending device 765 and the movement/rotation device 753 are separate units, it is possible to use either one or both of the devices 765 and 753 in a sole or combined manner as required.

Furthermore, since the bending motors 712a and 712b are not present in the endoscope body, the endoscope can be reduced in the weight and cost.

The other structures, operations and effects are the same as in the seventh and eighth embodiments.

Figure 50:
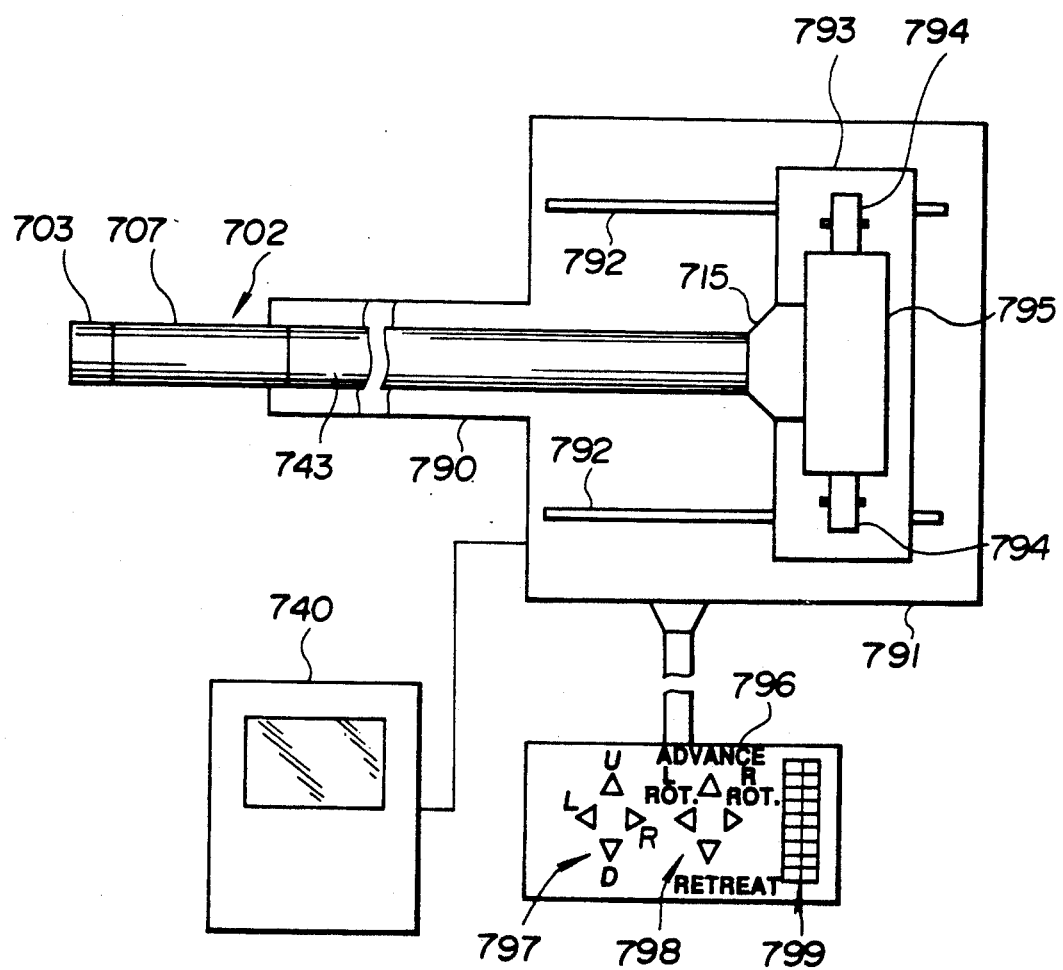
FIGS. 50 and 51 relate to a modification of the ninth embodiment.
Figure 51:
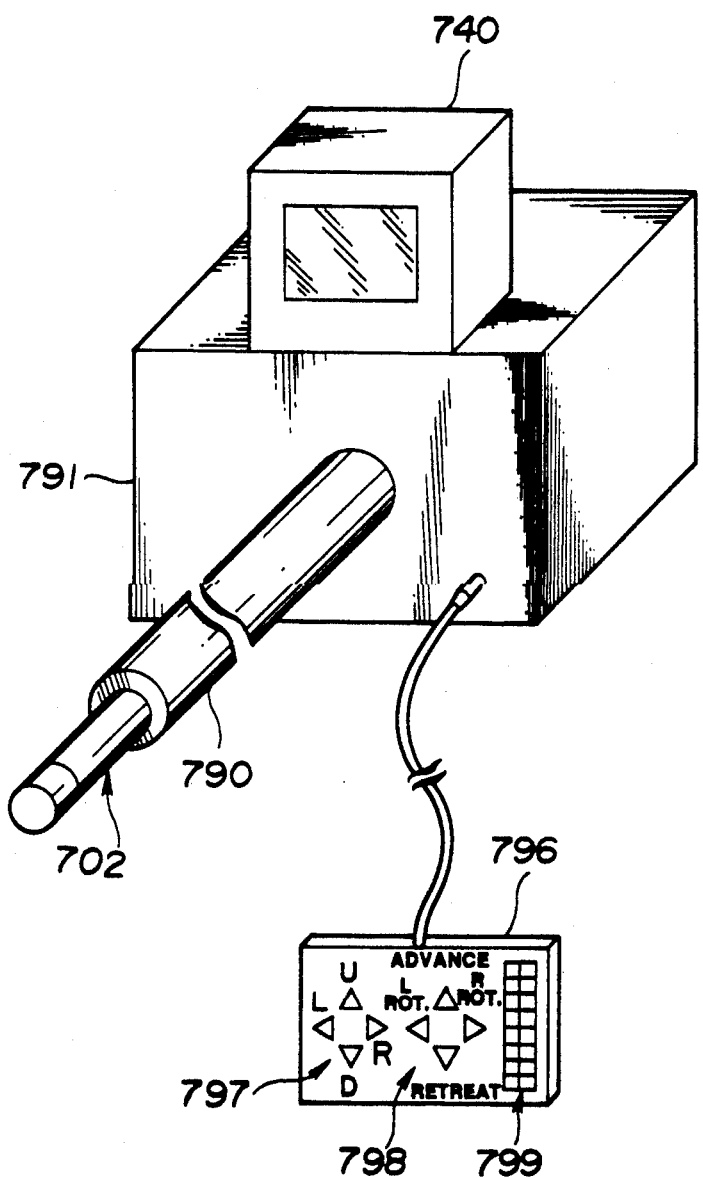

FIGS. 50 and 51 illustrate a modification of the ninth embodiment of the present invention.

Note that the same components as in the seventh embodiment are represented by the same reference numerals and shall not be explained here.

In an endoscope apparatus of this modification, an insert section 702 is introduced into an insertion opening of an object to be examined by using a pliable guide 790 which is cylindrical in the shape and is connected at the base end to a centralized controller 791. This controller 791 is provided with a pair of parallel rails 792 extending in the axial direction of the insert section 702 and a base 793 movable to advance and retreat as guided by the rails 792. A rotatable drum 794 is provided on the base 793. A bending/light source/VP unit 795 is supported by the drum 794 in a rotatable manner.

The bending/light source/VP unit 795 incorporates the bending device 765, light source unit 772 and VP 717 of the ninth embodiment together. As in the eighth embodiment, the connector 715 houses therein transmission gears and is freely connectable to the unit 795.

A control box 796 is removably connected to the unit 795 and is provided with bending buttons 797 corresponding to the U, D, R and L directions, insert section movement/rotation buttons 798 and minute bending-/moving/rotating vibration controlling switches 799.

The guide 790 is cylindrical in the shape and can be split into two parts.

The operation of this embodiment when any one of the bending buttons 797 is depressed is the same as in the ninth embodiment and shall not be explained here. When one movement switch of the movement/rotation buttons 798 is depressed, the base 793 will advance or retreat along the rails 792. At this time, the pressure of the guide 790 will prevent the insert section 702 from slacking. When one rotation switch of the movement-/rotation buttons 798 is depressed, the drum 794 will be rotated, causing the entire unit 795 and the insert section 702 to rotate.

A minute bending vibration, minute moving vibration and minute rotating vibration are made respectively the same as in the seventh to ninth embodiments and shall not be explained here.

In this modification, since the endoscope and the device for driving the endoscope are made integral together, the handling will be facilitated during the operation. Also, by the provision of the guide 790, the insert section is prevented from slacking.

Furthermore, since the control box 796 is of a push button type, it can be operated by a single finger.

The other structures, operations and effects are the same as in the seventh or ninth embodiment.

As shown in FIG. 52, an endoscope system 901 of the tenth embodiment comprises an electronic endoscope 902, a controlling unit 905 incorporating a light source unit 903 feeding an illuminating light beam to the electronic endoscope 902, motor controlling unit 924 and bending angle detecting circuit 925, a CCU 904 and a monitor 906 for displaying a reference video signal produced from the CCU 904.

The electronic endoscope 902 comprises an insert section 907 which is so flexible and elongate as to be allowed to be inserted into a body cavity or the like, a larger diameter operating section 908 formed at the rear end of the insert section 907, a universal cord 909 extended laterally from the operating section 908 and a connector 911 provided at the end of the universal cord 909. The connector 911 is freely connectable to the video processor 905 in a removable manner.

The insert section 907 comprises a rigid distal end component 913 in which a CCD 912 and others are disposed, a bendable portion 914 provided adjacently to the distal end component 913 on the rear side and an elongate flexible tube portion 915 provided at the rear end of the bendable portion 914.

A light guide 916 for transmitting an illuminating light is extended through the insert section 907, operating section and universal cord 909. Thus, under the condition that the connector 911 is connected to the controlling unit 905, the illuminating light emitted from a lamp 917 in the light source unit 903 is fed to the end face of the light guide 916. The light guide 916 transmits the illuminating light emitted from the lamp 917 and radiates it forward from the end face of the distal end component 913. An optical image of an object irradiated with the radiated light is focused by an objective lens 918 provided in the distal end component 913 on the CCD 912 located in the focal plane of the objective lens 918. A color mosaic filter 919 for separating colors is attached to the imaging plane of the CCD 912 to separate colors for respective pixels. A signal photoelectrically converted by the CCD 912 is input through a cable extended from the connector 911 into the CCU 904 which executes various steps of processing the signal to convert it to a reference video signal. On the basis of this video signal, the object image is displayed in the monitor 906.

The operating section 908 of the electronic endoscope 902 is provided with an air feeding/water feeding switch button 921, a suction switch button 922 and a set of bending switches 923.

The set of bending switches 923 includes an upward switch button 923a, downward switch button 923b, leftward switch button 923c and rightward switch button 923d.

When one of the bending switches 923 is depressed to bend the bendable portion 914, the motor controlling unit 924 and bending angle detecting circuit 925 both in the controlling unit 905 will be operated to control a driving motor for bending the bendable portion 914 and to detect a bending angle.

As shown in FIG. 53, a bending actuator is assembled in the operating section 908.

Within a case 926 of the operating section 908, there are disposed two sets of frame assemblies 929 (only one of them is shown in FIG. 53) which are positioned laterally symmetrically with each other and each of which comprises a main frame 927 and a sub-frame 928 arranged parallel with each other with a space defined between them.

A bending actuator 931 for the vertical (upward/-downward) bending is mounted on one frame assembly 929, while another bending actuator (not shown) for the horizontal (rightward/leftward) bending is mounted on the other frame assembly 929.

The bending actuator 931 for the vertical bending shown in FIG. 53 shall be explained in detail in the following.

A DC motor 932 is mounted on the sub-frame 928 supported by the main frame 927. A driving gear 934 is secured to a driving shaft 933 of the DC motor 932 by a press fit or the like and is held in mesh with a driven gear 935 on the side of the driving gear 934 opposite the insert section 907, thereby forming a transmission gear train 936.

The driven gear 935 is rotatably attached to a shaft 937 and is coaxially joined with a sprocket 938 which is rotatably supported on the shaft 937 near the main frame 927. The shaft 937 is fixed and screwed to the sub-frame 928 so that the driven gear 935 and the sprocket 938 may be rotated together around the shaft 937.

The sprocket 938 constitutes a rotatable member for the pulling operation and a chain 939 is entrained around the sprocket 938. Around the outer periphery of the chain 939 entrained around the sprocket 938, chain guides 941 and 942 for guiding and preventing the chain 939 from slipping out of the sprocket 938 are fixed and screwed to the main frame 927.

As shown in FIG. 54, the chain 939 entrained around the sprocket 938 is coupled at both ends with bending wires 944 through joint pieces 943, respectively. Thus, the chain 939, joint pieces 943 and bending wires 944 jointly constitute a pulling member. These bending wires 944 are extended through the insert section 907 and are coupled with the bendable portion 914 at the front end or with the distal end component 913 at the rear end. As the sprocket 938 rotates, the bending wires 944 will be pushed and pulled (or loosened and tensioned) depending on the rotating direction of the sprocket 938 so that one wire 944 may be pushed and the other wire 944 may be pulled, thereby bending the bendable portion 914.

Further, as shown in FIG. 53, a partition 945 is provided between the chain 939 and the transmission gear train 936 to prevent the chain 939 from striking against the transmission gear train 936.

Moreover, in order to prevent the transmission gear train 936 from striking directly against the sub-frame 928, a cushioning member 946 is fitted around the shaft 937 in a position between them.

In this example, as shown in FIG. 54, a means for detecting the bent amount of the bendable portion 914, that is, a differential transformer 951 constituting a bent amount sensor is disposed in a space defined between the sprocket 938 and both ends of two runs of the chain 939 entrained around the sprocket 938 and extending substantially parallel with each other with a spacing or distance corresponding to the diameter of the sprocket 938 between them. The differential transformer 951 is fixed and screwed to the main frame 927 as shown in FIG. 53.

The differential transformer 951 has a coil unit 954 which comprises a primary coil 952 having a substantially cylindrical outer configuration and a pair of secondary coils 953 each provided on either side of the primary coil 952. The central axis of the coil unit 954 is arranged substantially parallelly with the direction in which the chain 939 is moved. A core 955 is located inside the coil unit 954 and is fixed to the distal end of an L-shaped arm 956 which is in turn fixed to one bending wire 944 by soldering or the like. When the bending wire 944 moves as indicated by the arrow A, the core 955 will be also moved as indicated by the arrow B as operatively connected with the movement of the bending wire 944 in the same direction and by the same distance.

The coil unit 954 of the differential transformer 951 is connected to the bending angle detecting circuit 925 in the video processor 905. By applying a voltage of a constant frequency to the primary coil 952 and detecting a difference between the respective voltages induced in the secondary coils 953, the bending angle detecting circuit 925 can determine the direction and distance of the movement of the core 955, that is, the direction and distance of the movement of the bending wire 944 on the basis of the polarity and extent of the detected voltage difference. The bending angle detecting circuit 925 calculates the bending angle (bent amount) of the bendable portion 911 from the above direction and distance of the movement of the core and displays it in the monitor 906.

In addition, the set of bending switches 923 and DC motors 932 (only one of them is shown in FIG. 53) is connected to the motor controlling unit 924. Depending on one of the bending switches 923 being operated, the motor controlling unit 924 feeds a driving current necessary for a desired control including the rotating direction of the DC motors 932.

The operation of this first example shall be described below.

After the insert section 907 of the electronic endoscope 902 is inserted into a body cavity, when it is desired to bend the bendable portion 914 upward, the operator will depress the upward switch button 923a in the set of the bending switches 923.

When the switch is operated, the DC motor 932 will be rotated to rotate the driving gear 934 secured to the driving shaft 933 of the DC motor 932, whereby the driven gear 935 meshed with the driving gear 934 and the sprocket 938 rotatable together with the driven gear 935 will be rotated. When the sprocket 938 rotates, the chain 939 will be turned to pull the upper bending wire 944 to one end of the chain 939 and will let out the lower bending wire 944. As a result, the bendable portion 911 will be forcibly bent upward.

When the upper bending wire 944 is pulled to move in either direction, the arm 956 secured at one end to the wire 944 will be also moved in the same direction so that the core 955 fixed to the arm 956 will be moved through the coil unit 954 as operatively connected.

When the core 955 moves, the degree of electromagnetic coupling between the primary coil 952 and the two secondary coils 953 will be changed to produce a potential difference between the two secondary coils 953 which difference will be proportional to the displaced amount of the core 955. This potential difference is detected by the bending angle detecting circuit 925 and is then converted to the direction and distance of the movement of the bending wire 944. On the basis of this distance of the movement, the bending angle is determined through an arithmetic process and is displayed in the monitor 906.

In this embodiment, since the differential transformer 951 as a sensor for detecting the bent amount of the bendable portion 914 is disposed in a space defined in a position adjacent to the sprocket 938 as a rotatable member for operating the pulling member and in a region between both ends of two runs of the chain 939 extending substantially parallel with each other and coupled respectively with the bending wires 944, the bent amount sensor can be stored without increasing the size of the operating section 908. Accordingly, it is possible to prevent the reduction in the operability.

Although the DC motor 932 is used as a driving means for driving the sprocket 938 to rotate in the tenth embodiment, the driving means is not limited to the DC motor but may be any other rotary type motor such as an ultrasonic motor, stepping motor or AC motor.

Figure 55:
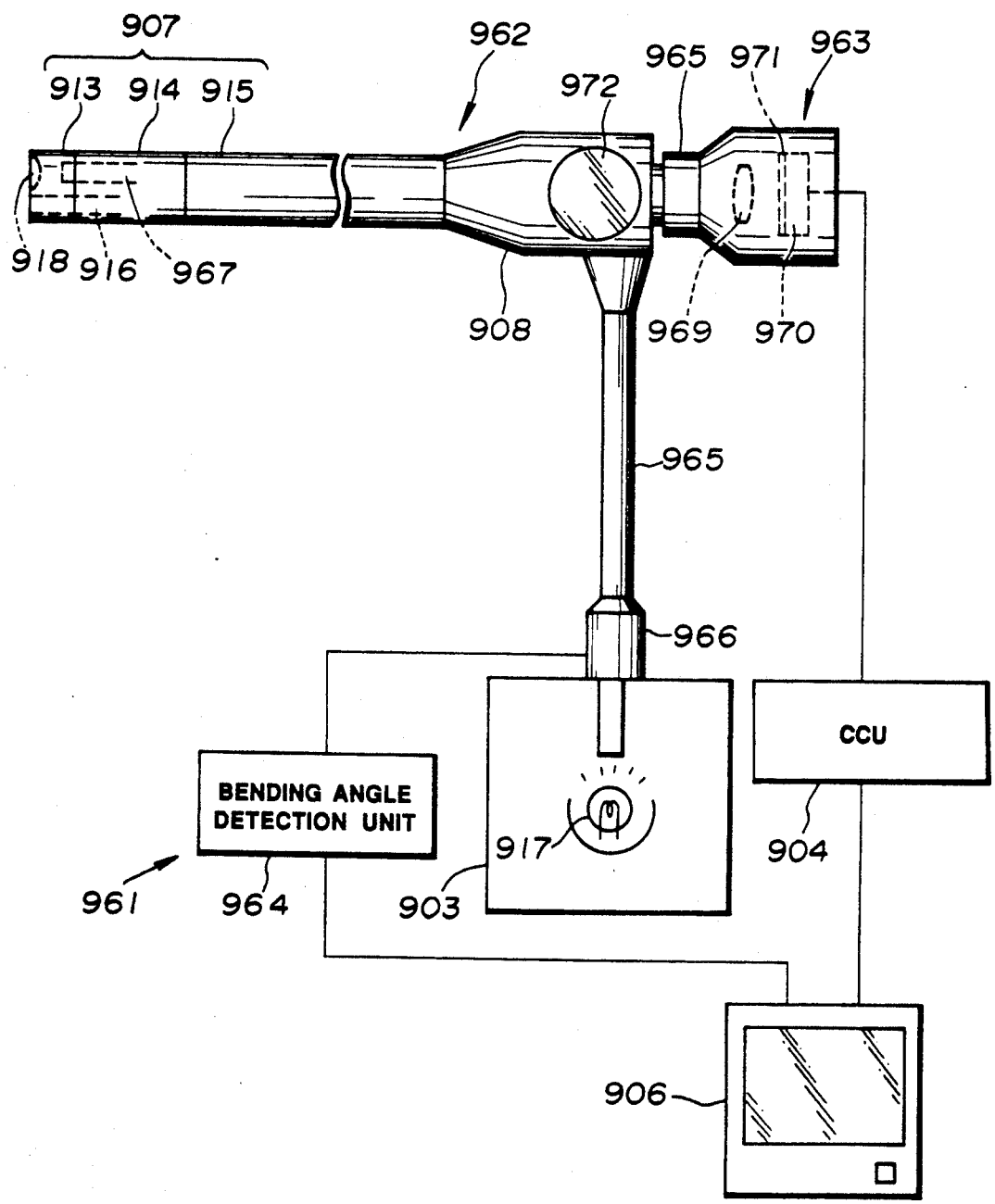
FIG. 55 is a general formation diagram of the eleventh embodiment.

FIG. 55 illustrates the eleventh embodiment.

Note that the same components as in the tenth embodiment are represented by the same reference numerals. An endoscope system 961 of this eleventh embodiment comprises a fiber scope 962, a mounted type television (TV) camera 963 fitted to the fiber scope 962, a light source unit 903 for feeding an illuminating light beam to the fiber scope 962, a CCU 904 for processing a signal from the TV camera 963, a monitor 906 for displaying a video signal produced by the CCU 904 and a bending angle detecting unit 964 for detecting the bent amount of a bendable portion 914.

As in the electronic endoscope 902, the fiber scope 962 has an insert section 907 comprising a distal end component 913, the bendable portion 914 and a flexible tube portion 915 and an operating section 908. An eyepiece portion 965 is formed at the rear end of the operating section 908 and the TV camera 963 is removably fitted to the eyepiece portion 965.

A light guide 916 is extended through the insert section 907 of the fiber scope 962 and further through a light guide cable 965 which is extended out of the operating section 908. By connecting a connector 966 to the light source unit 903, the illuminating light of a lamp 917 is fed to the light guide 916.

An objective lens 918 is attached to the distal end component 913 of the insert section 907 and the front end face of an image guide 967 is located in the focal plane of the objective lens 918. The image guide 967 serves to transmit an optical image to the rear end face thereof located in the eyepiece portion 965. An eyepiece lens is disposed opposite the rear end face of the image guide 967 so that the operator may observe with the naked eye the optical image transmitted and magnified through the eyepiece lens.

Further, a focusing lens 969 is disposed in the TV camera 963 so as to focus an optical image onto a CCD 970. A mosaic filter 971 for separating colors is attached to the imaging plane of the CCD 970.

A bending controlling knob 972 is provided on the operating section 908 of the fiber scope 961. By turning the knob 972, the bendable portion 914 can be bent manually.

Figure 56:
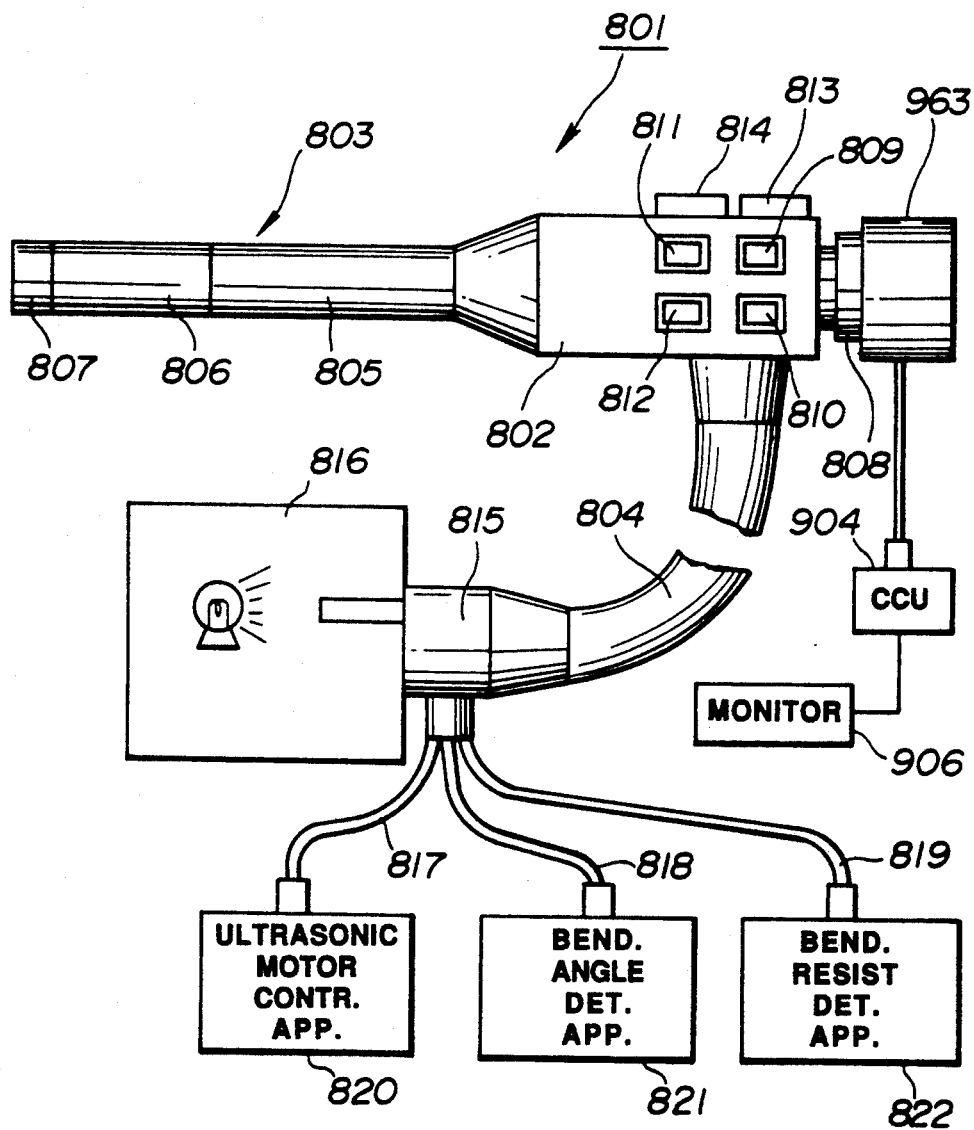
FIGS. 56 and 57 relate to the twelfth embodiment of the present invention.

FIG. 56 shows the twelfth embodiment of the present invention.

As shown in FIG. 56, an endoscope 801 is provided with an elongate and flexible insert section 803 and a larger diameter operating section provided at the rear end of this insert section 803. The above mentioned insert section 803 comprises a rigid distal end component 807, a bendable portion 806 and a flexible tube portion 805 in the order from the distal end side. An eyepiece portion 808 is provided at the rear end of the above mentioned operating section 802. A flexible universal cord 804 is extended sidewise from the above mentioned operating section 802 and is provided at the end with a connector 815 which is to be connected to a light source apparatus 815. Three branch cords 817, 818 and 819 are extended out of the above mentioned connector 815 and are to be connected respectively to an ultrasonic motor controlling apparatus 820, bending angle detecting apparatus 821 and bending resistance detecting apparatus 822.

The above mentioned operating section 802 is provided with bending controlling switches 809, 810, 811 and 812 corresponding respectively to the up, down, right and left directions, a suction switch 813 and an air feeding and water feeding switch 814.

The above mentioned distal end component 807 is provided with an illuminating window and observing window. A light distributing lens not illustrated is fitted inside the above mentioned illuminating window. A light guide consisting of a fiber bundle not illustrated is connected to this light distributing lens at the rear end, is inserted through the insert section 803, operating section 802 and universal cord 804 and is connected to the connector 815. An illuminating light emitted from a light source lamp within the above mentioned light source apparatus 816 enters the entrance end of this light guide. An objective lens system not illustrated is fitted inside the above mentioned observing window. The distal end face of an image guide consisting of a fiber bundle not illustrated is disposed in the image forming position of this objective lens system. This image guide is inserted through the insert section 803 and is extended at the rear end to the above mentioned eyepiece portion 808. An object image formed by the above mentioned objective lens system is led to the eyepiece portion 808 by the image guide and can be observed from this eyepiece portion 808. A TV camera 963 can be removably connected to this eyepiece portion 808 and is connected with a CCU 904 through a cable. A video signal processed by this CCU 904 is displayed in a monitor 906.

Figure 57:
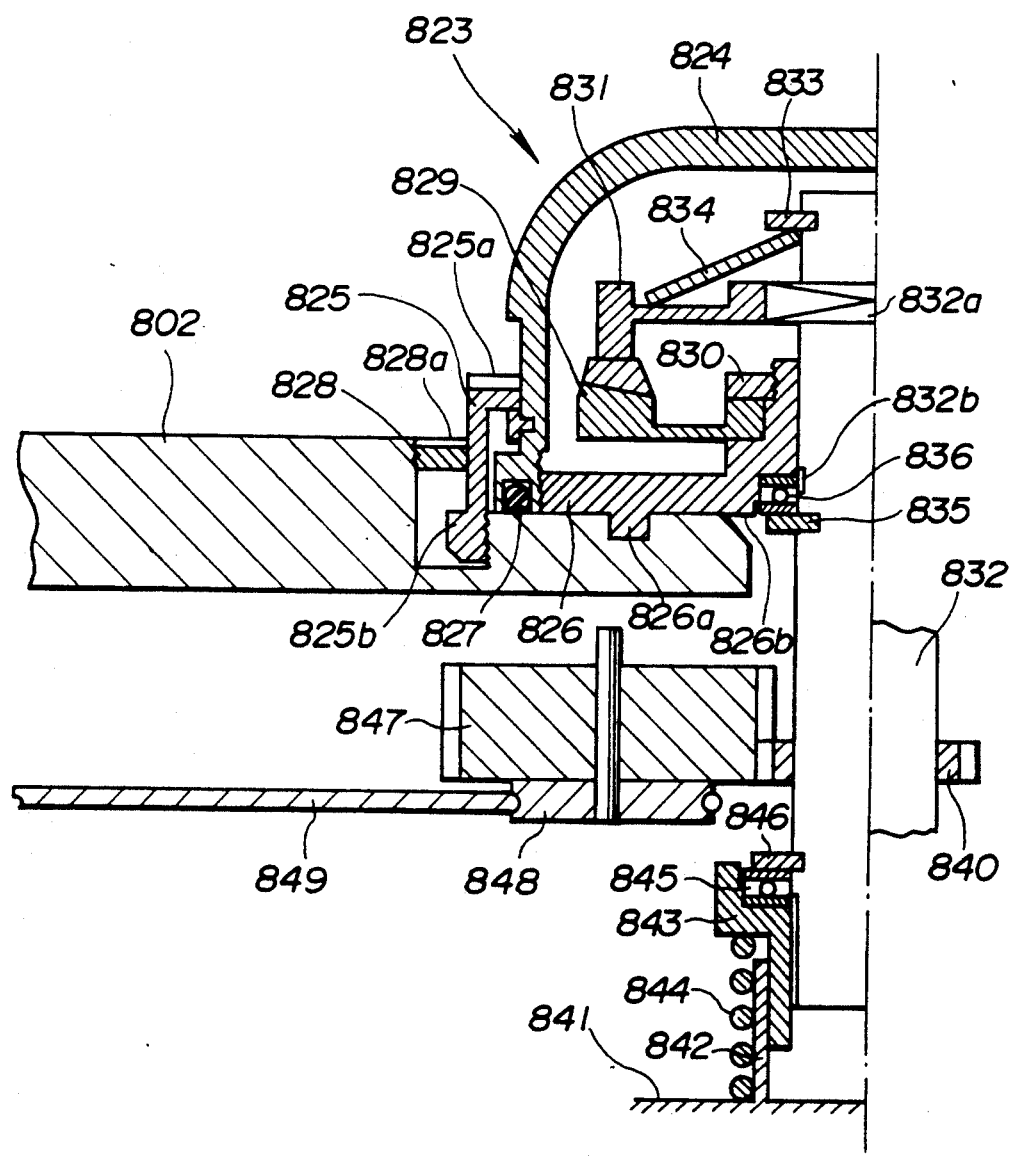

The above mentioned operating section 802 is provided on the back side of the paper surface with a motor unit 823 which has an ultrasonic motor as a driving means. As shown in FIG. 57, a housing 824 of the above mentioned motor unit 823 is fixed to the operating section 802 through a ring screw 825. An O-ring 827 for holding a water-tightness is fitted between this housing 824 and the operating section 802. The above mentioned housing 824 is screwed in the lower part to a base 826 which is prevented by engaging a projection 826a on the lower surface with a recess provided in the operating section 802 from rotating with respect to the operating section 802. The above mentioned ring screw 825 is provided on the upper surface with a slit 825a so as to be rotatable with a divider or the like not illustrated. A flange part 825b is formed on the outer periphery of the lower part of the above mentioned ring screw 825. A ring screw 828 screwed to the operating section 802 is provided in the position with which the flange part 825b rises to be in contact with the rotation of the ring screw 825 and is provided on the upper surface with a slit 828a so as to be rotatable.

A stator 829 is mounted on the central upper part of the above mentioned base 826 and is fixed with a nut 830. A rotor 831 is provided on the upper part of the above mentioned stator 829 and is provided in the center part with a square hole in which is fitted a square part of a shaft provided through the above mentioned base 826, stator 829 and rotor 831. A snap ring 833 is provided in the upper part of the above mentioned shaft 832. A dish spring 834 is provided between this snap ring 833 and the upper surface of the above mentioned rotor 831 so that the rotor 831 may be biased to the stator 829 side by this dish spring 834. A snap ring 835 is provided in the halfway part of the above mentioned shaft 832 and supports a thrust bearing 836 provided between the base 826 and shaft 832. By the way, recesses 832b and 826b for the thrust bearing 836 are provided respectively on the shaft 832 and base 826. On the above mentioned shaft 832, a gear 840 is secured as by shrink fit in the through hole within the operating section 802.

On the other hand, an annular projection 842 is provided on a frame 841 within the operating section 802. A cylindrical guide 843 is slidably inserted into this annular projection 842 and is biased upward by a spring 844. A thrust bearing 845 rotatably supporting the above mentioned shaft 832 is fitted to a step formed on this guide 843 and is prevented by a snap ring 846 provided on the shaft 832 from being pulled out.

The above mentioned gear 840 meshes with a gear 847 provided within the operating section 802. A bending operating wire 849 is wound around a pulley 848 integral with this gear 847. BY the way, the above mentioned gear 847 is wider than the gear 840 so that, even if the gear 840 moves up and down, it will be able to mesh with the gear 847.

Now, in the state shown in FIG. 57, the bending operating wire 849 is drivable by an ultrasonic motor and the rotor 831 is pressed against the stator under a weight, for example, of 7 kg by the energizing force of the dish spring 834 so that, when sine waves and cosine waves of voltages different in the phase by 90 degrees are fed to the stator 829, the rotor 831 will rotate.

By the way, FIG. 57 shows a motor unit and driving force transmitting system, for example, for the up and down directions but a motor unit and driving force transmitting system for the light and left directions of the same formation are also provided.

The operation of this embodiment shall be explained in the following.

For example, when the up bending switch 809 is pushed, a driving electric power will be fed to the motor unit 823 from the ultrasonic motor controlling apparatus 820, advancing waves will be generated in the stator 829 and then the rotor 831 will rotate in the up direction. This rotating force will be transmitted through the shaft 832, gears 840 and 847 and pulley 848 to the bending operating wire 849 which will be pulled in the up direction. Likewise, when the down bending switch 810 is pushed, the pulley 848 will rotate in the reverse direction and the bending operating wire 849 will be pulled in the down direction. Also, when the right bending switch 811 or left bending switch 812 is pushed, a driving electric power from the above mentioned ultrasonic motor controlling circuit 820 will be fed to a motor unit for the right or left not illustrated and the bending operating wire will be pulled in the right or left direction, respectively.

Here, for example, when the motor unit 823 fails in the operation, the bending operating wire 849 will be locked by the pressed contact of the rotor 831 and stator 829 with each other. In such case, if the ring screw 825 is rotated and is removed from the operating section 802, then, due to the energizing force of the spring 844, in the motor unit 823, the flange 825b of the ring screw 825 will rise until it contacts the ring screw 828. At this time, the projection 826a of the base 826 will disengage from the recess of the operating section 802 and the gear 840 will move to the upper part of the gear 847. Therefore, the motor unit 823 will become rotatable with respect to the operating section 802. Therefore, such bending lock as is described above will be released.

Further, when each motor unit 823 is rotated by hand, the rotating force will be transmitted to the pulley 848, the bending operation wire 849 will be pulled and the bending portion 806 will become manually operable. That is to say, the housing 824 of the motor unit 823 is also a manual bending operation knob.

By the way, the motor unit for the right or left is also the same and shall not be explained here. Thus, according to this embodiment, the bendable portion 806 can be bent by using the ultrasonic motor of the motor unit 823 and, at such required time as when the motor unit 823 fails, the bendable portion 806 will be able to be made free and to be manually operated.

Figure 58:
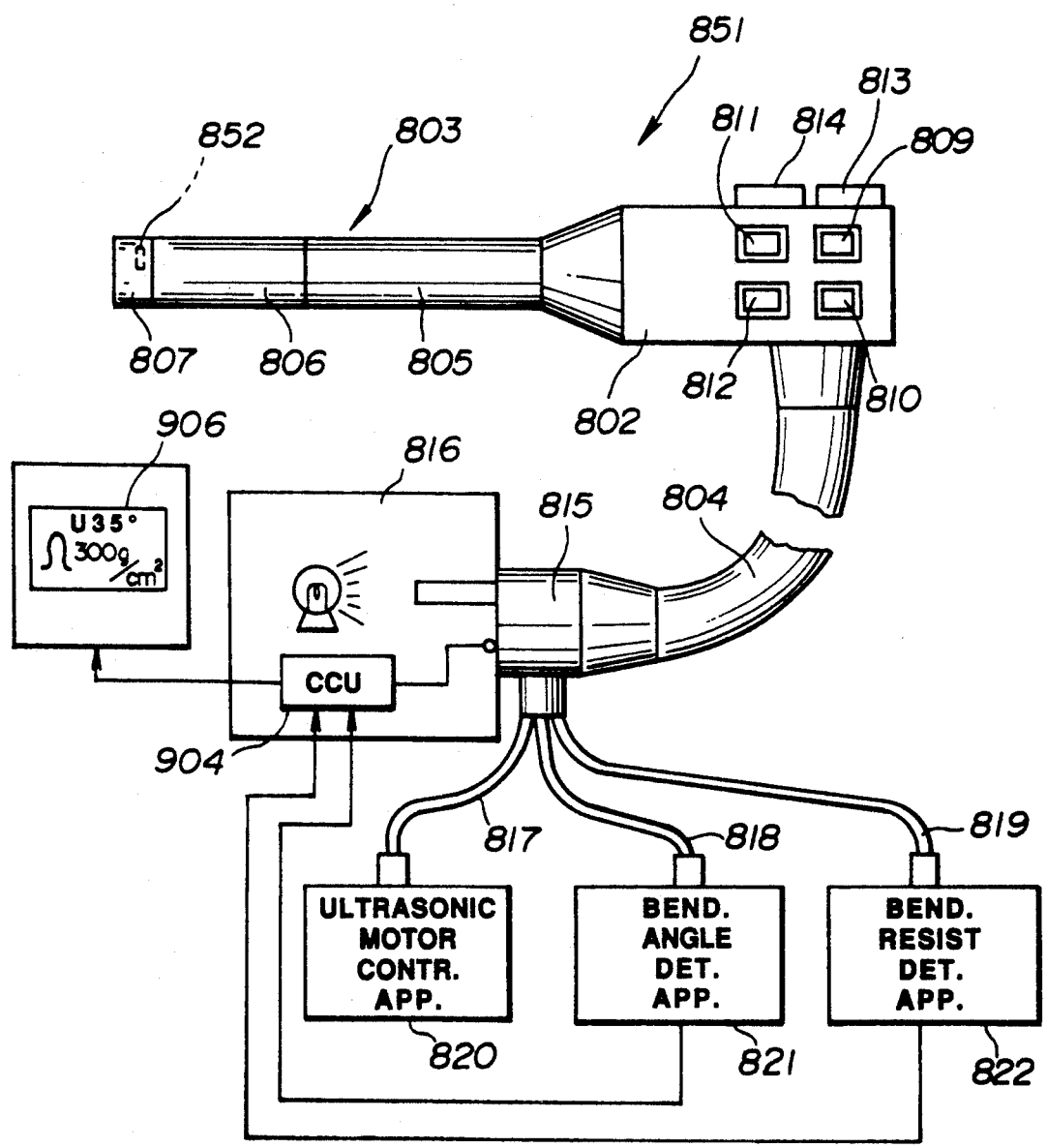
FIG. 58 is an explanatory diagram showing the whole of an endoscope system of the thirteenth embodiment of the present invention.

FIG. 58 is an explanatory view showing the whole of an endoscope system of the thirteenth embodiment of the present invention.

This embodiment is of an electronic scope instead of such fiber scope as in the twelfth embodiment.

In an electronic scope 851, no eyepiece portion 808 is provided and such solid state imaging device 852 as a CCD instead of an image guide is disposed in the image forming position of an objective lens system within a distal end component 807. Signal lines connected to this solid state imaging device 852 are inserted through an insert section 803, operating section 802 and universal cord 804 and is connected to a connector 815. The above mentioned solid state imaging device 852 is connected through this connector 815 to a CCU 904 provided within a light source apparatus 816 and is driven by the above mentioned CCU 904. The signal read out is processed to be a video signal by the CCU 904. The output video signal is input into a monitor 906 in which an object image is displayed.

Also, from a bending angle detecting apparatus 821 and bending resistance detecting apparatus 822, signals respectively for displaying bending angle and bending resistance values are input into the above mentioned CCU 904 which synthesizes the above mentioned bending angle and bending resistance values with the video signal output to the monitor 906 and displays in the above mentioned monitor 906 the bending angle and bending resistance values together with the object image.

The other formations, operations and effects are the same as in the twelfth embodiment.

By the way, the present invention is not limited to the above mentioned respective embodiments and the endoscope can be applied to endoscopes for all of such uses as medical, industrial and other uses and to endoscopes of all of such types as of fiber scopes and electronic scopes.

The present invention can be applied not only to the case of bending in four directions but also to the case of bending in two directions.

A wire for a treating instrument raising stand may be fitted instead of the bending operating wire and may be applied to the treating instrument raising motor operation.

The driving means is not limited to the ultrasonic motor but may be such other motor as a stepping motor.

Also, the bending wire may be pulled by a sprocket and chain instead of the pulley.

Figure 59:
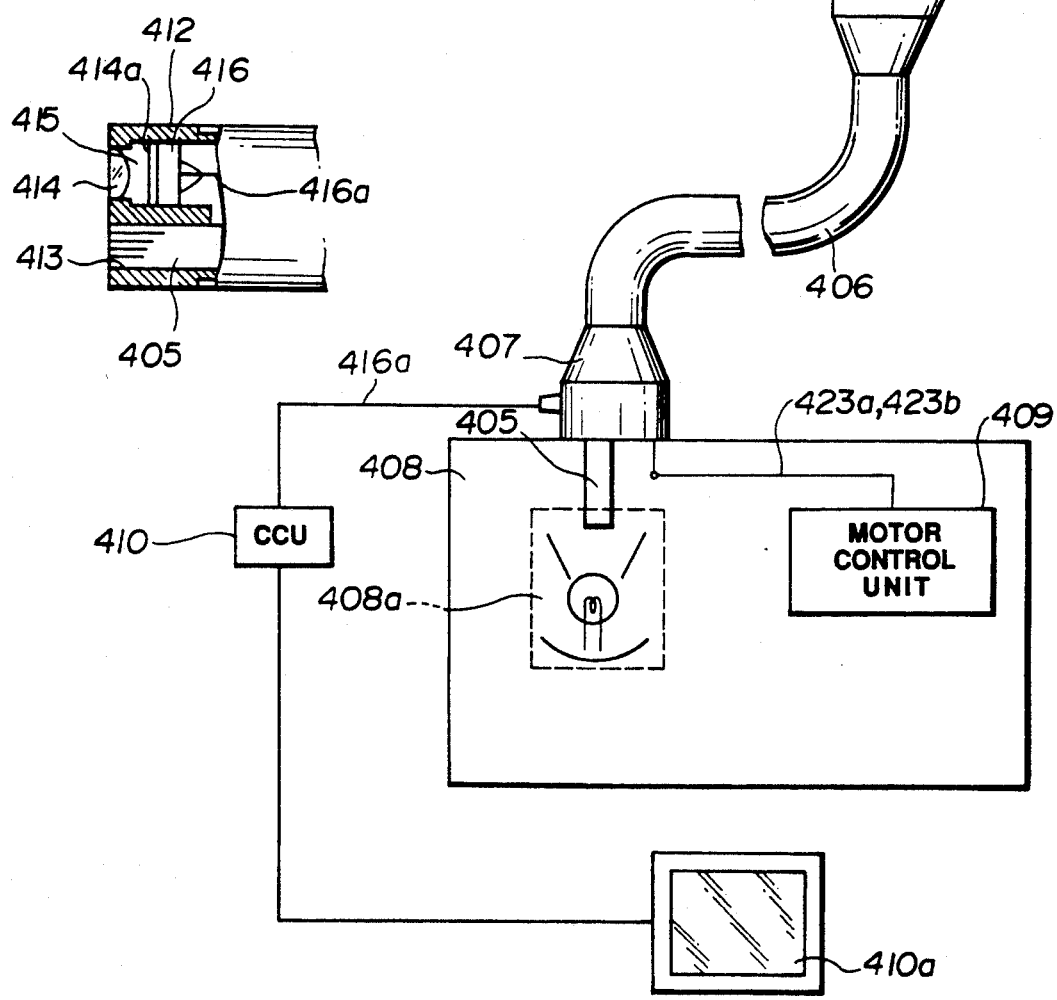

First, an endoscope system of the fourteenth embodiment shall be described briefly with reference to FIG. 59. An endoscope 401 comprises an elongate and flexible insert section 402 which can be inserted into a body cavity or the like and a relatively large diameter operating section 403 provided at the base end of the insert section 402.

The insert section 402 is provided at the distal end with a distal end component 412 formed of a rigid member. Adjacent to the base end of the distal end component 412 is provided a bendable portion 418 as an example of a driven member and comprising a plurality of articulate pieces which can mutually bend or pivot while expanding and contracting as a whole.

On the other hand, the operating section 403 is provided at the base end with an extended base portion 404 substantially orthogonal to the operating section 403. A light guide cable 403 incorporating a light guide 403 is extended from the end of the extended base portion 404.

A connector 407 is provided at the base end of the light guide cable 406 so that the light guide cable 406 may be connected to a light source unit 408 through the connector 407. When the connector 407 is connected to the light source unit 408, the entrance end of the light guide 405 will be positioned opposite a lamp 408a and a motor controlling unit 409 disposed in the light source unit 408 and a CCU 410 disposed outside it will be connected to the endoscope 301 through the connector 407.

The light guide 405 is extended through the insert section 402 and is fixed at one end in an illuminating through hole 413 formed in the distal end component 412 so that an illuminating light beam emitted from the lamp 408a may be radiated through the illuminating through hole 413 to a location to be observed. The distal end component 412 is provided also with an observing through hole 415 which includes an objective optical system 414 fixed therein and extends parallelly with the illuminating through hole 413. Such solid state imaging device 415 as a CCD is disposed in the focal plane of the objective optical system 414 along with a color mosaic filter 414 for separating colors. An optical image of the location to be observed focused by the objective optical system 414 is photoelectrically converted by the solid state imaging device 416 and the resulting video signal is output to the CCU 410 out of the light source unit 408 through a signal line 416a fixed to a substrate of the solid state imaging device 416. The CCU 410 is connected to a monitor 410a. Thus, the video signal from the solid state imaging device 416 is processed by the CCU 410 and is then output to the monitor 410a so that the image of the location to be observed may be visually observed in the monitor 410a.

The distal end component 412 includes also a suction port and an air feeding/water feeding port (both not illustrated). By actuating a suction switch 417a and an air feeding/water feeding switch 417b on the operating section 403, it is possible to perform such required operation as a suction or feeding air/feeding water.

Figure 60:
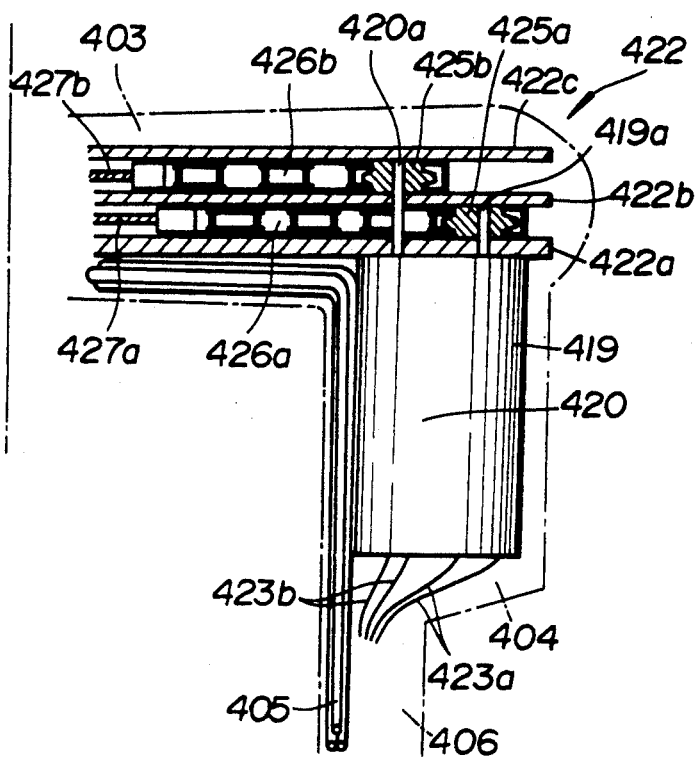

As shown in FIG. 60, a vertically (UD) bending DC motor 419 and a horizontally (RL) bending DC motor 420 as examples of driving units are disposed parallelly with each other in the extended base portion 404. On the base end side of the operating section 403, a frame assembly 422 comprising a first frame 422a, second frame 422b and third frame 422c is disposed parallelly with the axis of the operating section 403. The vertically bending DC motor 419 and horizontally bending DC motor 420 are fixed to the first frame 422a of the frame assembly 422 which is disposed nearest to the extended base portion 404.

Figure 62:
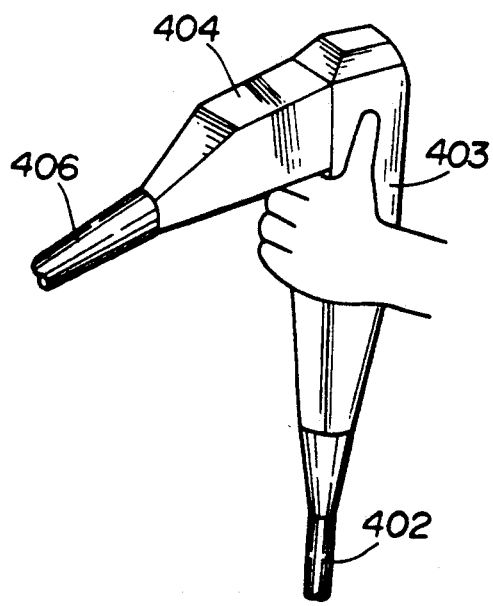

The DC motors 419 and 420 are connected to the motor controlling unit 409 disposed in the light source unit 408 through connecting lines 423a and 423b, respectively, and are operated by switches 424 disposed on the lateral surface of the operating section 403 and connected to the motor controlling unit 409. As shown in FIG. 59, the switches 424 comprise, for example, four push switches, that is, a pair of vertically (UD) bending switches 424a and 424b and a pair of horizontally (RL) bending switches 424c and 424d and a minute bending vibration on/off switch 424e. These switches are located in a region which the operator's forefinger can reach when the endoscope 401 is gripped by the left hand midway between the operating section 403 and the extended base portion 404, for example, as shown in FIG. 62. Incidentally, the respective pairs of push switches of the four switches 424a to 424d which are operated for bending in the opposite directions are arranged as seesaw switches so that, while one of the paired switches is being depressed, the other switch may not be depressed.

On the other hand, an output shaft 419a of the vertically bending DC motor 419 penetrates through the first frame 422a and is projected between the first frame 422a and the second frame 422b in a rotatable manner. An output shaft 420a of the horizontally bending DC motor 420 penetrates through the first and second frames 422a and 422b and is projected between the second frame 422b and the third frame 422c in a rotatable manner. Pulleys 425a and 425b are mounted respectively on the output shafts 419a and 419b at the ends.

Further, chains 426a and 426b each having a predetermined length are entrained around the pulleys 425a and 425b, respectively. Each of the chains 426a and 426b is extended at both ends toward the insert section 402 and each of the vertically bending wires 427a and horizontally bending wires 427b is fixed at one end to each of the chains 426a and 426b, respectively, at the extended end. These wires 427a and 427b are extended through the insert section 402 up to the distal end of the bendable portion 418. The horizontally bending wires 427b are fixed at the other ends to the corresponding right and left points of the assembly of articulated rings disposed at the distal end of the bendable portion 418 and the vertically bending wires 427a are fixed at the other ends to the corresponding upper and lower points of that assembly. Therefore, by tensioning and loosening the wires 427a and 427b, the bendable portion 418 is bent upward, downward, rightward and leftward, whereby the distal end component 412 can be directed toward the location to be observed.

Figure 63:
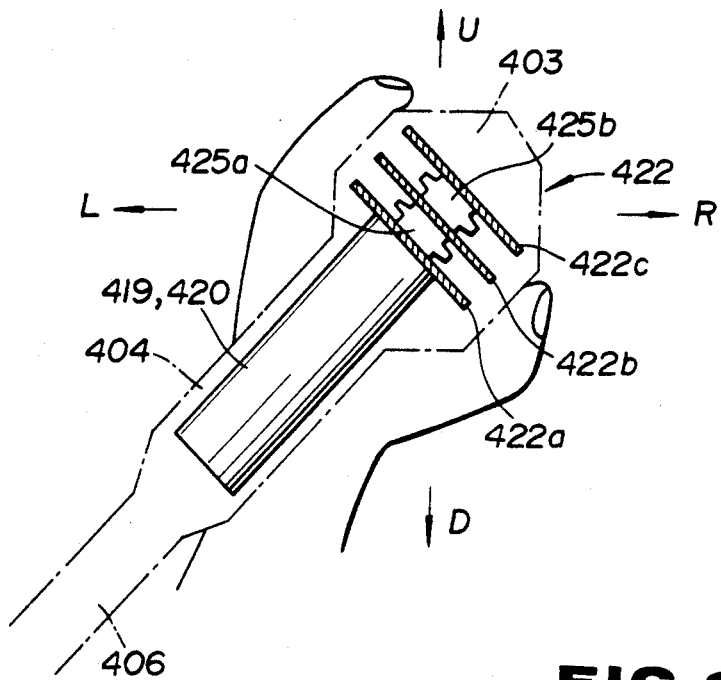
Figure 65:
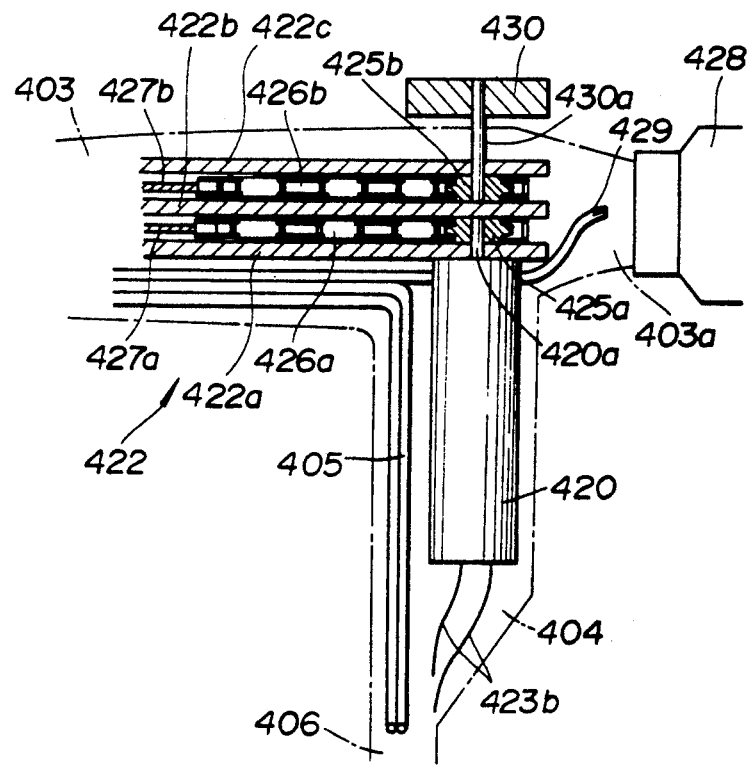
FIGS. 64 and 65 relate to the fifteenth embodiment of the present invention.
Figure 64:
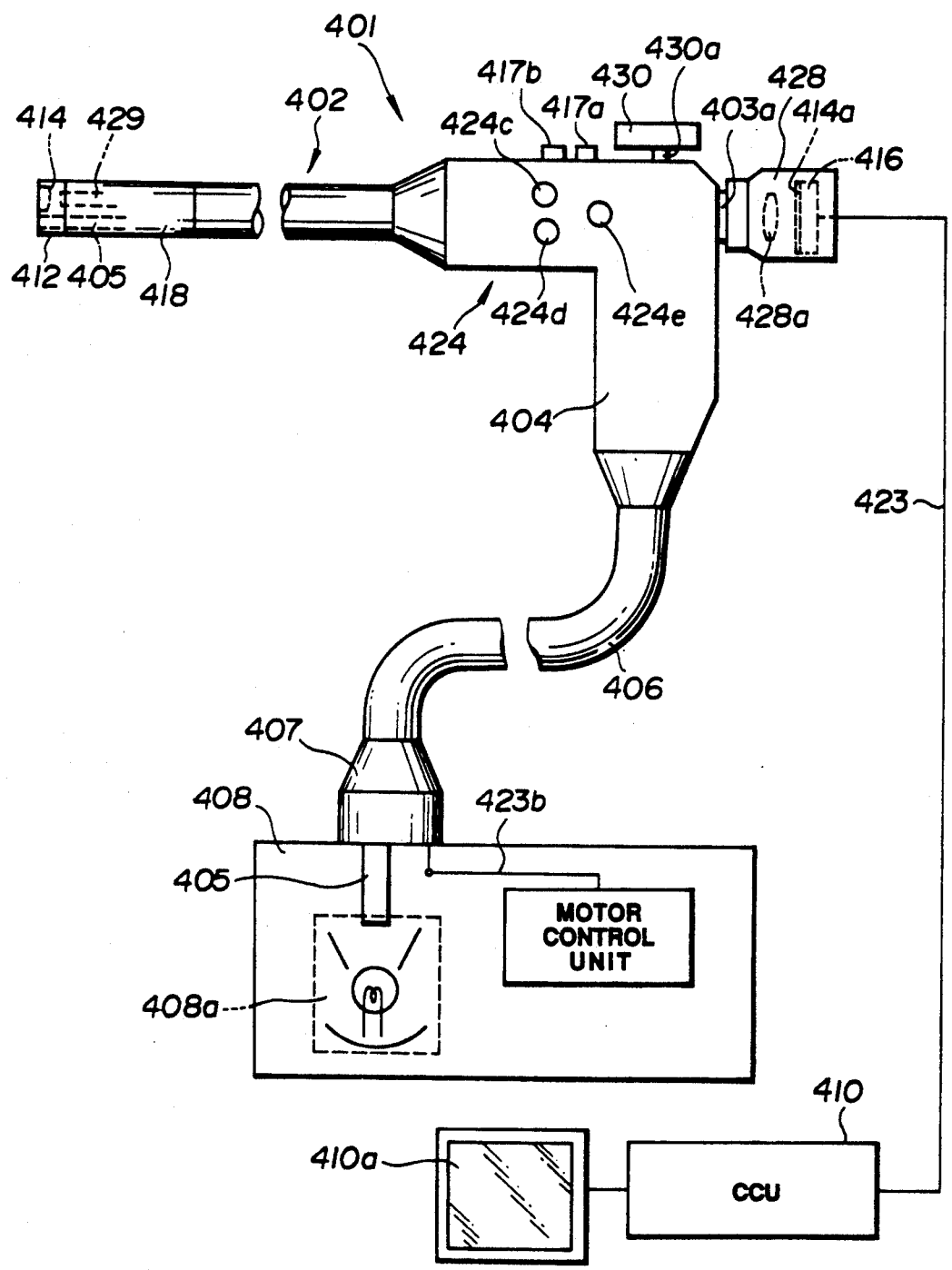

As shown in FIG. 63, the extended base portion 404 housing the DC motors 419 and 420 is provided obliquely with respect to the bending directions of the bendable portion 418 so that, when the operating section 403 is held, for example, by the left hand, the extended base portion 404 will rest on the back of the gripping hand. As a result, the weight of the DC motors 419 and 420, etc. will be able to be supported by the back of the gripping hand and the operating section 404 will be able to be easily supported and gripped.

In starting an observation with the endoscope thus formed, the insert section 402 is inserted into a body cavity or the like, the light guide cable 406 is connected to the light source unit 408 through the connector 407 and an electric power is fed to the light source unit 408. Then, an illuminating light beam emitted from the lamp 408a in the light source unit 408 is led by the light guide 405 into the distal end component 412 and is radiated through the illuminating through hole 413 in the distal end component 412 to the location to be observed.

An optical image of the location to be observed is focused by the objective optical system 414 through the color mosaic filter 414a for separating colors into an image area of the solid state imaging device 416, is photoelectrically converted and is applied to the CCU 410. The signal processed by the CCU 410 is output to the monitor 410a so that the image of the location to be observed may be visually observed in the monitor 410a.

In case the location to be observed is positioned laterally away from the axis of the insert section 402, the proper switch 424 will be operated to bend the bendable portion 418 to direct the distal end component 412 to the location to be observed.

More specifically, by depressing the upward bending switch 424a or the downward bending switch 424b, the vertically bending DC motor 419 is driven through the motor controlling unit 409 in the light source unit 408 and the pulley 425a is rotated through the output shaft 419a of the vertically bending DC motor 419. The rotation of the pulley 325a moves the chain 426a in the axial direction of the operating section 403, whereupon the vertically bending wires 427a fixed each at one end to the chain 426a at the respective ends are loosened or tensioned.

Since the vertically bending wires 427a are fixed at the other ends to the bendable portion 418 at the upper and lower points on the distal end side thereof, the bendable portion 418 will be bent vertically depending on the rotating angle of the pulley 425a when the vertically bending wires 427a fixed at the upper and lower points are tensioned or loosened. As a result, the distal end component 412 will be directed to the location to be observed which will be able to be visually observed in the monitor 310a.

By releasing the switch 424 from its operation when the distal end component 412 is just directed to the location to be observed, the DC motor 419 is stopped in the operation and the bendable portion 418 comes to rest as bent, allowing the observation to be continued.

The foregoing process is equally applied not only to the case of bending the bendable portion 418 up and down but also to the case of bending it to the right and left.

When it is required to return the bendable portion 419 to its straight form, the bendable portion 419 will be able to be easily returned to the straight form by operating the proper switch 424. In this connection, the state of the bendable portion 418 can be noticed with ease by so arranging as to detect the rotating positions of the pulleys 425a and 425b and to light up an indicator lamp disposed on the operating section 403, for example, when the pulleys 425a and 425b have returned to their initial states.

Although the vertically and horizontally bending DC motors 414 and 420 are used as driving units in this embodiment, the driving units are not necessarily limited to the DC motors 419 and 420. Alternately, the driving units may be any other types of motors such as AC motors, pulse motors, ultrasonic motors or fluid motors utilizing a hydraulic pressure.

Further, it is also possible to attach speed reducers to the DC motors 419 and 420 for increasing the torque produced to perform the bending.

FIG. 66 shows an endoscope system 901' of the sixteenth embodiment of the present invention. This system 901' has no illuminating light transmitting means (and no light source apparatus for feeding an illuminating light to this transmitting means) and is to directly emit an illuminating light from a distal end component of an endoscope.

In this system 901', an electronic endoscope 902' having a lamp 981 housed within a distal end component 913 is used instead of the electronic endoscope 902 having the light guide 916 built-in in the system 901 shown, for example, in FIG. 52 and a controlling unit 905' having no light source unit 903 in the system 901 shown in FIG. 52 is used. Further, a connector 911 is connected to a lamp power source 983 through a cable 982 connected to this connector 911. By this connection, the power source 983 feeds an electric power to the lamp 981 through a cable inserted through the electronic endoscope 902' to light this lamp 981. The light of this lamp 981 is radiated to a forward observed object side through a forward concave lens 984 to illuminate the object. The other formations are the same as in the system 901 shown in FIG. 52. By the way, the lamp power source 983 may be housed within the connector 911. Now, for example, LED's respectively emitting lights of respective wavelengths of red, green and blue may be used instead of the above mentioned lamp 981.

Figure 67:
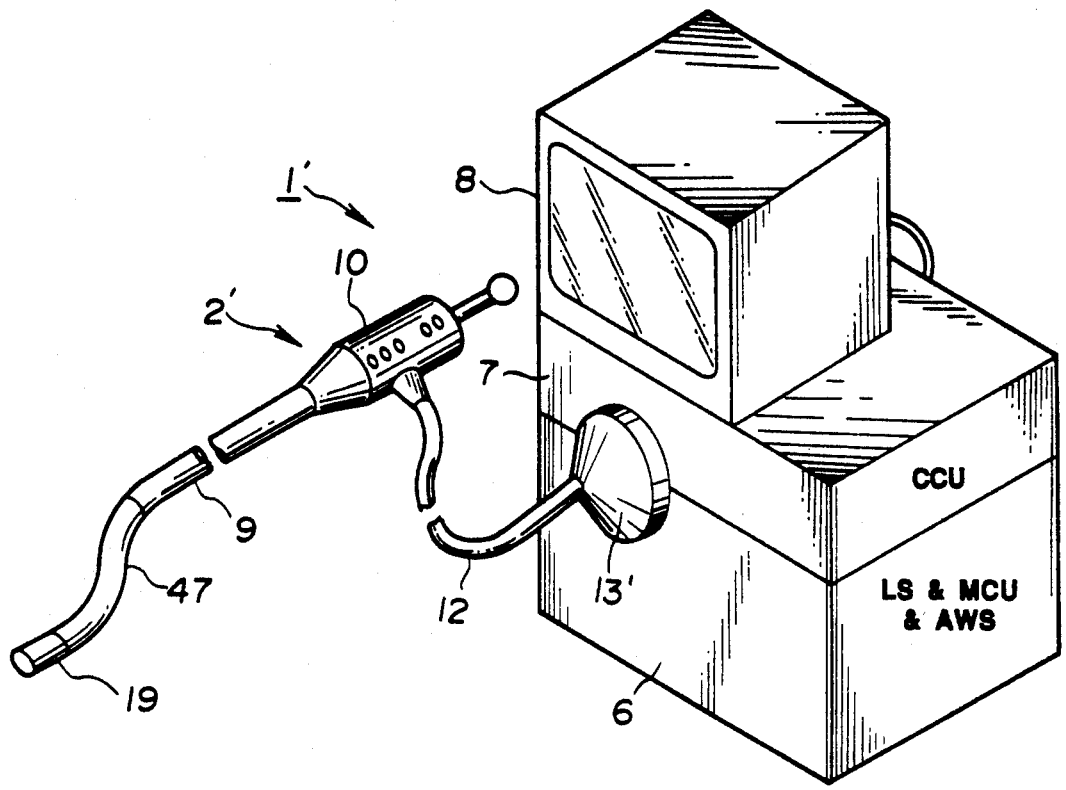

FIG. 67 shows an endoscope system 1' of the seventeenth embodiment of the present invention. In the above described respective embodiments, the endoscope has at least two separated connectors so as to be connected to at least a CCU and MCU, whereas, in this embodiment, one connector can be connected to a CCU and MCU separate from each other.

In this system 1' is used an electronic scope 2' provided with an integrated connector 13' instead of the connector 13, cable 15 and connectors 16 and 17 in the system 1 shown, for example, in FIG. 3. As shown in FIG. 68, this connector 13' is formed as divided into a first connector 17A and second connector 13A connectable respectively to connector receptacles 14 and 18 of a CCU 7 and an LS & MCU & AWS 6 separate from each other.

For example, the contact parts (represented by 17' in FIG. 68b) of the connector 17 provided at the end of the cable 15 extended out of the side of the connector 13 shown in FIG. 1 are formed as the contact parts of the first connector 17A and the contact parts of this first connector 17A are formed adjacently to the contact parts on the end surface of the connector 13 (shown in FIG. 1). By the way, in FIG. 68b, the light guide and others are omitted.

Figure 68A:
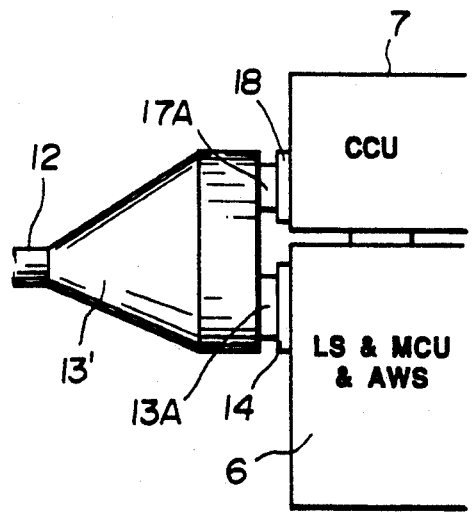
FIGS. 68a and 68b are respectively a side view and explanatory view showing connecting parts of a connector.
Figure 68B:
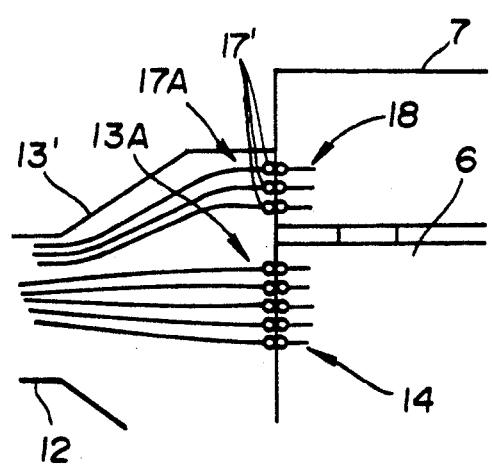

That is to say, as understood from FIG. 68a or 68b, the connector 13' is so formed that, in case the first connector 17A is connected to the CCU 7, the second connector 13A will project below the bottom surface of the CCU 7 and, in case the second connector 13A is connected to the LS & MCU & AWS 6, the first connector 17A will project above the upper surface of the LS & MCU & AWS 6. When the CCU 7 is arranged on the upper surface of the LS & MCU & AWS 6, the first connector 17A and second connector 13A will be able to be connected respectively to the connector receptacles 18 and 14 of the CCU 7 and LS & MCU & AWS 6. The other formations are the same as in the first embodiment. According to this embodiment, the electronic scope 2' shown in FIG. 67 can be used as connected and the electronic scope 2 shown in FIG. 3 can be also used as connected. The TV camera externally fitted scope 2C shown in FIG. 5a can be also used. This embodiment can be also applied to other embodiments.

It is to be noted that some of the aforementioned embodiments are optionally combined with each other to constitute further different embodiments and these modified embodiments are also involved in the scope of the present invention.

What is claimed is:

1. An electronic endoscope system comprising:
an electronic endoscope provided with an elongate and flexible insert section, an illuminating light emitting means for transmitting an illuminating light fed from outside and emitting it from an illuminating window of a distal end component of said insert section, an objective optical system provided in the distal and component of said insert section, an imaging means for photoelectrically converting an optical image based on said objective optical system and a first connector connected to a cable connected with said imaging means;

an electric operating means for electrically performing at least one of an operation of bending a bendable portion provided in said insert section, an operation of advancing and retreating movement of said insert section in the axial direction of said insert section and an operation of rotating said insert section around the axial direction of said insert section;

a second connector connected to a cable connected with said electric operating means;

a video signal processing unit provided with a first connector receptacle making said first connector connectable and processing a signal for said imaging means to produce a video signal;

an electric driving means for at least one of a bending driving means for bending and driving said bendable portion, an advancing and retreating driving means for advancing and retreating moving said insert section in the axial direction of said insert section and a rotating driving means for rotating driving said insert section in response to the operation of said electric operating means;

a controlling unit formed separately from said video signal processing unit, provided with a second connector receptacle making said second connector connectable and controlling said electric driving means in response to the operation of said electric operating means;

a light source apparatus provided with a connector receptable making the connector of said illuminating light emitting means connectable and feeding said illuminating light; and a monitor means for displaying said video signal.

2. An electronic endoscope system according to claim 1 wherein said electronic endoscope is an electronic scope in which a photoelectric converting surface of said imaging means is arranged in the focal plane of said objective optical system.

3. An electronic endoscope system according to claim 1 wherein said electronic endoscope is a TV camera externally fitted scope formed of a fiber scope having an image guide in which one end surface is arranged in the focal plane of said objective optical system and an optical image is transmitted to the other end surface on the eyepiece portion side and a TV camera which can be fitted to said eyepiece portion and has said imaging means built-in for photoelectrically converting the optical image transmitted to said other end surface.

4. An electronic endoscope system according to claim 1 wherein said electric operating means is provided in said electronic endoscope.

5. An electronic endoscope system according to claim 1 wherein said electric operating means has an electric bending operating means for electrically controlling the bending of said bendable portion, said electric driving means has said bending driving means for bending driving said bendable portion in response to the operation of said electric bending operating means and said controlling unit has a bending controlling unit controlling the bending drive of said bending driving means.

6. An electronic endoscope system according to claim 1 wherein said electric operating means has an electric advancing and retreating operating means for electrically advancing and retreating said insert section in the axial direction of said insert section, said electric driving means has said advancing and retreating driving means for advancing and retreating driving said insert section in the axial direction of said insert section in response to the operation of said electric advancing and retreating operating means and said controlling unit has an advancing and retreating controlling unit for controlling the advancing and retreating drive of said advancing and retreating driving means in response to the operation of said electric advancing and retreating operating means.

7. An electronic endoscope system according to claim 1 wherein said electric operating means has an electric rotating operating means for rotating said insert section around the axial direction of said insert section, said electric driving means has said rotating driving means for rotating said insert section around the axial direction of said insert section in response to the operation of said electric rotating operating means and said controlling unit has a rotation controlling unit for controlling the rotating drive of said rotating driving means in response to the operation of said electric rotating operating means.

8. An electronic endoscope system according to claim 1 wherein said electronic endoscope has an air feeding/water feeding tube for feeding air and feeding water and a sucking tube for suction.

9. An electronic endoscope system according to claim 8 having an electric air feeding/water feeding & sucking operating means for making an air feeding/water feeding operation and sucking operation and an electric air feeding/water feeding & sucking means for feeding air/feeding water & sucking through said air feeding/water feeding tube and said sucking tube in response to the operation of said electric air feeding/water feeding & sucking operating means.

10. An electronic endoscope system according to claim 9 wherein said electric air feeding/water feeding & sucking operating means is provided in said electronic endoscope.

11. An electronic endoscope system according to claim 9 having an air feeding/water feeding & sucking controlling unit for controlling feeding air/feeding water and controlling sucking respectively through said air feeding/water feeding tube and said sucking tube in response to the operation of said electric air feeding/water feeding & sucking operating means.

12. An electronic endoscope system according to claim 11 wherein said air feeding/water feeding & sucking controlling unit and said light source appartus are housed within a common housing.

13. An electronic endoscope system according to claim 12 wherein said air feeding/water feeding & sucking controlling unit and said controlling unit are housed within a common housing.

14. An electronic endoscope system according to claim 9 wherein said air feeding/water feeding & sucking controlling unit, said light source appartus and said controlling circuit unit are housed within a common housing.

15. An electronic endoscope system according to claim 1 wherein said controlling unit and said light source apparatus are housed within a common housing.

16. An electronic endoscope system according to claim 1 wherein said video signal processing unit and said light source apparatus are housed within a common housing.

17. An electronic endoscope system according to claim 9 wherein said video signal processing unit and said air feeding/water feeding & sucking controlling unit are housed within a common housing.

18. An electronic endoscope system according to claim 9 wherein said video signal processing unit, said light source apparatus and said air feeding/water feeding & sucking controlling unit are housed within a common housing.

19. An electronic endoscope system according to claim 1 wherein said electric operating means is an on/off operating switch.

20. An electronic endoscope system according to claim 5 wherein said electric bending operating means is a joystick.

21. An electronic endoscope system according to claim 1 wherein said electric driving means is formed of a motor.

22. An electronic endoscope system according to claim 5 wherein said bending driving means is provided within said electronic endoscope.

23. An electronic endoscope system according to claim 1 wherein said electric operating means has an electric bending operating means for electrically controlling the bending of said bendable portion, an electric advancing and retreating operating means for electrically advancing and retreating said insert section in the axial direction of said insert section and an electric rotating operating means for rotating said insert section around the axial direction of said insert section.

24. An electronic endoscope system according to claim 23 wherein said electric driving means has said bending driving means for bending and driving said bendable portion in response to the operation of said electric bending operating means, said advancing and retreating driving means for advancing and retreating said insert section in the axial direction of said insert section in response to the operation of said electric advancing and retreating operating means and said rotating driving means for rotating said insert section around the axial direction of said insert section.

25. An electronic endoscope system according to claim 24 wherein said controlling unit has a bending controlling unit for controlling the bending drive of said bending driving means, an advance and retreat controlling unit for controlling the advancing and retreating drive of said advancing and retreating driving means and a rotation controlling unit for controlling the rotating drive of said rotating driving means.

26. An electronic endoscope system according to claim 6 wherein said advancing and retreating driving means has a ring-like member contacting the outer peripheral surface on the base end side of said insert section and a motor advancing and retreating said insert section by rotating and driving said ring-like member.

27. An electronic endoscope system according to claim 7 wherein said rotating driving means has a ring-like member contacting the outer peripheral surface on the base end side of said insert section and a motor rotating said insert section around the axial direction of said insert section by rotating and driving said ring-like member.

28. An electronic endoscope system according to claim 5 wherein said bending controlling unit has a bending vibration controlling function of feeding a vibrating driving signal to said bending driving means and vibrating said bendable portion and said electric bending operating means has a bending vibrating operating means for selecting said bending vibration control.

29. An electronic endoscope system according to claim 6 wherein said advance and retreat controlling unit has an advancing and retreating vibration controlling function of feeding a vibrating driving signal to said advancing and retreating driving means and vibrating said insert section in the axial direction of said insert section and said electric advancing and retreating operation means has an advancing and retreating vibrating operating means for selecting said advancing and retreating vibration control.

30. An electronic endoscope system according to claim 7 wherein said rotation controlling unit has a rotating vibration controlling function of feeding a vibrating driving signal to said rotating driving means and vibrating said insert section around the axial direction of said insert section and said electric rotating operating means has a rotating vibrating operating means for selecting said rotating vibration control.

31. An electronic endoscope system according to claim 1 wherein said first connector cable and said second connector cable are inserted through one coating member.

32. An electronic endoscope system according to claim 1 wherein said first connector and said second connector are integrated to form an integrated connector.

33. An electronic endoscope system according to claim 31 wherein one of said first connector cable and said second connector cable is further extended out of the other cable connector.

34. An electronic endoscope system according to claim 32 wherein said video signal processing unit and said controlling unit will form a connector receptacle which can connect said integrated connector when combined with each other.

35. An electronic endoscope system according to claim 1 wherein said first connector and said second connector are formed as separated.

36. An electronic endoscope system comprising:
an electronic endoscope provided with an elongated and flexible insert section, an illuminating light emitting means for emitting an illuminating light from a distal end component of said insert section, an objective system provided in the distal end component of said insert section, an imaging means for photoelectrically converting an optical image based on said objective optical system and a first connector connected to a cable connected with said imaging means;
an electric operating means for electrically performing at least one of an operation of bending a bendable portion provided in said insert section, an operation of advancing and retreating driving said insert section in the axial direction of said insert section and an operation of rotating said insert section around the axial direction of said insert section;
a second connector connected to a cable connected with said electric operating means;
a video signal processing unit provided with a first connector receptable making said first connector connectable and processing a signal for said imaging means to produce a video signal;
an electric driving means of at least one of a bending driving means for bending and driving said bendable portion, an advancing and retreating driving means for advancing and retreating moving said insert section in the axial direction of said insert section in response to the operation of said electric operating means;

a controlling unit formed separately from said video signal processing unit, provided with a second connector receptable making said second connector connectable and controlling said electric driving means in response to the operation of said electric operating means; and a monitor means for displaying said video signal.

37. An electronic endoscope system according to claim 36 wherein said first connector cable and said second connector cable are inserted through one coating member.

38. An electronic endoscope system according to claim 1 wherein said first connector and said second connector are integrated to form an integrated connector.

39. An electronic endoscope system according to claim 37 wherein one of said first connector cable and said second connector cable is further extended out of the other cable connector.

40. An electronic endoscope system according to claim 38 wherein said video signal processing unit and said controlling unit will form a connector receptacle which can connect said integrated connector when combined with each other.

41. An electronic endoscope system according to claim 36 wherein said first connector and said second connector are formed as separated.

42. An electronic endoscope system according to claim 36 having a light emitting body provided in the distal end component of said insert section and a driving means for driving said light emitting body.

* * * * *